(12) United States Patent
Murali et al.

(10) Patent No.: US 12,091,707 B2
(45) Date of Patent: *Sep. 17, 2024

(54) DETECTION OF NUCLEIC ACID AND NON-NUCLEIC ACID TARGET MOLECULES

(71) Applicant: VedaBio, Inc., San Diego, CA (US)

(72) Inventors: Swetha Murali, San Diego, CA (US); Andrew Garst, San Diego, CA (US); Anurup Ganguli, San Diego, CA (US); Ketki Sawant, San Diego, CA (US); Ravi Vijayendran, San Diego, CA (US)

(73) Assignee: VedaBio, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/612,868

(22) Filed: Mar. 21, 2024

(65) Prior Publication Data

US 2024/0247304 A1 Jul. 25, 2024

Related U.S. Application Data

(63) Continuation of application No. 18/377,294, filed on Oct. 5, 2023, now Pat. No. 11,965,205.

(60) Provisional application No. 63/442,734, filed on Feb. 1, 2023, provisional application No. 63/427,280, filed on Nov. 22, 2022, provisional application No. 63/416,332, filed on Oct. 14, 2022.

(51) Int. Cl.
*C12Q 1/682* (2018.01)
*C12N 9/22* (2006.01)

(52) U.S. Cl.
CPC .............. *C12Q 1/682* (2013.01); *C12N 9/22* (2013.01); *C12N 2310/20* (2017.05)

(58) Field of Classification Search
CPC ....... C12Q 1/682; C12N 9/22; C12N 2310/20
See application file for complete search history.

(56) References Cited

U.S. PATENT DOCUMENTS

| | | |
|---|---|---|
| 10,253,365 B1 | 4/2019 | Doudna et al. |
| 10,266,886 B2 | 4/2019 | Abudayyeh et al. |
| 10,266,887 B2 | 4/2019 | Abudayyeh et al. |
| 10,337,051 B2 | 7/2019 | Doudna et al. |
| 10,377,998 B2 | 8/2019 | Zhang et al. |
| 10,494,664 B2 | 12/2019 | Doudna et al. |
| 11,021,740 B2 | 6/2021 | Abudayyeh et al. |
| 11,060,115 B2 | 7/2021 | Severinov et al. |
| 11,104,937 B2 | 8/2021 | Abudayyeh et al. |
| 11,118,224 B2 | 9/2021 | Doudna et al. |
| 11,149,259 B2 | 10/2021 | Zhang et al. |
| 11,174,470 B2 | 11/2021 | Harrington et al. |
| 11,174,515 B2 | 11/2021 | Abudayyeh et al. |
| 11,273,442 B1 | 3/2022 | Chen et al. |
| 11,421,250 B2 | 8/2022 | Severinov et al. |
| 11,447,824 B2 | 9/2022 | Doudna et al. |
| 11,584,955 B2 | 2/2023 | Wang et al. |
| 2010/0286082 A1 | 11/2010 | Breaker et al. |
| 2014/0377748 A1 | 12/2014 | Tan et al. |
| 2015/0225773 A1* | 8/2015 | Farmer ................ C12Q 1/6806 435/6.12 |
| 2016/0040189 A1 | 2/2016 | Kennedy et al. |
| 2016/0083785 A1 | 3/2016 | Bone et al. |
| 2016/0186213 A1 | 6/2016 | Zhang et al. |
| 2018/0023081 A1 | 1/2018 | Hagedom et al. |
| 2018/0155716 A1 | 6/2018 | Zhang et al. |
| 2018/0282722 A1 | 10/2018 | Jakimo et al. |
| 2019/0112648 A1 | 4/2019 | Schaal et al. |
| 2019/0201550 A1 | 7/2019 | Maeder et al. |
| 2019/0241954 A1 | 8/2019 | Doudna et al. |
| 2019/0256900 A1 | 8/2019 | Zhang et al. |
| 2020/0010879 A1 | 1/2020 | Doudna et al. |
| 2020/0056167 A1 | 2/2020 | Dong et al. |
| 2020/0157611 A1 | 5/2020 | Qi et al. |
| 2020/0165594 A1 | 5/2020 | Zhang et al. |
| 2020/0277600 A1 | 9/2020 | Zhang et al. |
| 2020/0392473 A1 | 12/2020 | Zhang et al. |
| 2021/0040543 A1* | 2/2021 | Trepagnier ............. G16B 30/20 |
| 2021/0102183 A1 | 4/2021 | Cameron et al. |
| 2021/0102242 A1 | 4/2021 | Chen et al. |
| 2021/0108267 A1 | 4/2021 | Zhang et al. |

(Continued)

FOREIGN PATENT DOCUMENTS

| | | |
|---|---|---|
| CN | 113324956 | 8/2021 |
| CN | 114058679 A | 2/2022 |

(Continued)

OTHER PUBLICATIONS

Li, et al., "Applying CRISPR-Cas12a as Signal Amplifier to Construct Biosensors for Non-DNA Targets in Ultra-low Concentrations", ACS Sensors, doi: 10.1021/acssensors.9b02305, pp. 1-23, Mar. 12, 2020.

Kim, et al., "Chimeric crRNAs with 19 DNA residues in the guide region show retained DNA cleavage activity of Cas9 with a potential to improve the specificity", The Royal Society of Chemistry, pp. 1-16, 2019.

Kim, et al., "Enhancement of target specificity of CRISPR-Cas12a by using a chimeric DNA-RNA guide", Nucleic Acids Research, doi: 10.1093/nar/gkaa605, vol. 48, No. 15, pp. 8601-8616, Jul. 20, 2020.

(Continued)

*Primary Examiner* — Nancy J Leith
*Assistant Examiner* — Kyle T Rega
(74) *Attorney, Agent, or Firm* — Sarah Brashears

(57) ABSTRACT

The present disclosure relates to compositions of matter and assay methods used to detect one or more non-nucleic acid targets of interest in a sample. The compositions and methods provide signal boost upon detection of non-nucleic acid targets of interest in less than one minute and in some instances instantaneously at ambient temperatures down to 25° C. or less, allow for massive multiplexing, high accuracy, minimal non-specific signal generation, and are easily reprogrammable.

30 Claims, 24 Drawing Sheets

Specification includes a Sequence Listing.

(56) References Cited

U.S. PATENT DOCUMENTS

| | | |
|---|---|---|
| 2021/0163944 A1 | 6/2021 | Zhang et al. |
| 2021/0166783 A1 | 6/2021 | Shmakov et al. |
| 2021/0269866 A1 | 9/2021 | Zhang et al. |
| 2021/0317527 A1 | 10/2021 | Doudna et al. |
| 2021/0388437 A1 | 12/2021 | Doudna et al. |
| 2022/0025463 A1 | 1/2022 | Abudayyeh et al. |
| 2022/0333208 A1 | 10/2022 | Gootenberg et al. |
| 2023/0193368 A1 | 6/2023 | Rananaware et al. |

FOREIGN PATENT DOCUMENTS

| | | |
|---|---|---|
| CN | 114262730 A | 4/2022 |
| WO | WO 2014/143228 A1 | 9/2014 |
| WO | WO 2016/201138 A1 | 12/2016 |
| WO | WO 2020/191248 | 9/2020 |
| WO | WO 2020/191376 | 9/2020 |
| WO | WO 2021/021532 A1 | 2/2021 |
| WO | WO 2021/108717 A2 | 6/2021 |
| WO | WO 2021/146534 A1 | 7/2021 |
| WO | WO 2021/236651 A1 | 11/2021 |
| WO | WO 2021/243276 | 12/2021 |
| WO | WO 2022/061166 A1 | 3/2022 |
| WO | WO 2022/133108 A2 | 6/2022 |
| WO | WO 2022/266513 A2 | 12/2022 |
| WO | WO 2023/278629 A1 | 1/2023 |
| WO | WO 2023/287669 A2 | 1/2023 |
| WO | WO 2023/015259 A2 | 2/2023 |
| WO | WO 2023/056451 A1 | 4/2023 |
| WO | WO 2023/081902 A1 | 5/2023 |
| WO | WO 2023/114052 A1 | 6/2023 |
| WO | WO 2023/114090 A2 | 6/2023 |

OTHER PUBLICATIONS

Swarts, et al., "Mechanistic Insights into the Cis- and Trans-acting Deoxyribonuclease Activities of Cas12a", Mol Cell, doi: 10.1016/j.molcel.2018.11.021, pp. 1-28, Feb. 7, 2019.

Nguyen, et al., "Enhancement of trans-cleavage activity of Cas12a with engineered crRNA enables amplified nucleic acid detection", Nature Communications, doi: 10.1038/s41467- 020-18615-1, pp. 1-13, 2020.

Ooi, et al., "An engineered CRISPR-Cas12a variant and DNA-RNA hybrid guides enable robust and rapid COVID-10 testing", Nature Communications, doi: 10.1038/s41467-021-21996-6, pp. 1-23, 2021.

Shi, et al., "A CRISPR-Cas autocatalysis-driven feedback amplification network for supersensitive DNA diagnostics", Science Advances, doi: 10.1126/sciadv.abc7802, pp. 1-9, Jan. 27, 2021.

The Board of Trustees of the University of Illinois, "CRISPR Cascade", International PCT Application No. PCT/US22/33985, filed Jun. 17, 2022.

Chen, et al., "CRISPR-Cas12a target binding unleashes indiscriminate single-stranded DNase activity", Howard Hughes Medical Institute, Science, 360(6387), pp. 436-439, Apr. 27, 2018.

Liu, et al., "Accelerated RNA detection using tandem CRISPR nucleases", Nature Chemical Biology, vol. 17, doi:10.1038/s41589-021-0084202, pp. 982-988, Sep. 2021.

Gootenberg, et al., "Nucleic acid detection with CRISPR-Cas13a/C2c2", Science, doi:10.1126/science.aam9321, pp. 438-442, Apr. 28, 2017.

Fozouni, et al., "Amplification-free detection of SARS-COV-2 with CRISPR-Cas13a and mobile phone microscopy", Cell, doi.org/10.1016/j.cell.2020.12.001, pp. 323-333, Jan. 21, 2021.

Kaminski, et al., "CRISPR-based diagnostics", Nature Biomedical Engineering, vol. 5, doi.org/10.1038/s41551-021-00760-7, pp. 643-656, Jul. 2021.

Zhou, et al., "CRISPR/Cas13a Powered Portable Electrochemiluminescence Chip for Ultrasensitive and Specific MiRNA Detection", Advanced Science News, doi: 10.1002/advs.201903661, pp. 1-10, 2020.

Zhao, et al., "CRISPR-Cas13a system: A novel tool for molecular diagnostics", Frontiers in Microbiology, doi:10.3389/fmicb.2022.1060947, pp. 1-18, Dec. 8, 2022.

Zhou, et al., "A Decade of CRISPR Gene Editing in China and Beyond: A Scientometric Landscape", The CRISPR Journal, vol. 4, No. 3, doi:10.1089/crispr.2020.0148, pp. 313-320, 2021.

Shinoda, et al., "Automated amplification-free digital RNA detection platform for rapid and sensitive SARS-COV-2 diagnosis", Communications Biology, doi.org/10.1038/s42003-022-03433-6, pp. 1-8, May 26, 2022.

Gupta, et al., "Cas13d: A New Molecular Scissor for Transcriptome Engineering", Frontiers in Cell and Developmental Biology, vol. 10, doi:10.3389/fcell.2022.866800, pp. 1-22, Mar. 31, 2022.

Schunder, et al., "First indication for a functional CRISPR/Cas system in Francisella tularensis", International Journal of Medical Microbiology, vol. 303, Issue 2, doi:10.1016/j.ijmm.2012.11.004, pp. 1-29, Mar. 2013.

Sha, et al., "Cascade CRISPR/cas enables amplification-free microRNA sensing with fM-sensitivity and single-base-specificity", ChemComm, doi:10.1039/d0cc06412b, pp. 247-250 and 1-15, 2021.

Yang, et al., "Engineered LwaCas13a with enhanced collateral activity for nucleic acid detection", Nature Chemical Biology, vol. 19, doi:10.1038/s41589-022-01135-y, pp. 45-54, Jan. 2023.

East-Seletsky, et al., "RNA targeting by functionally orthogonal Type VI-A CRISPR-Cas enzymes", Howard Hughes Medical Institute, Mol Cell, pp. 373-383, May 4, 2017.

Schmidt, et al., "Application of locked nucleic acids to improve aptamer in vivo stability and targeting function", Nucleic Acids Research, vol. 32, No. 19, doi:10.1093/nar/gkh862, pp. 5757-5765, Oct. 27, 2004.

Makarova, et al., "Evolutionary classification of CRISPR-Cas systems: a burst of class 2 and derived variants", Nature Reviews | Microbiology, vol. 18, pp. 67-83, Feb. 2020.

Gleditzsch, et al., "PAM identification by CRISPR-Cas effector complexes: diversified mechanisms and structures", RNA Biology, vol. 16, No. 4, doi.org/10.1080/15476286.2018.1504546, pp. 504-517, Jul. 20, 2018.

Kellner, et al., "Sherlock: Nucleic acid detection with CRISPR nucleases", Nat Protoc., doi:10.1038/s41596-019-0210-2, pp. 2986-3012, Oct. 2019.

Liu, et al., "Directed Evolution of CRISPR/Cas Systems for Precise Gene Editing", Trends in Biotechnology, vol. 39, No. 3, Mar. 2021, p. 262-273.

International Search Report and Written Opinion for International Application No. PCT/US2022/036610, dated Jun. 29, 2023, p. 1-93.

International Search Report and Written Opinion for International Application No. PCT/US22/52320, dated Jun. 15, 2023, p. 1-46.

International Search Report and Written Opinion for International Application No. PCT/US2022/052032, dated Apr. 18, 2023, p. 1-19.

Zhang, et al., "An aM-level cascade CRISPR-Dx system (ASCas) for rapid detection of RNA without pre-amplification", Biosensors and Bioelectronics, doi:10.1016/j.bios.2023.115248, Mar. 28, 2023, p. 1-5.

Zeng, et al., "Rapid RNA detection through intra-enzyme chain replacement-promoted Cas13a cascade cyclic reaction without amplification", Analytica Chimica Acta, doi:10.1016/j.aca.2022.340009, May 31, 2022, p. 1-10.

Collias, et al., "CRISPR technologies and the search for the PAM-free nuclease", Nature Communications, doi: 10.1038/s41467-020-20633-y, 2021, p. 1-12.

Huyke, et al., "Enzyme Kinetics and Detector Sensitivity Determine Limits of Detection of Amplification-Free CRISPR-Cas12 and CRISPR-Cas13 Diagnostics", Analytical Chemistry, doi:10.1021/acs.analchem.2601670, Jun. 27, 2022, p. 9826-9834.

Mullally, et al., "5' modifications to CRISPR-Cas9 gRNA can change the dynamics and size of R-loops and inhibit DNA cleavage", Nucleic Acids Research, DOI:10.1093/nar/gkaa477, Jun. 2020, vol. 48, No. 12, p. 6811-6823.

Hong, et al., "Comparison and optimization of CRISPR/dCas9/gRNA genome-labeling systems for live cell imaging", Genome Biology, DOI: 10.1186/s13059-018-1413-5, 2018, p. 7-8.

(56) References Cited

OTHER PUBLICATIONS

Li, et al., "CRISPR-Cas 12a has both cis- and trans-cleavage activities on single-stranded DNA", Cell Research, DOI: 10.1038/s41422-018-0022-x, Feb. 5, 2018, p. 1-3.
Dong, et al., "An anti-CRISPR protein disables type V Cas12a by acetylation", PubMed, DOI:10.1038/s41594-019-0206-1, Feb. 28, 2023, p. 1-1.
Coehlo, et al., "CRISPR Guard protects off-target sites from Cas9 nuclease activity using short guide RNAs", Nature Communications, DOI: 10.1038/s41467-020-17952-5, Aug. 17, 2020, p. 1-12.
Click Chemistry, "Introduction: Click Chemistry", Chem. Rev. 2021, doi/10.1021/acs.chemrev.1c00469, p. 6697-6698.
MacConnell, et al., "An Integrated Microfluidic Processor for DNA-Encoded Combinatorial Library Functional Screening", ACS Combinatorial Science, DOI: 10.1021/acscombsci.6b00192, p. 181-192.
Mendes, et al., "High-throughput Identification of DNA-Encoded IgG Ligands that Distinquish Active and Latent Mycobacterium Tuberculosis Infections", ACS Chem Biol., Jan. 20, 2017, doi:10.1021/acschembio.6b00855, p. 1-19.
Gerry, et al., "Unifying principles of bifunctional, proximity-inducing small molecules", Nat Chem Biol., Apr. 1, 2020, doi:10.1038/s41589-020-0469-1, p. 1-24.
Bowley, et al., "Libraries against libraries for combinatorial selection of replicating antigen-antibody pairs", PNAS, Feb. 3, 2009, vol. 106, doi:10.1073/pnas.0812291106, p. 1380-1385.
Kempton, et al., "Multiple Input Sensing and Signal Integration Using a Split Cas12a System", Molecular Cell, Apr. 2, 2020, p. 184-191.
Holt, et al., "By-passing selection: direct screening for antibody-antigen interactions using protein arrays", Nucleic Acids Research, Jun. 16, 2000, vol. 28, No. 15, p. 1-5.
Delley, et al., "Microfluidic particle zipper enables controlled loading of droplets with distinct particle types", Lab Chip., Jul. 14, 2020, doi:10.1039/d01c00339e, p. 2465-2472.
Betancur, et al., "miRNA-like duplexes as RNAi triggers with improved specificity", Frontiers in Genetics, vol. 3, doi: 10.3389/fgene.2012.00127, pp. 1-6, Jul. 12, 2012.
Deng, et al., "Topological barrier to Cas12a activation by circular DNA nanostructures facilitates autocatalysis and transforms DNA/RNA sensing", Nature Communications, doi.org/10.1038/s41467-024-46001-8, pp. 1-16, Mar. 5, 2024.
Koonin, et al., "Diversity, classification and evolution of CRISPR-Cas systems", Current Opinion in Microbiology, 2017, 37, pp. 67-78, Jun. 9, 2017.
Zhou, et al., "High-throughput split-protein profiling by comgining transposon mutagenesis and regulated protein-protein interactions with deep sequencing", International Journal of Biological Macromolecules, pp. 543-552, Feb. 2, 2022.
International Search Report and Written Opinion for International Application No. PCT/US23/34598, dated Feb. 8, 2024, p. 1-25.
International Search Report and Written Opinion for International Application No. PCT/US23/34231, dated Feb. 16, 2024, p. 1-19.
International Search Report and Written Opinion for International Application No. PCT/US23/33554, dated Feb. 13, 2024, p. 1-23.

* cited by examiner

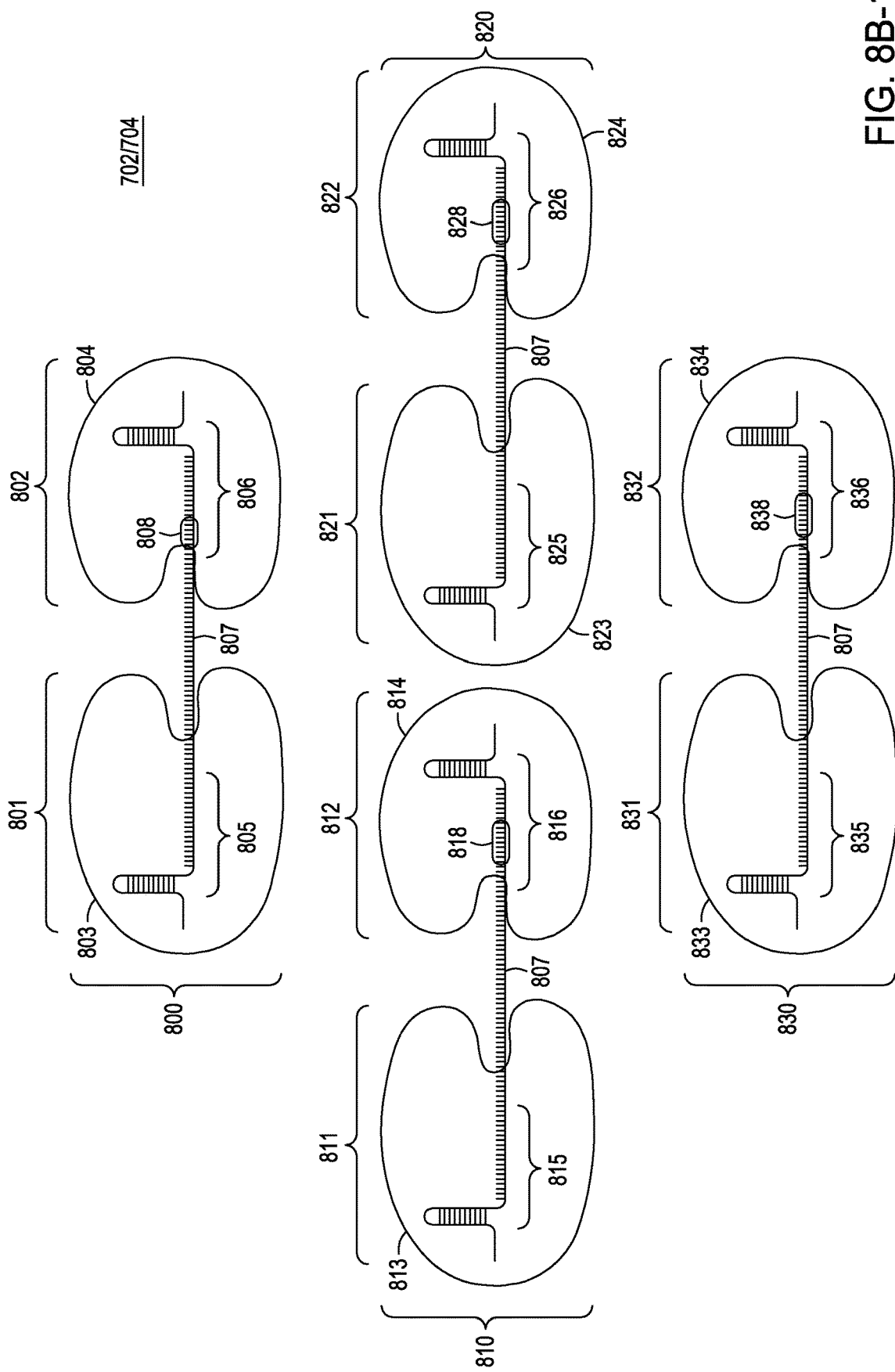

DETECTION OF NUCLEIC ACID AND NON-NUCLEIC ACID TARGET MOLECULES

RELATED APPLICATIONS

This application is a continuation of U.S. Ser. No. 18/377,294, filed 5 Oct. 2023, which claims priority to U.S. Ser. No. 63/416,332, filed 14 Oct. 2022; U.S. Ser. No. 63/427,280 filed 22 Nov. 2022; and U.S. Ser. No. 63/442,734 filed 1 Feb. 2023, all of which are incorporated by reference in their entirety.

INCORPORATION BY REFERENCE OF SEQUENCE LISTING

Submitted herewith is an electronically filed sequence listing via EFS-Web a Sequence Listing XML named VB007US2_seglist_20240319, created 18 Mar. 2024, 10,224 bytes in size. The sequence listing is part of the specification of this specification and is incorporated by reference in its entirety.

FIELD OF THE INVENTION

The present disclosure relates to compositions of matter and assay methods used to detect one or more nucleic acid targets and/or non-nucleic acid targets of interest in a sample. The compositions and methods provide a signal boost upon detection of targets of interest in less than one minute.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Aptamers are short, single-stranded oligonucleotides that bind to target molecules with specificity and high affinity by folding into tertiary configurations. Although aptamers recognize and bind non-nucleic acid targets much like antibodies, aptamers have a number of advantages over antibodies; for example, aptamers have a low cost of manufacture, are easily modified without losing efficacy, have a short generation time compared to that for antibodies, and inherently possess far less batch-to-batch variability. To date, aptamers have been used in basic research and to monitor food production and the environment; however, there is increasing interest in applying aptamer technology to diagnostics and therapeutics, such as, e.g., biosensors and target inhibitors. For example, diagnostic applications include pathogen detection, cancer detection and monitoring, and stem cell recognition, while therapeutic applications include use of aptamers for targeted drug delivery.

Further, in many applications it is desirable to detect both non-nucleic acid targets of interest and nucleic acid targets of interest simultaneously in a single assay. The methods and compounds presented herein allow for such detection.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides compositions of matter and assay methods to detect nucleic acid targets of interest and non-nucleic acid targets of interest in a sample simultaneously using a single assay. The "nucleic acid-guided nuclease cascade assays" or "signal boost cascade assays" or "cascade assays" or "signal boost assays" described herein optionally comprise at least three different ribonucleoprotein complexes (optionally one to detect the nucleic acid target of interest, one to detect the non-nucleic acid of interest and one to provide the signal boost) and either blocked nucleic acid molecules, blocked primer molecules, or blocked guide molecules. The blocked nucleic acid molecules, blocked primer molecules, and blocked guide molecules keep the signal boosting ribonucleoprotein complexes (the second ribonucleoprotein complexes or RNP2s) "locked" unless and until a nucleic acid target of interest and/or a non-nucleic acid target of interest activates the target-detecting ribonucleoprotein complex(es). The present nucleic acid-guided nuclease cascade assay can detect one or more nucleic acid target of interest and/or non-nucleic acid targets of interest (e.g., DNA, RNA and/or cDNA) at attomolar (aM) (or lower) limits in some embodiments in a minute or less. A particularly advantageous feature of the cascade assay generally is that, with the exception of the aptamer/aptamer-complementary strand and the guide nucleic acids (gRNA1s) in the first ribonucleoprotein complexes, the cascade assay components can be the same in each assay no matter what nucleic acid target(s) of interest and non-nucleic acid target(s) of interest are being detected and guide nucleic acids are easily designed with software that is readily available online.

Thus, in a first embodiment there is provided a method for detecting one or more non-nucleic acid targets of interest in a sample comprising the steps of: providing reaction mix comprising: aptamer/aptamer-complement double-strand oligonucleotides; first ribonucleoprotein complexes (RNP1-NONs), wherein the RNP1-NONs comprise a first nucleic acid-guided nuclease and a first gRNA (gRNA1-NON); wherein the gRNA1-NONs comprise a sequence complementary to the aptamer-complement, and wherein the first nucleic acid-guided nuclease exhibits trans-cleavage activity; second ribonucleoprotein complexes (RNP2s), wherein the RNP2s comprise a second nucleic acid-guided nuclease and a second gRNA that is not complementary to the aptamer-complement, and wherein the second nucleic acid-guided nuclease exhibits trans-cleavage activity; and a plurality of blocked nucleic acid molecules comprising a sequence complementary to the second gRNA; contacting the reaction mixture with the sample under conditions that allow non-nucleic acid targets of interest in the sample to bind to the aptamer, wherein: upon binding of the aptamer to the non-nucleic acid targets of interest, the aptamer-complement is no longer hybridized to the aptamer and the aptamer-complement can bind with the RNP1-NON; upon binding of the aptamer-complement to the RNP1-NON, the RNP1-NON becomes active and trans-cleaves at least one of the blocked nucleic acid molecules, thereby producing at least one unblocked nucleic acid molecule that can complex with RNP2; and upon binding of the at least one unblocked nucleic acid molecule to the RNP2, the RNP2 becomes active and trans-cleaves at least one more of the blocked nucleic acid molecules and at least one reporter moiety in a cascade; allowing the cascade to continue; and detecting the unblocked nucleic acid molecules, thereby detecting the one or more non-nucleic acid targets of interest in the sample.

In a second embodiment there is provided a method for detecting one or more non-nucleic acid targets of interest in a sample comprising the steps of: providing reaction mix comprising: aptamer/aptamer-complement double-strand oligonucleotides; first ribonucleoprotein complexes (RNP1-NONs), wherein the RNP1-NONs comprise a first nucleic acid-guided nuclease and a first gRNA (gRNA1-NON); wherein the gRNA1-NONs comprise a sequence complementary to the aptamer-complement, and wherein the first nucleic acid-guided nuclease exhibits trans-cleavage activity; second ribonucleoprotein complexes (RNP2s) comprising a second nucleic acid-guided nuclease and a second gRNA that is not complementary to the target nucleic acid of interest; wherein the second nucleic acid-guided nuclease exhibits both cis-cleavage activity and trans-cleavage activity; a plurality of template molecules comprising sequence homology (e.g., 80%, 85%, 90%, 95%, 97% or more) to the second gRNA; a plurality of blocked primer molecules comprising a sequence complementary to the template molecules, wherein the blocked nucleic acid molecules cannot be extended by a polymerase; and a polymerase and a plurality of nucleotides; contacting the reaction mixture with the sample under conditions that allow non-nucleic acid targets of interest in the sample to bind to the aptamer, wherein: upon binding of the aptamer to the non-nucleic acid targets of interest, the aptamer-complement is no longer hybridized to the aptamer and the aptamer-complement can bind with the RNP1-NON; upon binding of the aptamer-complement to the RNP1-NON, the RNP1-NON becomes active and trans-cleaves at least one of the blocked primer molecules, thereby producing at least one unblocked primer molecule that can be extended by the polymerase; the at least one unblocked primer molecule binds to one of the template molecules and is extended by the polymerase and the plurality of nucleotides to form at least one synthesized activating molecule having a sequence complementary to the second gRNA; and the at least one synthesized activating molecule binds to the second gRNA, and RNP2 becomes active and cleaves at least one further blocked primer molecule and at least one reporter moiety in a cascade; allowing the cascade to continue; and detecting the unblocked primer molecules, thereby detecting the one or more non-nucleic acid targets of interest in the sample.

In a third embodiment there is provided a method for detecting one or more non-nucleic acid targets of interest in a sample comprising the steps of: providing reaction mix comprising: aptamer/aptamer-complement double-strand oligonucleotides; first ribonucleoprotein complexes (RNP1-NONs), wherein the RNP1-NONs comprise a first nucleic acid-guided nuclease and a first gRNA (gRNA1-NON); wherein the gRNA1-NONs comprise a sequence complementary to the aptamer-complement, and wherein the first nucleic acid-guided nuclease exhibits trans-cleavage activity; second nucleic acid-guided nucleases, wherein the second nucleic acid-guided nuclease exhibits both cis- and trans-cleavage activity; RNP2 activating nucleic acids; and a plurality of blocked guide molecules comprising a sequence complementary to the RNP2 activating nucleic acids; contacting the reaction mixture with the sample under conditions that allow non-nucleic acid targets of interest in the sample to bind to the aptamer, wherein: upon binding of the aptamer to the non-nucleic acid targets of interest, the aptamer-complement is no longer hybridized to the aptamer and the aptamer-complement can bind with the RNP1-NON; upon binding of the aptamer-complement to the RNP1, the RNP1 becomes active and trans-cleaves at least one of the blocked guide molecules, thereby producing at least one unblocked guide molecule that can complex with the second nucleic acid-guided nuclease to form RNP2; the RNP2 binds to RNP2 activating nucleic acids and becomes active and trans-cleaves at least one more of the blocked guide molecules and at least one reporter moiety in a cascade; allowing the cascade to continue; and detecting the reporter moieties, thereby detecting the one or more non-nucleic acid targets of interest in the sample.

In any one of the preceding three embodiments, instead of aptamer/aptamer-complement double-strand oligonucleotides, aptamer/masked molecule compound molecules are provided; where the aptamer/masked molecule compounds comprise an aptamer region and a masked molecule region; where the masked molecule region comprises a target strand and a non-target strand; where the gRNA1-NONs comprise a gRNA sequence complementary to the target strand of the masked molecule region of the aptamer/masked molecule compound molecules; where upon binding of the aptamer region of the aptamer/masked molecule compound molecules to the non-nucleic acid targets of interest, the aptamer/masked molecule compound molecules are reconfigured, unmasking the masked molecule region of the aptamer/masked molecule compound molecules and freeing the target strand to bind with the RNP1-NON; and where upon binding of the target strand to the RNP1-NON, the RNP1-NON becomes active and trans-cleaves at least one of the blocked nucleic acid molecules, blocked primer molecules or blocked guide molecules thereby producing at least one unblocked nucleic acid molecule, unblocked primer molecule or unblocked guide molecule. The unblocked nucleic acid molecule and unblocked guide molecule can complex with RNP2. The unblocked primer molecule can bind to the template molecule and be extended by the polymerase to form a synthesized activating molecule that can complex with RNP2.

In any of the preceding embodiments, the reaction mix further may further comprise reporter moieties, wherein the reporter moieties produce a detectable signal upon trans-cleavage activity by the RNP1-NON and/or RNP2 to identify the presence of one or more non-nucleic acid targets of interest in the sample.

In any of the preceding embodiments, the aptamer may be a riboswitch and where the riboswitch comprises an aptamer domain to an effector molecule of choice and an expression platform domain heterologous to the aptamer domain, and in some aspects, the expression platform domain is selected from an expression platform from a cobalamin riboswitch, a cyclic AMP-GMP riboswitch, a cyclic di-AMP riboswitch, a cylic di-GMP riboswitch, a fluoride riboswitch, a Flavin mononucleotide (FMN) riboswitch, a glmS (glucose-6-phosphate) riboswitch, a Glutamine riboswitch, a Glycine riboswitch, a Lysine riboswitch, a manganese riboswitch, a NiCo riboswitch, a PreQ1 (pre-queuosine 1) riboswitch, a purine riboswitch, an SAH (S-adenosylhomocysteine) riboswitch, an SAM (S-adenosyl methionine) riboswitch, an SAM-SAH (recognizes both S-adenosylhomocysteine and S-adenosyl methionine) riboswitch, a tetrahdrofolate riboswitch, a thyamine pyrophosphate (TPP) (which is involved in thiamin biosynthesis—and found in eukaryotes) riboswitch, and a SMP.STP riboswitch.

In some aspects of these embodiments, one or both of RNP1-NON and RNP2 comprises a nucleic acid-guided nuclease selected from Cas3, Cas12a, Cas12b, Cas12c, Cas12d, Cas12e, Cas14, Cas12h, Cas12i, Cas12j, Cas13a, or Cas13b, and in some aspects, one or both of RNP1-NON and RNP2 comprises a nucleic acid-guided nuclease that is a Type V nucleic acid-guided nuclease or a Type VI nucleic acid-guided nuclease.

In embodiments employing blocked nucleic acid molecules or blocked primer molecules, the blocked nucleic acid molecules or blocked primer molecules comprise a structure represented by any one of Formulas I-IV, wherein Formulas I-IV are in the 5'-to-3' direction:
  (a) A-(B-L)$_J$-C-M-T-D (Formula I);
  wherein A is 0-15 nucleotides in length;
  B is 4-12 nucleotides in length;
  L is 3-25 nucleotides in length;
  J is an integer between 1 and 10;
  C is 4-15 nucleotides in length;
  M is 1-25 nucleotides in length or is absent, wherein if M is absent then A-(B-L)$_J$-C and T-D are separate nucleic acid strands;
  T is 17-135 nucleotides in length and comprises at least 50% sequence complementarity to B and C; and
  D is 0-10 nucleotides in length and comprises at least 50% sequence complementarity to A;
  and wherein segment A may be attached to segment D forming a loop;
  (b) D-T-T'-C-(L-B)$_J$-A (Formula II);
  wherein D is 0-10 nucleotides in length;
  T-T' is 17-135 nucleotides in length;
  T' is 1-10 nucleotides in length and does not hybridize with T;
  C is 4-15 nucleotides in length and comprises at least 50% sequence complementarity to T;
  L is 3-25 nucleotides in length and does not hybridize with T;
  B is 4-12 nucleotides in length and comprises at least 50% sequence complementarity to T;
  J is an integer between 1 and 10;
  A is 0-15 nucleotides in length and comprises at least 50% sequence complementarity to D;
  and wherein segment T is attached to segment B forming a loop;
  (c) T-D-M-A-(B-L)$_J$-C (Formula III);
  wherein T is 17-135 nucleotides in length;
  D is 0-10 nucleotides in length;
  M is 1-25 nucleotides in length or is absent, wherein if M is absent then T-D and A-(B-L)$_J$-C are separate nucleic acid strands;
  A is 0-15 nucleotides in length and comprises at least 50% sequence complementarity to D;
  B is 4-12 nucleotides in length and comprises at least 50% sequence complementarity to T;
  L is 3-25 nucleotides in length;
  J is an integer between 1 and 10; and
  C is 4-15 nucleotides in length;
  and wherein segment T is attached to segment C forming a loop; or
  (d) T-D-M-A-L$_p$-C (Formula IV);
  wherein T is 17-31 nucleotides in length;
  D is 0-15 nucleotides in length;
  M is 1-25 nucleotides in length;
  A is 0-15 nucleotides in length and comprises a sequence complementary to D; and L is 3-25 nucleotides in length;
  p is 0 or 1;
  C is 4-15 nucleotides in length and comprises a sequence complementary to T.

In some aspects:
  (a) T of Formula I comprises at least 80% sequence complementarity to B and C;
  (b) D of Formula I comprises at least 80% sequence complementarity to A;
  (c) C of Formula II comprises at least 80% sequence complementarity to T;
  (d) B of Formula II comprises at least 80% sequence complementarity to T;
  (e) A of Formula II comprises at least 80% sequence complementarity to D;
  (f) A of Formula III comprises at least 80% sequence complementarity to D;
  (g) B of Formula III comprises at least 80% sequence complementarity to T;
  (h) A of Formula IV comprises at least 80% sequence complementarity to D; and/or
  (i) C of Formula IV comprises at least 80% sequence complementarity to T.

In some aspects of these embodiments, the blocked nucleic acid molecule, blocked primer molecule or blocked guide molecule may comprise a modified nucleoside or nucleotide, and in some aspects, the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

In some aspects of these embodiments, there are at least ten (e.g., ten, eleven, twelve, thirteen, fourteen, or more) different RNP1-NONs in the reaction mix, and in some aspects, there are at least fifteen, twenty, twenty-five, thirty, forty, fifty, sixty, seventy, eighty, ninety, one hundred, one hundred fifty, two hundred, three hundred, four hundred, five hundred or more different RNP1-NONs in the reaction mix. In some aspects, several to many to a massively multiplexed number of different non-nucleic acid targets are targeted, and in some aspects, several to many to a large number of epitopes of a single non-nucleic acid target is targeted. In some aspects, both different non-nucleic acid targets and epitopes of a single non-nucleic acid target are targeted.

In some aspects the embodiments further comprise the steps of: providing third ribonucleoprotein complexes (RNP1-NAs), wherein the RNP1-NAs comprise a third nucleic acid-guided nuclease and a third gRNA (gRNA1-NA); wherein the gRNA1-NA comprises a sequence complementary to a nucleic acid target of interest, and wherein the third nucleic acid-guided nuclease exhibits trans-cleavage activity; contacting the reaction mixture with the sample under conditions that allow nucleic acid targets of interest in the sample to bind the RNP1-NA, wherein: upon binding of the nucleic acid target to the RNP1-NA, the RNP1-NA becomes active and trans-cleaves at least one of the blocked nucleic acid molecules or blocked primer molecules or blocked guide molecules, thereby producing at least one unblocked nucleic acid molecule or unblocked primer molecule or unblocked guide molecule that can complex with RNP2; and upon binding of the at least one unblocked nucleic acid molecule to RNP2, or the at least one unblocked primer molecule to the template strand and subsequent activating molecule to RNP2, or the at least one unblocked guide molecule to the RNP2, the RNP2 becomes active and trans-cleaves at least one more of the blocked nucleic acid molecules or blocked primer molecules or blocked guide molecule and at least one reporter moiety in a cascade; allowing the cascade to continue; and detecting the unblocked nucleic acid molecules or unblocked primer molecules or unblocked guide molecules, thereby detecting the target nucleic acid of interest in the sample.

As with the other embodiments, in this embodiment the reaction mix may comprise reporter moieties, wherein the reporter moieties produce a detectable signal upon trans-cleavage activity by the RNP1-NONs, RNP1-NAs and/or RNP2s to identify the presence of one or more non-nucleic acid targets of interest in the sample.

In yet another embodiment there are presented reaction mixes comprising aptamer/aptamer-complement double-strand oligonucleotides; first ribonucleoprotein complexes (RNP1-NONs), wherein the RNP1-NONs comprise a first nucleic acid-guided nuclease and a guide nucleic acid (gRNA1-NON); wherein the gRNA1-NON comprises a sequence complementary to the aptamer-complement, and wherein the first nucleic acid-guided nuclease exhibits trans-cleavage activity; second ribonucleoprotein complexes (RNP2s), wherein the RNP2s comprise a second nucleic acid-guided nuclease and a second gRNA that is not complementary to the aptamer-complement, and wherein the second nucleic acid-guided nuclease exhibits trans-cleavage activity; and a plurality of blocked nucleic acid molecules comprising a sequence complementary to the second gRNA.

Alternatively, there is presented a reaction mix comprising aptamer/aptamer-complement double-strand oligonucleotides; first ribonucleoprotein complexes (RNP1-NONs), wherein the RNP1-NONs comprise a first nucleic acid-guided nuclease and a first gRNA (gRNA1-NON); wherein the gRNA1-NONs comprise a sequence complementary to the aptamer-complement, and wherein the first nucleic acid-guided nuclease exhibits trans-cleavage activity; second ribonucleoprotein complexes (RNP2s) comprising a second nucleic acid-guided nuclease and a second gRNA that is not complementary to the target nucleic acid of interest; wherein the second nucleic acid-guided nuclease exhibits both cis-cleavage activity and trans-cleavage activity; a plurality of template molecules comprising sequence homology to the second gRNA; a plurality of blocked primer molecules comprising a sequence complementary to the template molecules, wherein the blocked nucleic acid molecules cannot be extended by a polymerase; and a polymerase and a plurality of nucleotides.

Also provided is a reaction mixture comprising: aptamer/aptamer-complement double-strand oligonucleotides; first ribonucleoprotein complexes (RNP1-NONs), wherein the RNP1-NONs comprise a first nucleic acid-guided nuclease and a first gRNA (gRNA1-NON); wherein the gRNA1-NONs comprise a sequence complementary to the aptamer-complement, and wherein the first nucleic acid-guided nuclease exhibits trans-cleavage activity; second nucleic acid-guided nucleases, wherein the second nucleic acid-guided nuclease exhibits both cis- and trans-cleavage activity; RNP2 activating nucleic acids; and a plurality of blocked guide molecules comprising a sequence complementary to the RNP2 activating nucleic acids.

In any one of the preceding three reaction mix embodiments, instead of aptamer/aptamer-complement double-strand oligonucleotides, aptamer/masked molecule compound molecules are provided; where the aptamer/masked molecule compounds comprise an aptamer region and a masked molecule region; where the masked molecule region comprises a target strand and a non-target strand; where the gRNA1-NONs comprise a sequence complementary to the target strand of the masked molecule region of the aptamer/masked molecule compound molecules.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 2B shows the pbuE riboswitch of *Bacillus subtilis* (SEQ ID NO: 9) in both an "on" and "off" state; FIG. 2C shows the add riboswitch of *Vibrio vulnificus* (SEQ ID NO: 10) in both an "on" and "off" state.

FIG. 8B is a graphic representation of the multiplexed cascade assay workflow embodiment shown in FIG. 7. FIG. 8B-1 comprises steps 702+704 from FIG. 7, designing gRNA1-1 and gRNA1-2 pairs and forming RNP1-1/RNP1-2s; FIG. 8B-2 comprises step 708 from FIG. 7, combining the sample and dual RNP1-1/RNP1-2s; FIG. 8B-3 comprises step 710 from FIG. 7, designing and synthesizing an oligonucleotide array with oligonucleotide sequences complementary to the gRNA1-2s at known coordinates; and FIG. 8B-4 comprises step 712 from FIG. 7, introducing the sample and dual RNP1-1/RNP1-2s to the oligonucleotide array.

It should be understood that the drawings are not necessarily to scale, and that like reference numbers refer to like features.

Definitions

Figure 1:
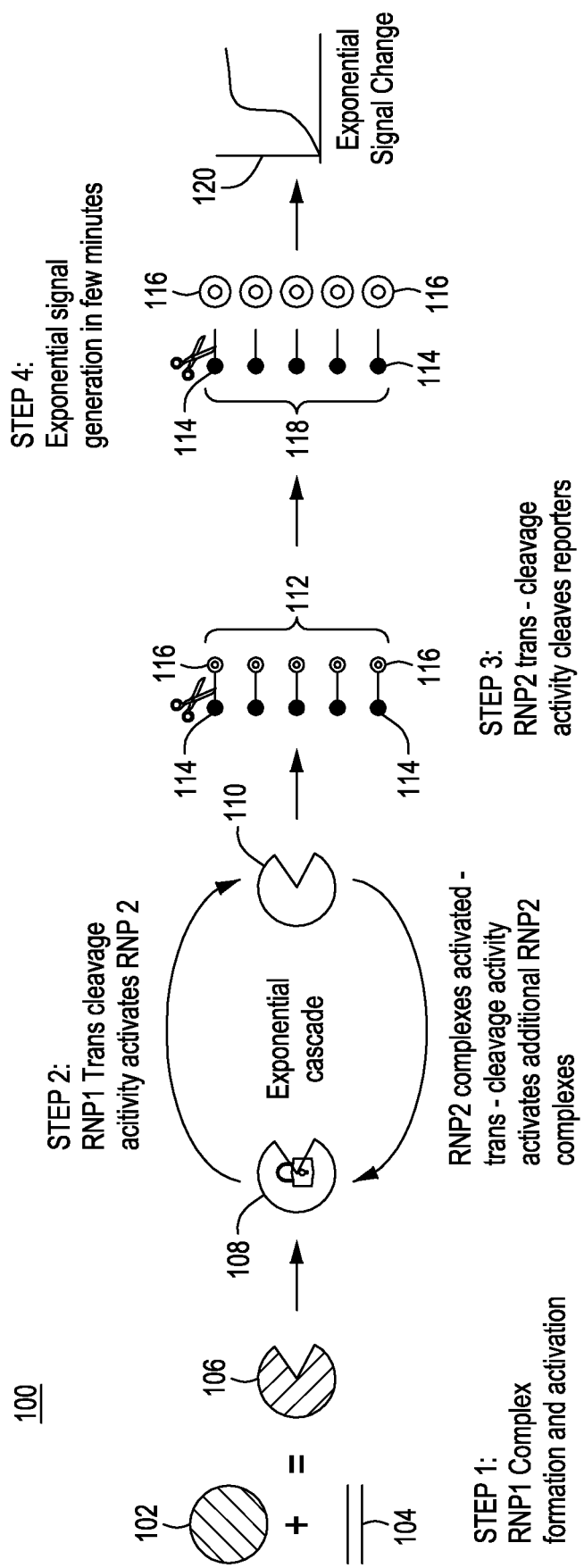
FIG. 1 is an overview of the general principles underlying the nucleic acid-guided nuclease signal boost cascade assay described in detail herein.

All of the functionalities described in connection with one embodiment of the compositions and/or methods described herein are intended to be applicable to the additional embodiments of the compositions and/or methods except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "a system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention. Conventional methods are used for the procedures described herein, such as those provided in the art, and demonstrated in the Examples and various general references. Unless otherwise stated, nucleic acid sequences described herein are given, when read from left to right, in the 5' to 3' direction. Nucleic acid sequences may be provided as DNA, as RNA, or a combination of DNA and RNA (e.g., a chimeric nucleic acid).

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

As used herein, the term "about," as applied to one or more values of interest, refers to a value that falls within 10%, 9%, 8%, 7%, 6%, 5%, 4%, 3%, 2%, 1%, or less in either direction (greater than or less than) of a stated reference value, unless otherwise stated or otherwise evident from the context (except where such number would exceed 100% of a possible value).

As used herein, the terms "activating nucleic acid" or "activating molecule" generally refer to both RNP2 activating nucleic acids and synthesized activating nucleic acids. "RNP2 activating nucleic acids" refer to nucleic acid molecules that complex with RNP2 and activate cis- and trans-cleavage of RNP2 in the blocked guide nucleic acid embodiment of the cascade assay described below. "Synthesized activating nucleic acid" or "synthesized activating molecule" refer to the nucleic acid molecules that complex with RNP2 and activate cis- and trans-cleavage of RNP2 in the blocked primer molecule embodiments of the cascade assay described below.

As used herein, the term "aptamer" refers to nucleic acid oligonucleotides that bind to proteins or other non-nucleic acid molecules with specificity and affinity. "Aptamer-complement" refers to an oligonucleotide complementary to an aptamer.

As used herein, an "aptamer/masked molecule compound molecule" comprises an aptamer region and a masked molecule region, and a masked molecule region comprises a target strand and a non-target strand. When an aptamer region binds a non-nucleic acid target, the aptamer/masked molecule compound molecule changes conformation freeing the target strand of the masked molecule region; that is, unmasking the masked molecule region of the aptamer/masked molecule compound molecule.

As used herein, the terms "binding affinity" or "dissociation constant" or "$K_d$" refer to the tendency of a molecule to bind (covalently or non-covalently) to a different molecule. A high $K_d$ (which in the context of the present disclosure refers to blocked nucleic acid molecules, blocked primer molecules, or blocked guide nucleic acids (blocked gRNA2s)) indicates the presence of more unbound molecules, and a low $K_d$ (which in the context of the present disclosure refers to unblocked nucleic acid molecules binding to RNP2s, or unblocked primer molecules binding to template molecules, or unblocked guide nucleic acids (unblocked gRNA2s) binding to RNP2 activating nucleic acids) indicates the presence of more bound molecules. In the context of the present disclosure and the binding of blocked or unblocked nucleic acid molecules to RNP2, low $K_d$ values are in a range from about 100 fM to about 1 aM or lower (e.g., 100 zM) and high $K_d$ values are in the range of 100 nM-100 μM (10 mM) and thus are about $10^5$- to $10^{10}$-fold or higher as compared to low $K_d$ values. In the context of the present disclosure and the binding of blocked or unblocked guide nucleic acids to RNP2 activating nucleic acids, low $K_d$ values are typically in a range from about 1 nM to about 10 nM or lower, or any range between about 1 nM to about 10 nM. High $K_d$ values can be about 10, 100 or 100 or more times higher as compared to low $K_d$ values.

As used herein, the terms "binding domain" or "binding site" refer to a region on a protein, DNA, or RNA, to which specific molecules and/or ions (ligands) may form a covalent or non-covalent bond. By way of example, a polynucleotide sequence present on a nucleic acid molecule (e.g., a primer binding domain) may serve as a binding domain for a different nucleic acid molecule (e.g., an unblocked primer nucleic acid molecule). Characteristics of binding sites are chemical specificity, a measure of the types of ligands that will bond, and affinity, which is a measure of the strength of the chemical bond.

As used herein, the terms "blocked guide molecule", "blocked guide nucleic acid", "blocked guide RNA", "blocked gRNA2" and "blocked gRNA" refer to CRISPR guide nucleic acids that cannot bind to the first or second RNP complex to activate cis- or trans-cleavage. The terms "unblocked guide molecule", "unblocked guide nucleic acid", "unblocked guide RNA", "unblocked gRNA2" and "unblocked gRNA" refer to a formerly blocked gRNA that can form the second RNP complex (RNP2) and bind to RNP2 activating nucleic acids to activate trans-cleavage of additional blocked gRNAs.

As used herein, the term "blocked nucleic acid molecule" refers to nucleic acid molecules that cannot bind to the first or second RNP complex to activate cis- or trans-cleavage. "Unblocked nucleic acid molecule" refers to a formerly blocked nucleic acid molecule that can bind to the second RNP complex (RNP2) to activate trans-cleavage of additional blocked nucleic acid molecules. A "blocked nucleic acid molecule" may be a "blocked primer molecule" in some embodiments of the cascade assay. In the case of blocked primer molecules, "unblocked primer molecules" prime a template molecule for the synthesis (e.g., via a polymerase) of synthesized activating nucleic acids that can bind to RNP2 to activate trans-cleavage of additional blocked primer molecules.

The terms "Cas RNA-guided endonuclease" or "CRISPR nuclease" or "nucleic acid-guided nuclease" refer to a CRISPR-associated protein that is an RNA-guided endonuclease suitable for assembly with a sequence-specific gRNA to form a ribonucleoprotein (RNP) complex.

As used herein, the terms "cis-cleavage", "cis-endonuclease activity", "cis-mediated endonuclease activity", "cis-nuclease activity", "cis-mediated nuclease activity", and variations thereof refer to sequence-specific cleavage of a nucleic acid target of interest or aptamer-complement, including an unblocked nucleic acid molecule or synthesized activating nucleic acid, by a nucleic acid-guided nuclease in an RNP complex. Cis-cleavage is a single turn-over cleavage event in that only one substrate molecule is cleaved per event.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10, or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-ATCGAT-5' is 100% complementary to a region of the nucleotide sequence 5'-GCTAGCTAG-3'.

As used herein, the term "contacting" refers to placement of two moieties in direct physical association, including in solid or liquid form. Contacting can occur in vitro with isolated cells (for example in a tissue culture dish or other vessel) or in samples or in vivo by administering an agent to a subject.

A "control" is a reference standard of a known value or range of values.

The terms "guide nucleic acid" or "guide RNA" or "gRNA" refer to a polynucleotide comprising 1) a crRNA region or guide sequence capable of hybridizing to the target strand of a nucleic acid target of interest (or aptamer-complement), and 2) a scaffold sequence capable of interacting or complexing with a nucleic acid-guided nuclease. The crRNA region of the gRNA is a customizable component that enables specificity in every nucleic acid-guided nuclease reaction. A gRNA can include any polynucleotide sequence having sufficient complementarity with a nucleic acid target of interest to hybridize with the nucleic acid target of interest and to direct sequence-specific binding of a ribonucleoprotein (RNP) complex containing the gRNA and nucleic acid-guided nuclease to the nucleic acid target. Nucleic acid targets of interest may include a protospacer adjacent motif (PAM), and, following gRNA binding, the nucleic acid-guided nuclease induces a double-stranded break either inside or outside the protospacer region on the nucleic acid target of interest, including on an unblocked nucleic acid molecule or synthesized activating nucleic acid. A gRNA may contain a spacer sequence including a plurality of bases complementary to a protospacer sequence in the nucleic acid target. For example, a spacer can contain about 2, 3, 4, 5, 6, 7, 8, 9, 10, 11, 12, 13, 14, 15, 20, 25, 30, 35, 40, 45, 50, 55, 60, or more bases. The gRNA spacer may be 50%, 60%, 75%, 80%, 85%, 90%, 95%, 97.5%, 98%, 99%, or more complementary to its corresponding nucleic acid target of interest. Optimal alignment may be determined with the use of any suitable algorithm for aligning sequences. A guide RNA may be from about 20 nucleotides to about 300 nucleotides long. Guide RNAs may be produced synthetically or generated from a DNA template.

"Modified" refers to a changed state or structure of a molecule. Molecules may be modified in many ways including chemically, structurally, and functionally. In one embodiment, a nucleic acid molecule (for example, a blocked nucleic acid molecule) may be modified by the introduction of non-natural nucleosides, nucleotides, and/or internucleoside linkages. In another embodiment, a modified protein (e.g., a nucleic acid-guided nuclease) may refer to any polypeptide sequence alteration which is different from the wildtype.

The terms "nucleic acid target of interest", "nucleic acid target sequence", "nucleic acid target", "target nucleic acid", "target nucleic acid molecule" or "nucleic acid target molecule of interest" refer to a nucleic acid molecule that is being assayed for in the signal boost assays described herein. These terms may also refer to an aptamer-complement, which is the proxy for a non-nucleic acid target of interest.

The terms "non-nucleic acid target", "non-nucleic acid target sequence", "non-nucleic acid target of interest" or "non-nucleic acid target molecule of interest" refer to a non-nucleic acid molecule (e.g., a polypeptide) that can specifically bind to an aptamer. The terms "target molecules", "targets of interest", or "target molecules of interest" refer to both nucleic acid targets of interest and non-nucleic acid targets of interest.

As used herein, a "partition" is an isolate region (e.g., a feature surrounded by an interstitial region) or an isolate depression (e.g., a well) on a substrate, or a droplet.

The terms "percent sequence identity", "percent identity", or "sequence identity" refer to percent (%) sequence identity with respect to a reference polynucleotide or polypeptide sequence following alignment by standard techniques. Alignment for purposes of determining percent sequence identity can be achieved in various ways that are within the capabilities of one of skill in the art, for example, using publicly available computer software such as BLAST, BLAST-2, PSI-BLAST, or Megalign software. In some embodiments, the software is MUSCLE (Edgar, Nucleic Acids Res., 32(5):1792-1797 (2004)). Those skilled in the art can determine appropriate parameters for aligning sequences, including any algorithms needed to achieve maximal alignment over the full length of the sequences being compared. For example, in embodiments, percent sequence identity values are generated using the sequence comparison computer program BLAST (Altschul, et al., J. Mol. Biol., 215:403-410 (1990)).

As used herein, the terms "preassembled ribonucleoprotein complex", "ribonucleoprotein complex", "RNP complex", or "RNP" refer to a complex containing a guide RNA (gRNA) and a nucleic acid-guided nuclease, where the gRNA is integrated with the nucleic acid-guided nuclease. The gRNA, which includes a sequence complementary to a nucleic acid target of interest, guides the RNP to the nucleic acid target of interest and hybridizes to it. The hybridized nucleic acid target-gRNA units are cleaved by the nucleic acid-guided nuclease. In the cascade assays described herein, a first ribonucleoprotein complex (RNP1) includes a first guide RNA (gRNA1) specific to a nucleic acid target of interest or aptamer-complement and a first nucleic acid-guided nuclease, such as, for example, cas12a or cas14a for a DNA nucleic acid target, or cas13a for an RNA nucleic acid target. A second ribonucleoprotein complex (RNP2) for signal amplification includes a second guide RNA (gRNA2) specific to an unblocked nucleic acid (or, depending on the cascade assay embodiment, a synthesized activating nucleic acid or an RNA2 activating nucleic acid) and a second nucleic acid-guided nuclease.

As used herein, the terms "protein" and "polypeptide" are used interchangeably. Proteins may or may not be made up entirely of amino acids.

As used herein, the term "sample" refers to tissues; cells or component parts; body fluids, including but not limited to peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. "Sample" may also refer to specimen or aliquots from food; agricultural products; pharmaceuticals; cosmetics, nutraceuticals; personal care products; environmental substances such as soil, water, air, or sewer sample; industrial sites and products; and chemicals and compounds. A sample further may include a homogenate, lysate or extract.

As used herein, the terms "trans-cleavage", "trans-endonuclease activity", "trans-mediated endonuclease activity", "trans-nuclease activity", "trans-mediated nuclease activity" and variations thereof refer to indiscriminate, non-sequence-specific cleavage of a nucleic acid molecule by an endonuclease (such as by a Cas12, Cas13, and Cas14).

Type V CRISPR/Cas nucleic acid-guided nucleases are a subtype of Class 2 CRISPR/Cas effector nucleases such as, but not limited to, engineered Cas12a, Cas12b, Cas12c, C2c4, C2c8, C2c5, C2c10, C2c9, CasX (Cas12e), CasY (Cas12d), Cas 13a nucleases or naturally-occurring proteins, such as a Cas12a isolated from, for example, *Francisella tularensis* subsp. *novicida* (Gene ID: 60806594), Candidatus Methanoplasma *termitum* (Gene ID: 24818655), Candidatus Methanomethylophilus alvus (Gene ID: 15139718), and [*Eubacterium*] eligens ATCC 27750 (Gene ID: 41356122), and artificial polypeptides, such as a chimeric protein.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like.

DETAILED DESCRIPTION

The present disclosure provides compositions of matter and signal boost cascade assay methods for detecting nucleic acid targets and non-nucleic acid targets of interest simultaneously using a single CRISPR-based assay. The compositions and methods provide for massive multiplexing, high accuracy, low cost, minimum workflow, with results in some embodiments virtually instantaneously, even at ambient temperatures of 20-25° C. or less. The cascade assays described herein may comprise at least three different ribonucleoprotein complexes (one to detect the nucleic acid target of interest, one to detect the non-nucleic acid of interest and one to provide the signal boost) and either blocked nucleic acid molecules, blocked primer molecules, or blocked guide nucleic acids. The first ribonucleoprotein complexes detect nucleic acid targets of interest and/or non-nucleic acid targets of interest and the second ribonucleoprotein complexes provide the signal boost. The blocked nucleic acid molecules, blocked primer molecules, and blocked guide nucleic acids keep the second ribonucleoprotein complexes "locked" unless and until a nucleic acid target of interest and/or non-nucleic acid target of interest activates the first ribonucleoprotein complex. The methods comprise the steps of providing signal boost cascade assay components, contacting the signal boost cascade assay components with a sample, and detecting a signal that is generated only when a nucleic acid target of interest and/or non-nucleic acid target of interest is present in the sample.

Early and accurate identification of, e.g., infectious agents, contamination by heterologous sources, detection of metals, and variant proteins that indicate the presence of such diseases such as cancer is important in order to select correct treatment; identify tainted food, pharmaceuticals, cosmetics and other commercial goods; and to monitor the environment. However, currently available state-of-the-art nucleic acid target detection typically relies on assays that require amplification of nucleic acids in a sample (via the polymerase chain reaction or PCR), where PCR requires time and may lead to changes to the relative proportion of nucleic acids, particularly in multiplexed nucleic acid assays. Currently available non-nucleic acid target detection typically relies on use of antibodies or physical or chemical sensors, and more recently, on aptamers. Although aptamers recognize and bind non-nucleic acid targets of interest like antibodies do, aptamers have many advantages over antibodies. For example, aptamers are more easily and cheaply manufactured than antibodies, are able to withstand repeated rounds of denaturation and renaturation, are temperature resistant (e.g., stable at room temperature), have little batch to batch variation, and have a long shelf life. In addition, selection of aptamers via SELEX (Systematic Evolution of Ligands by Exponential Enrichment) takes only 2-8 weeks, whereas antibodies are produced in vivo via a laborious and expensive process that typically takes more than 6 months. Likewise, sensors are laborious to develop, being limited in their range of targets and sensors also involve complex synthesis processes. Another advantage of aptamers is that they can be easily modified without affinity loss.

The present disclosure describes a signal boost cascade assay and improvements thereto that can detect one or many nucleic acid targets of interest and non-nucleic acid targets of interest at attamolar (aM) (or lower) limits. As described in detail below, the cascade assays utilize signal boost mechanisms comprising various components including nucleic acid-guided nucleases; guide RNAs (gRNAs) incorporated into ribonucleoprotein complexes (RNP complexes); blocked nucleic acid molecules, blocked primer molecules, or blocked guide nucleic acids; reporter moieties, and, in some embodiments, polymerases and template molecules, or RNP2 activating nucleic acids. A particularly advantageous feature of the cascade assay is that, with the exception of the gRNAs (gRNA1) in the RNP1s and the aptamer/aptamer-complement double-stranded oligonucleotide, the cascade assay components can be essentially identical no matter what targets of interest are being detected, and the aptamer/aptamer-complement and gRNA1s are easily programmable.

FIG. 1 provides a simplified diagram demonstrating method 100 of a signal boost cascade assay. The cascade assay is initiated when a nucleic acid target of interest or a aptamer-complement 104 binds to and activates a first pre-assembled ribonucleoprotein complex (RNP1) 102. The first ribonucleoprotein complex (RNP1) comprises a first guide RNA (gRNA1) and a nucleic acid-guided nuclease, where the gRNA is integrated with the nucleic acid-guided nuclease. The gRNA1, which includes a sequence complementary to the nucleic acid target of interest (or an aptamer-complement), guides RNP1 to the nucleic acid target of interest (or aptamer-complement) and hybridizes to it. Typically, preassembled RNP complexes are employed in the reaction mixture—as opposed to separate nucleic acid-guided nucleases and gRNAs—to facilitate rapid (often virtually instantaneous) detection of the nucleic acid target(s) and/or non-nucleic acid target(s) of interest, if desired.

"Activation" of RNP1 in the context of the cascade assay refers to activating trans-cleavage activity of the nucleic acid-guided nuclease in RNP1 106 by binding of the nucleic acid target of interest (or aptamer-complement) to the gRNA in RNP1 or by initiating cis-cleavage of the nucleic acid target of interest (or aptamer-complement) 104 by the nucleic acid-guided nuclease. This binding and cis-cleavage activity then initiates trans-cleavage activity (i.e., multi-turnover activity) of the nucleic acid-guided nuclease, where trans-cleavage is indiscriminate and leads to non-sequence-specific cutting of nucleic acid molecules by the nucleic acid-guided nuclease of RNP1 106. This trans-cleavage activity triggers activation of second ribonucleoprotein complexes (RNP2s) 108 via unblocked nucleic acid molecules that were formerly blocked nucleic acid molecules (or in alternative embodiments, blocked primer molecules or blocked guide nucleic acids), all of which are described in detail below. Each newly activated RNP2 110 activates more RNP2s 108→110, which in turn cleave reporter moieties 112. The reporter moieties 112 may be a synthetic molecule linked or conjugated to a quencher 114 and a fluorophore 116 such as, for example, a probe with a dye label (e.g., FAM or FITC) on the 5' end and a quencher on the 3' end. The quencher 114 and fluorophore 116 can be about 20-30 bases apart or less for effective quenching via fluorescence resonance energy transfer (FRET). Reporter moieties may also be incorporated into blocked nucleic acid molecules or blocked primer molecules or blocked guide nucleic acids which also affects the kinetics of the cascade assay reaction.

As more RNP2s are activated 108→110, more trans-cleavage activity is activated and more reporter moieties are unquenched; thus, the binding of the nucleic acid target of interest or non-nucleic acid of interest 104 to RNP1 102 initiates what becomes a cascade of signal production 120, which increases exponentially, hence, the term signal boost assay. The cascade assay thus comprises a single turnover event that triggers a multi-turnover event that then triggers another multi-turnover event. As described below in relation to FIG. 6, the reporter moieties 112 may be provided as molecules that are separate from the other components of the nucleic acid-guided nuclease cascade assay, or the reporter moieties may be covalently or non-covalently linked to the blocked nucleic acid molecules, blocked primer molecules, blocked guide nucleic acids, synthesized activating nucleic acids or RNP2 activation nucleic acids (i.e., the target molecules for the RNP2).

Nucleic Acid and Non-Nucleic Acid Targets of Interest

The nucleic acid target(s) of interest may be a DNA, RNA, or cDNA molecule. Nucleic acid target(s) of interest may be isolated from a sample by standard laboratory techniques. The nucleic acid targets of interest originate from source organisms that are present in a sample, such as a biological sample from a subject (including non-human animals or plants), items of manufacture, or an environmental sample (e.g., water or soil). Non-limiting examples of biological samples include blood, serum, plasma, saliva, mucus, a nasal swab, a buccal swab, a cell, a cell culture, and tissue. The source of the sample could be any mammal, such as, but not limited to, a human, primate, monkey, cat, dog, mouse, pig, cow, horse, sheep, and bat. Samples may also be obtained from any other source, such as air, water, soil, surfaces, food, beverages, nutraceuticals, clinical sites or products, industrial sites (including food processing sites) and products, plants and grains, cosmetics, personal care products, pharmaceuticals, medical devices, agricultural equipment and sites, and commercial samples.

The non-nucleic acid targets of interest may be proteins, small molecules, ions, metals, whole cells, glycoproteins, lipids, organic compounds, sugars, amino acids and small peptides, modified amino acids within proteins, and peptides. In some embodiments, the non-nucleic acid target of interest like the nucleic acid target of interest is from an infectious agent (e.g., a bacteria, protozoan, insect, worm, virus, or fungus) that affects mammals.

As a non-limiting example, the nucleic acid targets of interest and/or the non-nucleic acid targets of interest may be one or more proteins from bacteria, such as *Bordetella parapertussis, Bordetella pertussis, Chlamydia pneumoniae, Legionella pneumophila, Mycoplasma pneumoniae, Acinetobacter calcoaceticus-baumannii* complex, *Bacteroides fragilis, Enterobacter cloacae* complex, *Escherichia coli, Klebsiella aerogenes, Klebsiella oxytoca, Klebsiella pneumoniae* group, *Moraxella catarrhalis, Proteus* spp., *Salmonella enterica, Serratia marcescens, Haemophilus influenzae, Neisseria meningitidis, Pseudomonas aeruginosa, Stenotrophomonas maltophilia, Enterococcus faecalis, Enterococcus faecium, Listeria monocytogenes, Staphylococcus aureus, Staphylococcus epidermidis, Staphylococcus lugdunensis, Streptococcus agalactiae, Streptococcus pneumoniae, Streptococcus pyogenes, Chlamydia tracomatis, Neisseria gonorrhoeae,* Syphilis (*Treponema pallidum*), *Ureaplasma urealyticum, Mycoplasma genitalium,* and/or *Gardnerella vaginalis.* As a non-limiting example, the targets of interest (both nucleic acid targets of interest and non-nucleic targets of interest) could be one or more molecules from a virus, such as adenovirus, coronavirus HKU1, coronavirus NL63, coronavirus 229E, coronavirus OC43, severe acute respiratory syndrome coronavirus 2 (SARS-CoV-2), human metapneumovirus, human rhinovirus, enterovirus, influenza A, influenza A/H1, influenza A/H3, influenza A/H1-2009, influenza B, parainfluenza virus 1, parainfluenza virus 2, parainfluenza virus 3, parainfluenza virus 4, respiratory syncytial virus, herpes simplex virus 1, herpes simplex virus 2, human immunodeficiency virus (HIV), human papillomavirus, hepatitis A virus (HAV), hepatitis B virus (HBV), hepatitis C virus (HCV), and/or human parvovirus B19 (B19V). Also, as a non-limiting example, the targets of interest could be one or more nucleic acids or proteins from a fungus, such as *Candida albicans, Candida auris, Candida glabrata, Candida krusei, Candida parapsilosis, Candida tropicalis, Cryptococcus neoformans,* and/or *Cryptococcus gattii.* As another non-limiting example, the targets of interest could be one or more nucleic acids or proteins from a protozoan, such as *Toxoplasma gondii* or *Trichomonas vaginalis.*

Additionally, the targets of interest may originate in an organism such as a bacterium, virus, fungus or other pest that infects livestock or agricultural crops. Such organisms include avian influenza viruses, *mycoplasma* and other bovine mastitis pathogens, *Clostridium perfringens, Campylobacter* sp., *Salmonella* sp., Pospirivoidae, Avsunvirodiae, *Panteoea stewartii, Mycoplasma genitalium, Sprioplasma* sp., *Pseudomonas solanacearum, Erwinia amylovora, Erwinia carotovora, Pseudomonas syringae, Xanthomonas campestris, Agrobacterium tumefaciens, Spiroplasma citri, Phytophthora infestans, Endothia parasitica, Ceratocysis ulmi, Puccinia graminis, Hemilea vastatrix, Ustilage maydis, Ustilage nuda, Guignardia bidwellii, Uncinula necator, Botrytis cincerea, Plasmopara viticola,* or *Botryotinis fuckleina.*

Other targets of interest include cancer or other disease biomarkers. As mentioned below, for example, aptamers have been developed to detect cancer-related biomarkers, including MUC1 (mucin 1), HER2 (human epidermal growth factor receptor 2), and estrogen receptor; and have also been developed to detect a number of tumor-related soluble biomarkers, including carcinoembryonic antigen (CEA) and prostate specific antigen (PSA). Additionally, certain circulating nucleic acid sequences are known to correlate with certain cancers.

In some embodiments, other targets of interest may be for non-infectious conditions, e.g., to be used for genotyping, including non-invasive prenatal diagnosis of, e.g., trisomies, other chromosomal abnormalities, and known genetic diseases such as Tay Sachs disease and sickle cell anemia. Targets of interest may originate in engineered biologics, including cells such as CAR-T cells, or targets of interest may originate in very small or rare samples, where only small volumes are available for testing.

In some embodiments, other targets of interest may be for non-infectious conditions, e.g., to be used for environmental monitoring, such as for bioweapons, heavy metals or environmental toxins; for human metabolite detection; and for testing of foods and other commodities. Also in some embodiments, other targets of interest may be for metabolic markers, e.g., to be used for monitoring levels of specific metabolites, such as for diseases with metabolic measures, including but not limited to diabetes, cancer, kidney disease, liver disease, enzymatic deficits; for optimizing biological manufacturing processes; or for food testing. As non-limiting examples of metabolites, the targets of interest could be glucose, ketones, cholesterols, creatine, and lactate. In yet another embodiment, the targets of interest may comprise blood-derived factors such as clotting factors (Factors I-XIII), citrate, bilirubin, platelet growth factors, alpha-aminobutyric acid, gamma-aminolevulinic acid, androstenedione, vitamins, cerluplasmin, panceraozymin, complement factors, hormones, fatty acids, alpha-1-fetoprotein, sugars, fats, and minerals.

The signal boost cascade assays described herein are particularly well-suited for simultaneous testing of multiple to many targets of interest (both nucleic acid and non-nucleic acid targets of interest) via massively multiplexed gRNAs as described below. Pools of two to 10,000 different RNP1s for detecting both nucleic acid (including mixes of RNA and DNA targets of interest) and non-nucleic targets of interest may be employed, e.g., pools of two to 5000, two to 1000, two to 100, two to 50, or two to 10 targets of interest. For example, pools of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 different RNP1s for detecting both nucleic acid (including mixes of RNA and DNA targets of interest) and non-nucleic targets of interest may be employed.

Aptamers

Aptamers are short, single-stranded oligonucleotides (DNA or RNA or a chimera) that bind to non-nucleic acid targets of interest with high specificity and affinity by folding into a tertiary structure. Aptamers have been used in basic research and in food safety and environmental monitoring. As described above, although aptamers recognize and bind non-nucleic acid targets of interest like antibodies, aptamers have a number of advantages over antibodies. For example, aptamers are more easily and cheaply manufactured than antibodies, are able to withstand repeated rounds of denaturation and renaturation, are temperature resistant (e.g., stable at room temperature), have little batch to batch variation, and have a long shelf life. In addition, selection of aptamers via SELEX (Systematic Evolution of Ligands by Exponential Enrichment) takes only 2-8 weeks, whereas antibodies are produced in vivo via a laborious and expensive process that typically takes more than 6 months. Also, aptamers can be easily modified without affinity loss. The target potential for aptamers includes ions, small molecules, whole cells and live animals. (See, e.g., Zhang, et al., Molecules, 24:941-63 (2019).)

Aptamers are generated via systematic evolution of ligands by exponential enrichment (SELEX) and variations to SELEX. In a typical SELEX protocol, an aptamer library of approximately $10^{14}$-$10^{16}$ single-stranded DNA or RNA random oligonucleotides 20-150 nucleotides in length are synthesized. The aptamers comprise 5' and 3' fixed primer sequences and a random region in the middle of the oligonucleotide. The aptamer library is incubated with the non-nucleic acid target of interest, the bound oligonucleotides are partitioned from unbound oligonucleotides and amplified by PCR, resulting in a pool of enriched oligonucleotides to be used in another round of selection.

Variations to SELEX include immunoprecipitation-coupled SELEX (IP-SELEX) (selects aptamers against proteins under normal physiological conditions), capture SELEX (the aptamer library is immobilized on a support rather than the non-nucleic acid target of interest), cell-SELEX (utilizes whole live cells as non-nucleic acid targets of interest), capillary electrophoresis-SELEX (CE-SELEX) (involves separation of ions based on electrophoretic mobility), atomic force microscopy-SELEX (AFM-SELEX) (employs AFM to create a three-dimensional image of the non-nucleic acid target of interest surface), artificially expanded genetic information system-SELEX (AEGIS-SELEX) (utilizes libraries with an artificially expanded genetic code) and animal SELEX (aptamers are selected directly within live animals). For more information on SELEX techniques, again see Zhang, et al., Molecules, 24:941-63 (2019).

Aptamers can be used like antibodies are used, and, in the present context, for, e.g., diagnostics. As used herein, "diagnostics" refers to not only the detection of infectious agents or proteins indicative of disease, but also to test and monitor the environment. Aptamers have been utilized to detect surface proteins of *Campylobater jejuni*, and the cell-SELEX system was used to detect *E. coli*, *Lactobacillus acidophilus*, *Staphylococcus aureus*, *Mycobacterium tuberculosis*, and others. Aptamers have also been used to detect viral infections including vaccinia virus, herpes simplex virus, hepatitis C virus, hepatitis B virus and SARS corona virus; and to detect parasites such as *Trypanosoma* sp., *Leishmania* sp., *Plasmodium* sp., *Cryptosporidium parvum*, and *Entamoeba histolytica*. (Id.)

Aptamers may be employed for cancer diagnosis and prognosis. To date, aptamers have been developed to detect cancer-related biomarkers, including tumor-related proteins in living cancer cells such as MUC1 (mucin 1), HER2 (human epidermal growth factor receptor 2), and estrogen receptor. (Id.) Aptamers have also been developed to detect a number of tumor-related soluble biomarkers, including carcinoembryonic antigen (CEA) and prostate specific antigen (PSA) and used for in vivo imaging of lymphoma, adenocarcinoma, leukemia, glioblastoma and other cancer types. (Id.)

Aptamers are also useful in monitoring environmental contamination. For example, aptamers have been developed against antibiotics to monitor the level of antibiotics from, e.g., livestock, in food. Additionally, aptamers have been developed against environmental toxins such as ochratoxin A and bacterial endotoxins and herbicides, and against heavy metals such as mercury, arsenic, copper, and lead.

Nucleic Acid-Guided Nucleases

The signal boost cascade assays comprise nucleic acid-guided nucleases in the reaction mixture, either provided as a protein, a coding sequence for the protein (for, e.g., in vivo applications), or, in many embodiments, in a ribonucleoprotein (RNP) complex. In some embodiments, the one or more nucleic acid-guided nucleases in the reaction mixture may be, for example, a Cas nuclease. Any nucleic acid-guided nuclease having both cis- and trans-endonuclease activity may be employed, and, depending on the cascade assay embodiment employed, the same nucleic acid-guided nuclease may be used for both the RNP1 and RNP2 complexes or different nucleic acid-guided nucleases may be used in RNP1 and RNP2 (and different nucleic acid-guided nucleases could be used among different RNP1s, particularly if there are both RNA and DNA nucleic acid targets of interest). Note that trans-cleavage activity is not triggered unless and until binding of a nucleic acid target of interest or an aptamer-complement is bound by RNP1. Nucleic acid-guided nucleases include Type V and Type VI nucleic acid-guided nucleases, as well as nucleic acid-guided nucleases that comprise a RuvC nuclease domain or a RuvC-like nuclease domain but lack an HNH nuclease domain. Nucleic acid-guided nucleases with these properties are reviewed in Makarova and Koonin, Methods Mol. Biol., 1311:47-75 (2015) and Koonin, et al., Current Opinion in Microbiology, 37:67-78 (2020) and updated databases of nucleic acid-guided nucleases and nuclease systems that include newly-discovered systems include BioGRID ORCS (orcs: thebiogrid.org); GenomeCRISPR (genomecrispr.org); Plant Genome Editing Database (plantcrispr.org) and CRISPR-CasFinder (crispercas.i2bc.paris-saclay.fr).

The type of nucleic acid-guided nuclease utilized in the method of detection depends on the type of nucleic acid target of interest to be detected. For example, a DNA nucleic acid-guided nuclease (e.g., a Cas12a, Cas14a, or Cas3) should be utilized if the nucleic acid target of interest or aptamer-complement is a DNA molecule, and an RNA nucleic acid-guided nuclease (e.g., Cas13a or Cas12g) should be utilized if the nucleic acid target of interest or aptamer-complement is an RNA molecule. Exemplary nucleic acid-guided nucleases include, but are not limited to, Cas RNA-guided DNA endonucleases, such as Cas3, Cas12a (e.g., AsCas12a, LbCas12a), Cas12b, Cas12c, Cas12d, Cas12e, Cas14, Cas12h, Cas12i, and Cas12j; Cas RNA-guided RNA endonucleases, such as Cas13a (LbaCas13, LbuCas13, LwaCas13), Cas13b (e.g., CccaCas13b, PsmCas13b), and Cas12g; and any other nucleic acid (DNA, RNA, or cDNA) targeting nucleic acid-guided nuclease with cis-cleavage activity and collateral trans-cleavage activity. In some embodiments, the nucleic acid-guided nuclease is a Type V CRISPR-Cas nuclease, such as a Cas12a, Cas13a, or Cas14a. In some embodiments, the nucleic acid-guided nuclease is a Type I CRISPR-Cas nuclease, such as Cas3. Type II and Type VI nucleic acid-guided nucleases may also be employed, again, as long as the nucleic acid-guided nuclease exhibits both cis- and trans-cleavage activity.

Guide RNA (gRNA)

The present disclosure may detect targets of interest (both nucleic acid targets of interest and non-nucleic acid targets of interest) via a reaction mixture containing at least three guide RNAs (gRNAs) each incorporated into an RNP complex (i.e., RNP1-NA, RNP1-NON and RNP2). Suitable gRNAs comprise at least one crRNA region to enable specificity in every reaction. The gRNA1s of the RNP1s are specific to targets of interest or an aptamer complement, and the gRNA of RNP2 is specific to, depending on the cascade assay embodiment, an unblocked nucleic acid or a synthesized activating nucleic acid or an RNP2 activating nucleic acid (all of which are described in detail below). As will be clear given the description below, an advantageous feature of the signal boost cascade assay is that, with the exception of the gRNA in the RNP1 (i.e., the gRNA specific to the nucleic acid target of interest or to the aptamer-complement) and the aptamer and aptamer-complement, the signal boost cascade assay components can be the same (i.e., are identical or substantially identical) no matter what targets of interest are being detected, and each of these components is easily reprogrammable.

Like the nucleic acid-guided nuclease, the gRNA may be provided in the cascade assay reaction mixture in a preassembled RNP, or as an RNA molecule, or, for in vivo applications, may also be provided as a DNA sequence to be transcribed, in, e.g., a vector backbone. Providing the gRNA in a pre-assembled RNP complex (i.e., RNP1 or RNP2) is preferred if rapid assay kinetics are preferred. If provided as a gRNA molecule, the gRNA sequence may include multiple endoribonuclease recognition sites (e.g., Csy4) for multiplex processing. Alternatively, if provided as a DNA sequence to be transcribed, an endoribonuclease recognition site is encoded between neighboring gRNA sequences and more than one gRNA can be transcribed in a single expression cassette. Direct repeats can also serve as endoribonuclease recognition sites for multiplex processing. Guide RNAs are generally about 20 nucleotides to about 300 nucleotides in length and may contain a spacer sequence containing a plurality of bases and complementary to a protospacer sequence in the target sequence. The gRNA spacer sequence may be 50%, 60%, 75%, 80%, 85%, 90%, 95%, 97.5%, 98%, 99%, or more complementary to its intended nucleic acid target of interest.

The gRNA of RNP1 is capable of complexing with the nucleic acid-guided nuclease of RNP1 to perform cis-cleavage of a target of interest (i.e., the nucleic acid target of interest or aptamer-complement), which triggers non-sequence specific trans-cleavage of other molecules in the reaction mixture. Guide RNAs include any polynucleotide sequence having sufficient complementarity with the nucleic acid target of interest or aptamer-complement in relation to RNP1s or nucleic acid sequences generated by unblocking blocked nucleic acid molecules, nucleic acid sequences generated by synthesizing activating nucleic acids, or RNP2 activating nucleic acids in relation to RNP2s as described below. The nucleic acid target of interest and/or aptamer-complement that binds with an RNP1 and/or other nucleic acid sequences that complex with RNP2 may include a protospacer-adjacent motif (PAM), and, following gRNA binding, the nucleic acid-guided nuclease induces a double-stranded break either inside or outside the protospacer region.

In some embodiments, the gRNA (e.g., of RNP1) is an exo-resistant circular molecule that can include several DNA bases between the 5' end and the 3' end of a natural guide RNA and is capable of binding a target sequence. The length of the circularized guide for RNP1 can be such that the circular form of guide can be complexed with a nucleic acid-guided nuclease to form a modified RNP1 which can still retain its cis-cleavage i.e., (specific) and trans-cleavage (i.e., non-specific) nuclease activity.

In any of the foregoing embodiments, the gRNA may be a modified or non-naturally occurring nucleic acid molecule. In some embodiments, the gRNAs of the disclosure may further contain a locked nucleic acid (LNA), a bridged nucleic acid (BNA), and/or a peptide nucleic acid (PNA). By way of further example, a modified nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, or any other nucleic acid molecule modifications described herein.

Ribonucleoprotein (RNP) Complex

As described above, although the assay "reaction mix" or "reaction mixture" may comprise separate nucleic acid-guided nucleases and gRNAs (or, for in vivo applications, coding sequences therefor), the cascade assays preferably comprise preassembled ribonucleoprotein complexes (RNPs) in the reaction mixture, allowing for faster detection kinetics. The present cascade assay optionally employs at least three types of RNP complexes, RNP1-NA, RNP1-NON and RNP2 (assuming both nucleic acid and non-nucleic acid targets of interest are being detected), each type containing a nucleic acid-guided nuclease and a gRNA. Depending on the cascade assay and the array-based readout embodiment, the RNP1s and RNP2s may comprise the same nucleic acid-guided nuclease or may comprise different nucleic acid-guided nucleases; however, the gRNAs in the RNP1s and RNP2s are different and are configured to bind different nucleic acids. In some embodiments, the reaction mixture contains about 1 fM to about 10 µM of a given RNP1, or about 1 pM to about 1 µM of a given RNP1, or about 10 µM to about 500 pM of a given RNP1. In some embodiments the reaction mixture contains about $6\times10^4$ to about $6\times10^{12}$ complexes per microliter (µl) of a given RNP1, or about $6\times10^6$ to about $6\times10^{10}$ complexes per microliter (µl) of a given RNP1. In some embodiments, the reaction mixture contains about 1 fM to about 500 µM of a given RNP2, or about 1 pM to about 250 µM of a given RNP2, or about 10 pM to about 100 µM of a given RNP2. For example, the reaction mixture can contain about 1 fM, about 5 fM, about 10 fM, about 20 fM, about 50 fM, about 100 fM, about 250 fM, about 500 fM, about 750 fM, about 900 fM, about 1 pM, about 5 pM, about 10 pM, about 20 pM, about 50 pM, about 100 pM, about 250 pM, about 500 pM, about 750 pM, about 900 pM, about 1 nM, about 5 nM, about 10 nM, about 20 nM, about 50 nM, about 100 nM, about 250 nM, about 500 nM, about 750 nM, about 900 nM, about 1 µM, about 5 µM, about 10 µM, about 20 µM, about 50 µM, about 100 µM, about 250 µM, or about 500 µM of a given RNP2.

In some embodiments the reaction mixture contains about $6\times10^4$ to about $6\times10^{12}$ complexes per microliter (µl) of a given RNP2 or about $6\times10^6$ to about $6\times10^{12}$ complexes per microliter (µl) of a given RNP2. For example, the reaction mixture can contain $6\times10^4$, $6\times10^5$, $6\times10^6$, $6\times10^7$, $6\times10^8$, $6\times10^9$, $6\times10^{10}$, $6\times10^{11}$, or $6\times10^{12}$ complexes per microliter (µl) of a given RNP2.

In any of the embodiments of the disclosure, the reaction mixture includes 1 to about 10,000 different RNP1s (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 RNP1s), where different RNP1s comprise a different gRNA (or crRNA thereof) polynucleotide sequence to bind to different nucleic acid targets of interest (both RNA and DNA or a mixture of RNA and DNA) and/or aptamer-complements. For example, a reaction mixture designed for environmental or oncology testing comprises more than one unique RNP1-gRNA (or RNP1-crRNA) ribonucleoprotein complex for the purpose of detecting more than one target of interest (i.e., nucleic acid target of interest or non-nucleic acid target of interest). That is, more than one RNP1 may be present for the purpose of targeting one target of interest from many sources or more than one RNP1 may be present for targeting more than one target of interest from a single organism or condition.

In any of the foregoing embodiments, the gRNA of RNP1 may be homologous or heterologous relative to the gRNA of other RNP1(s) present in the reaction mixture. A homologous mixture of RNP1 gRNAs has a number of gRNAs with the same nucleotide sequence against the same nucleic acid target of interest or aptamer-complement, whereas a heterologous mixture of RNP1 gRNAs has multiple gRNAs with different nucleotide sequences (e.g., gRNAs targeting different nucleic acid targets of interest and/or aptamer-complements). Therefore, the disclosed methods of identifying one or more (more typically two or more) nucleic acid and non-nucleic acid targets of interest may include a reaction mixture containing more than two heterologous gRNAs, more than three heterologous gRNAs, more than four heterologous gRNAs, more than five heterologous gRNAs, more than six heterologous gRNAs, more than seven heterologous gRNAs, more than eight heterologous gRNAs, more than nine heterologous gRNAs, more than ten heterologous gRNAs, more than eleven heterologous gRNAs, more than twelve heterologous gRNAs, more than thirteen heterologous gRNAs, more than fourteen heterologous gRNAs, more than fifteen heterologous gRNAs, more than sixteen heterologous gRNAs, more than seventeen heterologous gRNAs, more than eighteen heterologous gRNAs, more than nineteen heterologous gRNAs, more than twenty heterologous gRNAs, more than twenty-one heterologous gRNAs, more than twenty-three heterologous gRNAs, more than twenty-four heterologous gRNAs, or more than twenty-five heterologous gRNAs, or more than 50, 100, 250, 500, 1000, 5000, 10,000 or more heterologous gRNAs. Such a heterologous mixture of RNP1 gRNAs in a single reaction enables multiplex testing.

As a first non-limiting example of a heterologous mixture of RNP1 gRNAs, the reaction mixture may contain: a number of RNP1s having a gRNA targeting nucleic acid targets that can detect anthrax; a number of RNP1s having a gRNA targeting nucleic acid targets that can detect plague; a number of RNP1s having a gRNA targeting nucleic acid targets that can detect botulism; a number of RNP1s having a gRNA targeting nucleic acid targets that can detect hemorrhagic viruses; a number of RNP1s having a gRNA targeting the aptamer-complement of an aptamer that can detect mercury; a number of RNP1s having a gRNA targeting the aptamer-complement of an aptamer that can detect arsenic; and a number of RNP1s having a gRNA targeting the aptamer-complement of an aptamer that can detect lead.

As another non-limiting example of a heterologous mixture of RNP1 gRNAs, the reaction mixture may contain RNP1s targeting two or more nucleic acid and/or non-nucleic acid targets of interest from organisms that infect vineyards or byproducts thereof, such as *Guignardia bidwellii*, *Uncinula necator*, *Botrytis cincerea*, *Plasmopara viticola*, and *Botryotinia fuckeliana*.

Reporter Moieties

The signal boost cascade assay detects nucleic acid and non-nucleic acid targets of interest via detection of a signal generated in the reaction mixture by a reporter moiety.

Depending on the type of reporter moiety used, trans- and/or cis-cleavage by the nucleic acid-guided nuclease in RNP2 releases a signal. In some embodiments, trans-cleavage of stand-alone (e.g., not bound to any blocked nucleic acid molecules) reporter moieties may generate signal changes at rates that are proportional to the cleavage rate, as new RNP2s are activated over time (shown to the right of FIG. 1 and at top of FIG. 6). Trans-cleavage by either an activated RNP1 or an activated RNP2 may release a signal although the vast majority of the signals are generated via activated RNP2s; thus, when the reporter moiety is a separate molecule, the reporter moieties are activated quickly by the trans-cleavage activity.

Figure 6:
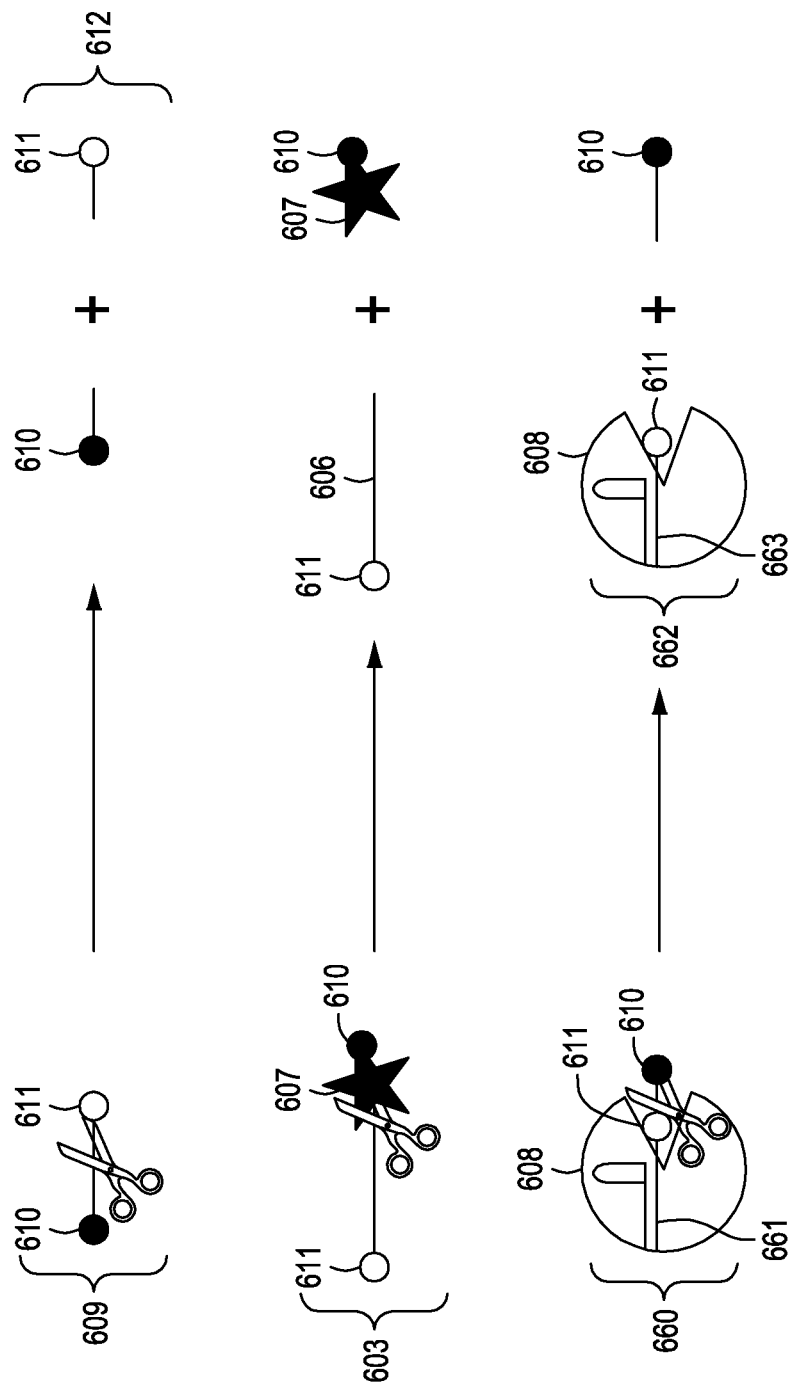
FIG. 6 illustrates three embodiments of reporter moieties.

In alternative embodiments and preferably, the reporter moiety may be bound to the blocked nucleic acid molecule, where trans-cleavage of the blocked nucleic acid molecule and conversion to an unblocked nucleic acid molecule may generate signal changes at rates that are proportional to the cleavage rate, as new RNP2s are activated over time, thus allowing for real time reporting of results (shown at FIG. 6, center). In this embodiment, the reaction kinetics of signal generation matches that of the cascade assay reaction rate. The signal is generated as the blocked nucleic acid molecule is unblocked, whether quickly or slowly. In yet another embodiment, the reporter moiety may be bound to a blocked nucleic acid molecule such that cis-cleavage following the binding of the RNP2 to an unblocked nucleic acid molecule releases a PAM distal sequence, which in turn generates a signal at rates that are proportional to the cis-cleavage rate of the unblocked nucleic acid molecule (shown at FIG. 6, bottom). In this case, activation of RNP2 by cis-(target specific) cleavage of the unblocked nucleic acid molecule directly produces a signal, rather than producing a signal via indiscriminate trans-cleavage activity. Alternatively or in addition, the reporter moiety may be bound to the gRNA.

The reporter moiety may be a synthetic molecule linked or conjugated to a reporter and quencher such as, for example, a TaqMan probe with a dye label (e.g., FAM or FITC) on the 5' end and a quencher on the 3' end. The reporter and quencher may be about 20-30 bases apart or less for effective quenching via fluorescence resonance energy transfer (FRET). Alternatively, signal generation may occur through different mechanisms. Other detectable moieties, labels, or reporters can also be used to detect a nucleic acid target of interest as described herein. Reporter moieties can be labeled in a variety of ways, including direct or indirect attachment of a detectable moiety such as a fluorescent moiety, hapten, or colorimetric moiety.

Examples of detectable moieties include various radioactive moieties, enzymes, prosthetic groups, fluorescent markers, luminescent markers, bioluminescent markers, metal particles, and protein-protein binding pairs, e.g., protein-antibody binding pairs. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, and phycoerythrin. Examples of bioluminescent markers include, but are not limited to, luciferase (e.g., bacterial, firefly, click beetle and the like), luciferin, and aequorin. Examples of enzyme systems having visually detectable signals include, but are not limited to, galactosidases, glucorinidases, phosphatases, peroxidases, and cholinesterases. Identifiable markers also include radioactive elements such as $^{125}I$, $^{35}S$, $^{14}C$, or $^{3}H$. Reporters can also include a change in pH or charge of the cascade assay reaction mixture.

The methods used to detect the generated signal will depend on the reporter moiety or moieties used. For example, a radioactive label can be detected using a scintillation counter, photographic film as in autoradiography, or storage phosphor imaging. Fluorescent labels can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Enzymatic labels can be detected by providing the appropriate substrates for the enzyme and detecting the resulting reaction product. Simple colorimetric labels can be detected by observing the color associated with the label. When pairs of fluorophores are used in an assay, fluorophores are chosen that have distinct emission patterns (wavelengths) so that they can be easily distinguished. In some embodiments, the signal can be detected by lateral flow assays (LFAs). Lateral flow tests are simple devices intended to detect the presence or absence of a nucleic acid target of interest in a sample. LFAs can use nucleic acid molecules conjugated nanoparticles (often gold, e.g., RNA-AuNPs or DNA-AuNPs) as a detection probe, which hybridizes to a complementary target sequence. The classic example of an LFA is the home pregnancy test.

Single-stranded nucleic acid reporter moieties such as ssDNA reporter moieties or RNA molecules can be introduced to show a signal change proportional to the cleavage rate, which increases with every new activated RNP2 complex over time. In some embodiments and as described in detail below, nucleic acid reporter moieties (single or double stranded) can also be embedded into the blocked nucleic acid molecules for real time reporting of results.

For example, the method of detecting a targets of interest in a sample using a cascade assay as described herein can involve contacting the reaction mixture with a labeled detection DNA containing a fluorescent resonance energy transfer (FRET) pair, a quencher/phosphor pair, or both. A FRET pair consists of a donor chromophore and an acceptor chromophore, where the acceptor chromophore may be a quencher molecule. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5, Texas Red/DABCYL, BODIPY/DABCYL, Lucifer yellow/DABCYL, coumarin/DABCYL, and fluorescein/LC Red 705. In addition, a fluorophore/quantum dot donor/acceptor pair can be used. EDANS is (5-((2-aminoethyl)amino)naphthalene-1-sulfonic acid); IAEDANS is 5-({2-[(iodoacetyl)amino]ethyl}amino)naphthalene-1-sulfonic acid); DABCYL is 4-((4-(dimethylamino) phenyl) diazenyl)benzoic acid. Useful quenchers include, but are not limited to, DABCYL, QSY 7 and QSY 33.

In any of the foregoing embodiments, the reporter moiety may comprise one or more modified nucleic acid molecules, containing a modified nucleoside or nucleotide. In some embodiments the modified nucleoside or nucleotide is chosen from 2'-O-methyl (2'-O-Me) modified nucleoside, a 2'-fluoro (2'-F) modified nucleoside, and a phosphorothioate (PS) bond, or any other nucleic acid molecule modifications described below.

Nucleic Acid Modifications

For any of the nucleic acid molecules described herein (e.g., aptamer-complements, blocked nucleic acid molecules, blocked primer molecules, gRNAs, blocked guide nucleic acids, template molecules, RNP2 activating nucleic acids, synthesized activating nucleic acids, and reporter moieties), the nucleic acid molecules may be used in a wholly or partially modified form. Typically, modifications to the aptamer-complements, blocked nucleic acids, gRNAs, blocked guide nucleic acids, template molecules, reporter moieties, and blocked primer molecules described herein are introduced to optimize the molecule's biophysical properties (e.g., increasing endonuclease resistance and/or increasing thermal stability). Modifications typically are achieved by the incorporation of, for example, one or more alternative nucleosides, alternative sugar moieties, and/or alternative internucleoside linkages.

For example, one or more of the cascade assay components may include one or more of the following nucleoside modifications: 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, and/or 3-deazaguanine and 3-deazaadenine. The nucleic acid molecules described herein (e.g., aptamer-complements, blocked nucleic acid molecules, blocked primer molecules, gRNAs, reporter molecules, synthesized activating nucleic acids, and template molecules) may also include nucleobases in which the purine or pyrimidine base is replaced with other heterocycles, for example 7-deaza-adenine, 7-deazaguanosine, 2-aminopyridine, and/or 2-pyridone. Further modification of the nucleic acid molecules described herein may include nucleobases disclosed in U.S. Pat. No. 3,687,808; Kroschwitz, ed., *The Concise Encyclopedia of Polymer Science and Engineering*, New York, John Wiley & Sons, 1990, pp. 858-859; Englisch, et al., Angewandte Chemie, 30:613 (1991); and Sanghvi, Chapter 16, *Antisense Research and Applications*, CRC Press, Gait, ed., 1993, pp. 289-302.

In addition to or as an alternative to nucleoside modifications, the cascade assay components may comprise 2' sugar modifications, including 2'-O-methyl (2'-O-Me), 2'-methoxyethoxy (2'-O—CH$_2$CH$_2$OCH$_3$, also known as 2'-O-(2-methoxyethyl) or 2'-MOE), 2'-dimethylaminooxyethoxy, i.e., a O(CH$_2$)$_2$ON(CH$_3$)$_2$ group, also known as 2'-DMAOE, and/or 2'-dimethylaminoethoxyethoxy (also known in the art as 2'-O-dimethylamino-ethoxy-ethyl or 2'-DMAEOE), i.e., 2'-O—(CH$_2$)$_2$O(CH$_2$)$_2$N(CH$_3$)$_2$. Other possible 2'-modifications that can modify the nucleic acid molecules described herein (i.e., aptamer-complements, blocked nucleic acids, gRNAs, synthesized activating nucleic acid, reporter molecules, and blocked primer molecules) may include all possible orientations of OH; F; O-, S-, or N-alkyl (mono- or di-); O-, S-, or N-alkenyl (mono- or di-); O-, S- or N-alkynyl (mono- or di-); or O-alkyl-O-alkyl, wherein the alkyl, alkenyl and alkynyl may be substituted or unsubstituted C1 to C10 alkyl or C2 to C10 alkenyl and alkynyl. Other potential sugar substituent groups include, e.g., aminopropoxy (—OCH$_2$CH$_2$CH$_2$NH$_2$), allyl (—CH$_2$—CH═CH$_2$), —O-allyl (—O—CH$_2$—CH═CH$_2$) and fluoro (F). 2'-sugar substituent groups may be in the arabino (up) position or ribo (down) position. In some embodiments, the 2'-arabino modification is 2'-F. Similar modifications may also be made at other positions on the interfering RNA molecule, particularly the 3' position of the sugar on the 3' terminal nucleoside or in 2'-5' linked oligonucleotides and the 5' position of 5' terminal nucleotide. Oligonucleotides may also have sugar mimetics such as cyclobutyl moieties in place of the pentofuranosyl sugar.

Finally, modifications to the cascade assay components may comprise internucleoside modifications such as phosphorothioates, phosphorodithioates, phosphotriesters, aminoalkylphosphotriesters, methyl and other alkyl phosphonates including 3'-alkylene phosphonates, 5'-alkylene phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

Aptamer Binding

Figure 2A:
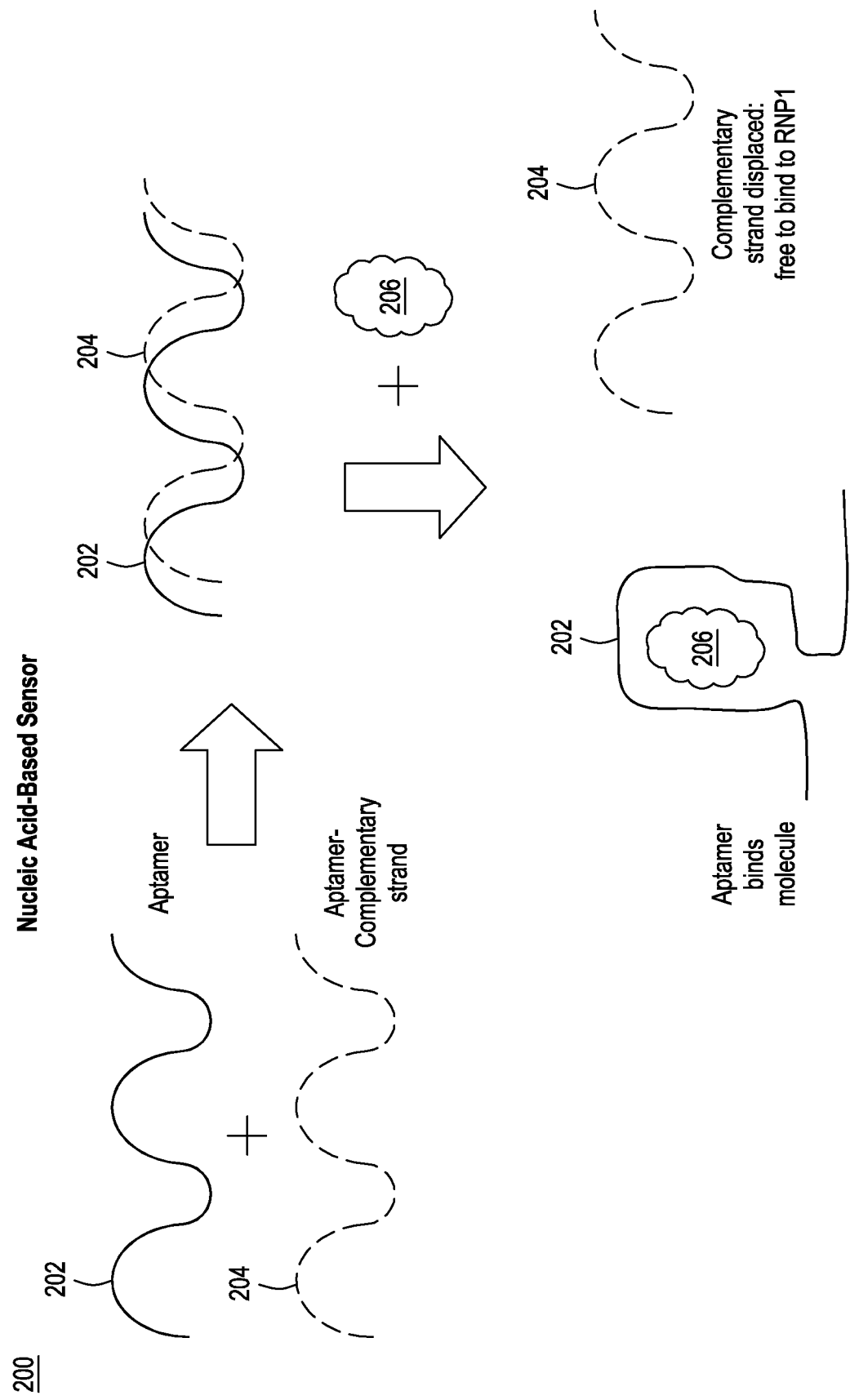
FIG. 2A is a simplified illustration of how the nucleic acid-guided nuclease cascade assay can be applied to non-nucleic acid targets of interest.

FIG. 2A is a simplified illustration of how the nucleic acid-guided nuclease cascade assay can be applied to non-nucleic acid targets of interest. (The simplified description in FIG. 2A will be described in detail in relation to FIGS. 3A, 4A, 4B and 5A below.) In FIG. 2A, method 200 for identifying a non-nucleic acid target of interest is shown. Shown is an aptamer 202 and aptamer-complement 204. When hybridized, aptamer 202 and aptamer-complement 204 form a double-strand construct which, if aptamer 202 binds to a non-nucleic acid target of interest 206 in a sample, frees the now single strand aptamer-complement to bind to RNP1 in the assay. That is, the aptamer-complement is complementary to gRNA1 of RNP1 and thus is the "target nucleic acid sequence" or "nucleic acid target" for RNP1. As described herein, the non-nucleic acid target of interest can be a metabolite, peptide, transcription factor, post-translation or other protein modification such as phosphorylation or glycosolation (often associated with a disease state), or metal.

Figure 2B:
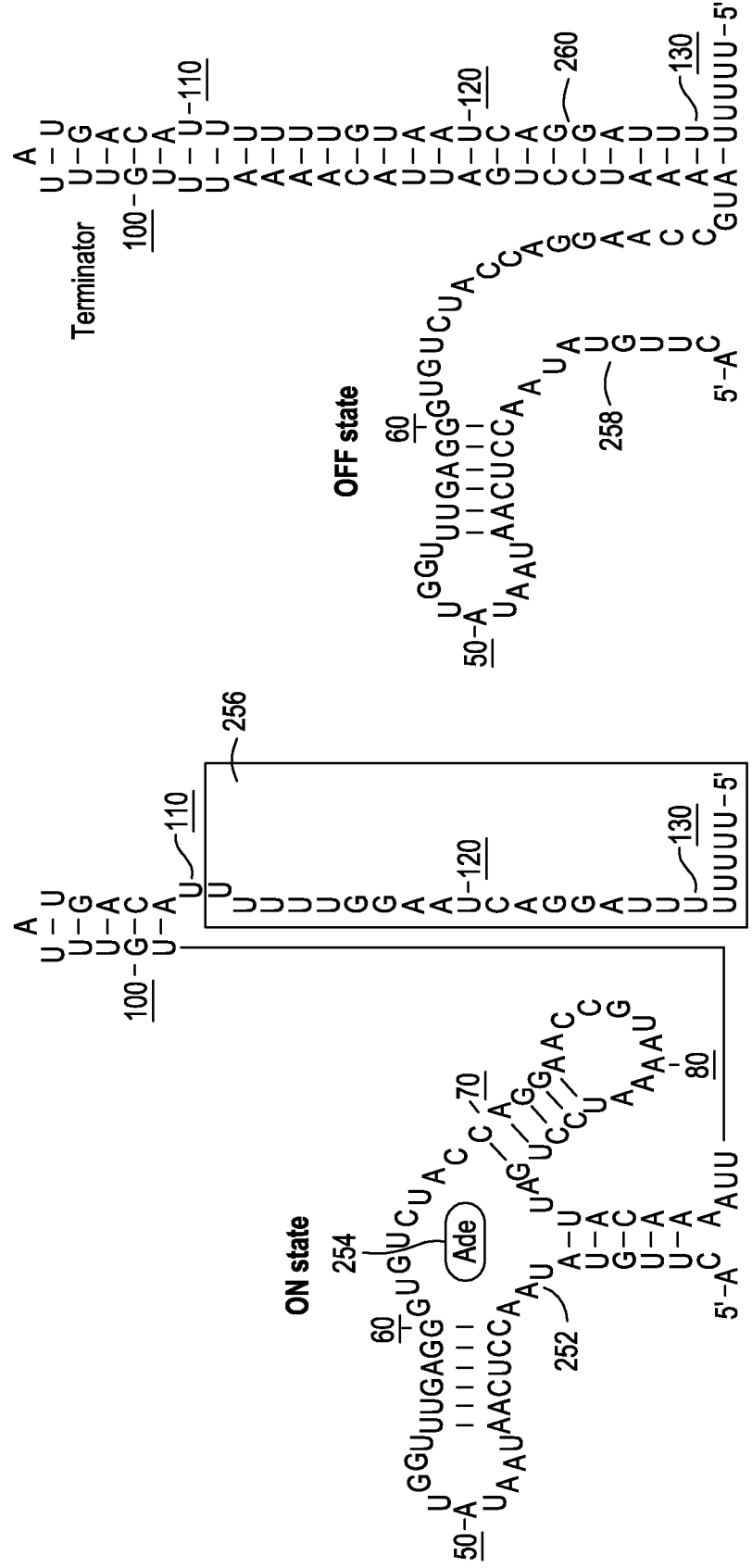
FIGS. 2B and 2C are simplified illustrations of identifying a binding event via a riboswitch.
Figure 2C:
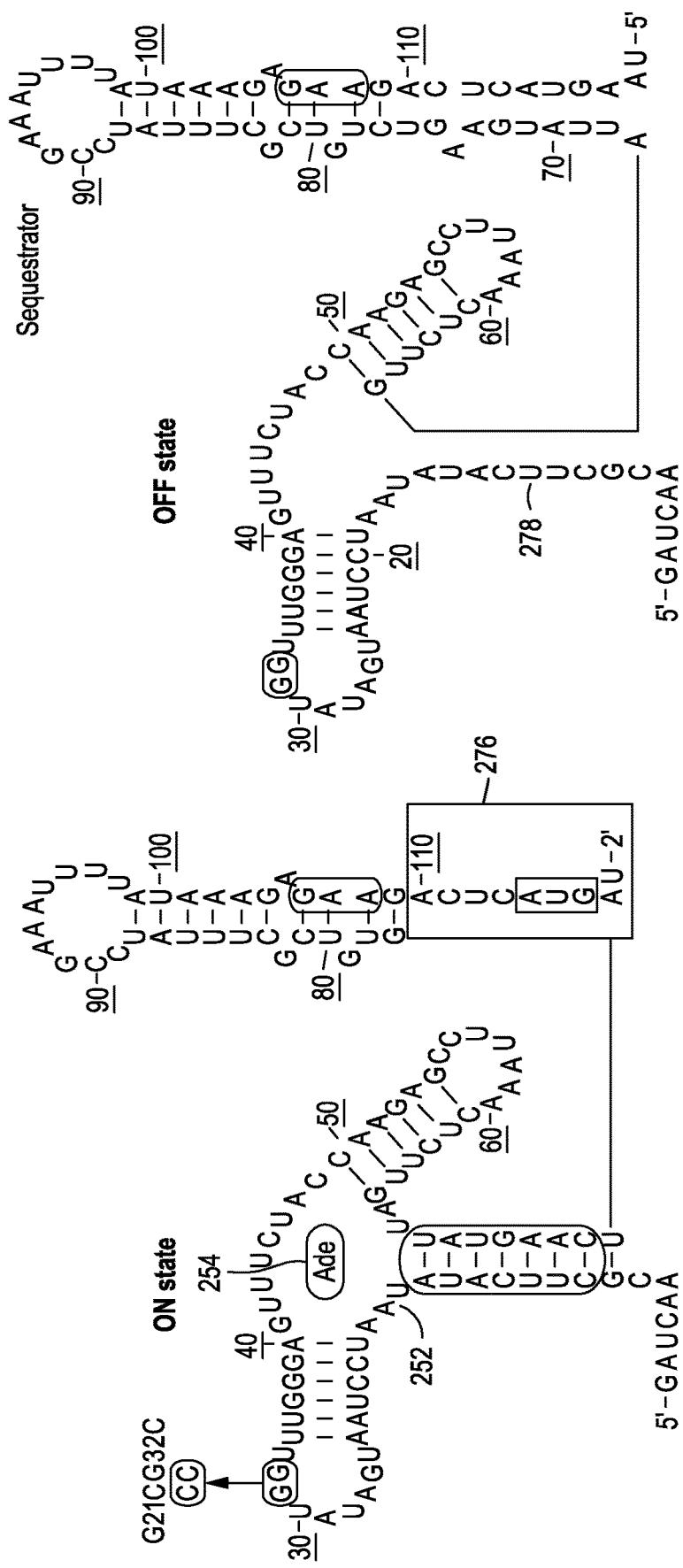

FIGS. 2B and 2C are simplified illustrations of identifying a binding event via a riboswitch. Riboswitches are cis-acting elements commonly found in the 5'-untranslated region of mRNAs that exert regulatory control over the transcript by directly binding an effector molecule ligand. The typical riboswitch contains two distinct functional domains: an aptamer domain and an expression platform. The effector molecule is recognized by the aptamer domain, essentially as described above (e.g., as described in relation to FIG. 2A) which adopts a compact three-dimensional fold to configure the ligand binding pocket specific for the effector molecule. The aptamer domain can discriminate between chemically related ligands with high selectivity to elicit the appropriate regulatory response.

A second domain the expression platform contains a secondary structural switch that interfaces with the transcriptional or translational machinery of the transcript. Regulation is achieved by virtue of a region of overlap between these two domains, known as the switching sequence. In the present context, however, instead of gene expression the binding event of the effector molecule leads to recognition of a single strand portion of the switching sequence by RNP1. In FIG. 2B at 250, construct 252 in the "on state" is bound to non-nucleic acid target 254 resulting in region 256 being "unmasked" (i.e., single stranded) and available for cis-cleavage by RNP1. In the "off state"

construct 258 is not bound to an effector molecule 254 (i.e., here, the non-nucleic acid target) and region 260 is "masked" (i.e., not single stranded) and therefore is not available for cis-cleavage by RNP1. In FIGS. 2B and 2C, nucleotide numbering positions are underlined. Likewise in FIG. 2C at 270, construct 252 in the "on state" is bound to the effector molecule 254 (i.e., non-nucleic acid target) resulting in region 276 being "unmasked" and available for cis-cleavage by RNP1. In the "off state", construct 278 is not bound to effector molecule 254 and region 260 is "masked" (i.e., not single stranded) and not available for cis-cleavage by RNP1. Thus, like the aptamer embodiment described in relation to FIG. 2A, binding of an effector molecule (i.e., non-nucleic acid target) to the aptamer domain of the riboswitch triggers cis-cleavage activity of RNP1, which begins the cascade.

There are many known naturally occurring riboswitches, including those that detect cobalamin, cyclic AMP-GMP, cyclic di-AMP, cylic di-GMP, fluoride, flavin mononucleotide (FMN), glmS (glucose-6-phosphate, glutamine, glycine, lysine, manganese, NiCo, PreQ1 (pre-queuosine 1, purine, SAH (S-adenosylhomocysteine), SAM (S-adenosyl methionine), SAM-SAH (recognize both S-adenosylhomocysteine and S-adenosyl methionine), tetrahdrofolate, TPP, and SMP.STP riboswitches. The aptamer domain of an existing riboswitch may be replaced with an aptamer binding domain of choice (i.e., to detect a target of choice, such as a metal- or protein-sensing aptamer), while the expression platform is retained. To choose a riboswitch appropriate for a target, one can screen for an aptamer, as described above, using, e.g., SELEX and/or related processes, or one can consult a free, publicly available database such as RiboD, Rswitch, and NDB; or the commercial database offered by Aptagen, LLC (Jacobus, PA).

Figure 2D:
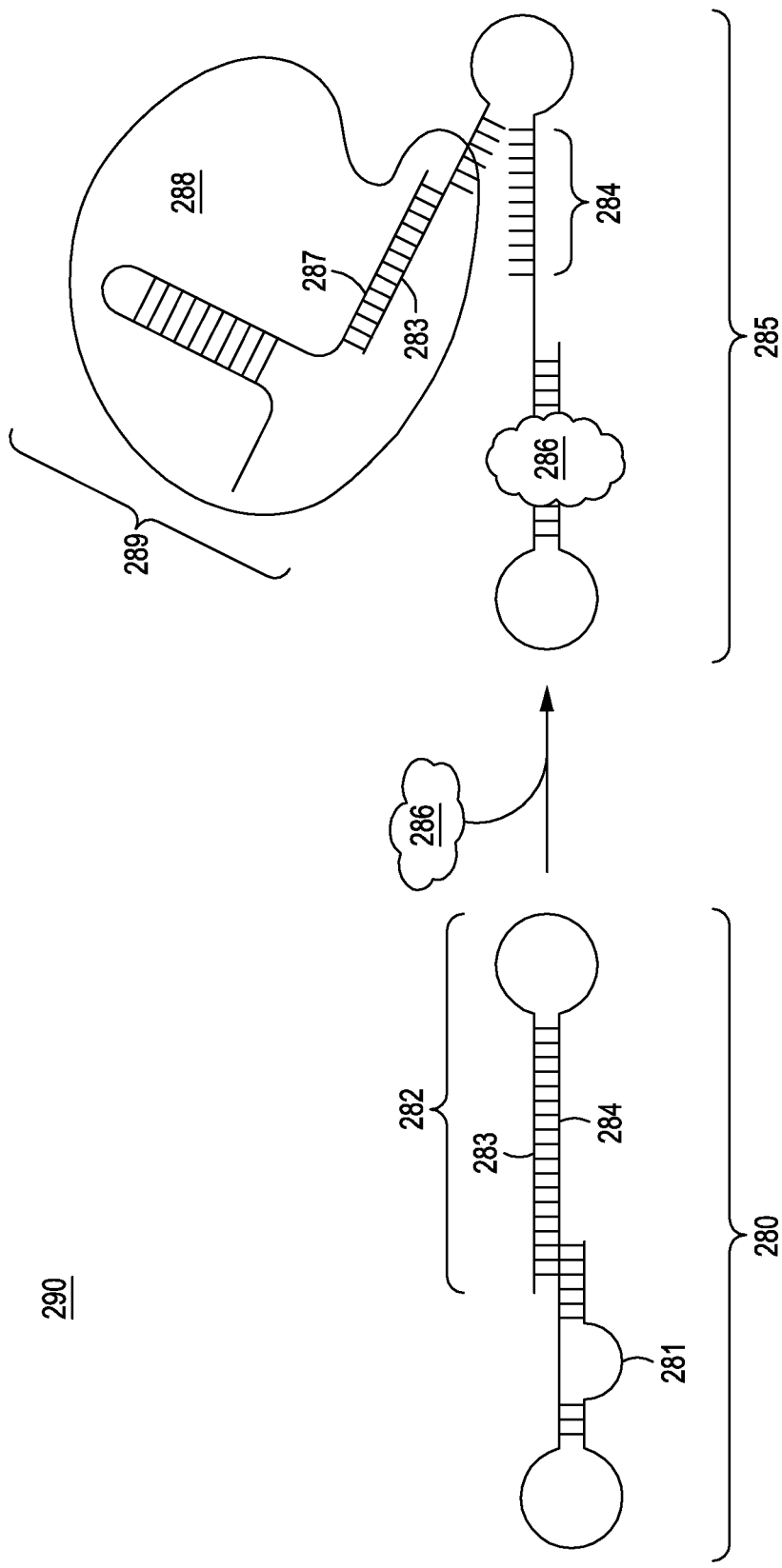
FIG. 2D is a simplified illustration of an alternative embodiment of how the nucleic acid-guided nuclease cascade assay can be applied to non-nucleic acid targets of interest.

An alternative embodiment for detecting non-nucleic acid targets of interest to that described in relation to FIG. 2A is seen FIG. 2D. In FIG. 2D, method 290 depends not on displacing an aptamer-complement but on competing stem/loops and a change in free energy. Seen is an aptamer/masked molecule compound molecule 280 comprising an aptamer region 281 and a masked molecule region 282 comprising a target strand 283 and a non-target strand 284. If the aptamer region 281 binds a non-nucleic acid target 286 in a sample, the aptamer/masked molecule compound molecule 280 changes conformation to free the target strand 283 (280→285) of the masked molecule region 282; that is, the masked molecule region is unmasked freeing the target strand 283 to bind to a gRNA 287 complexed with a nuclease 288 in a ribonucleoprotein complex 289. As described herein, the non-nucleic acid target of interest can be a metabolite, peptide, transcription factor, post-translation or other protein modification such as phosphorylation or glycosolation (often associated with a disease state), or metal. Note that where the method for non-nucleic acid detection shown in FIG. 2A is described in detail in relation to FIGS. 3A, 4A, 4B and 5A below, the embodiment described in this FIG. 2D could be used as an alternative for detecting the non-nucleic acid target.

The Cascade Assay Employing Blocked Nucleic Acids

Figure 3A:
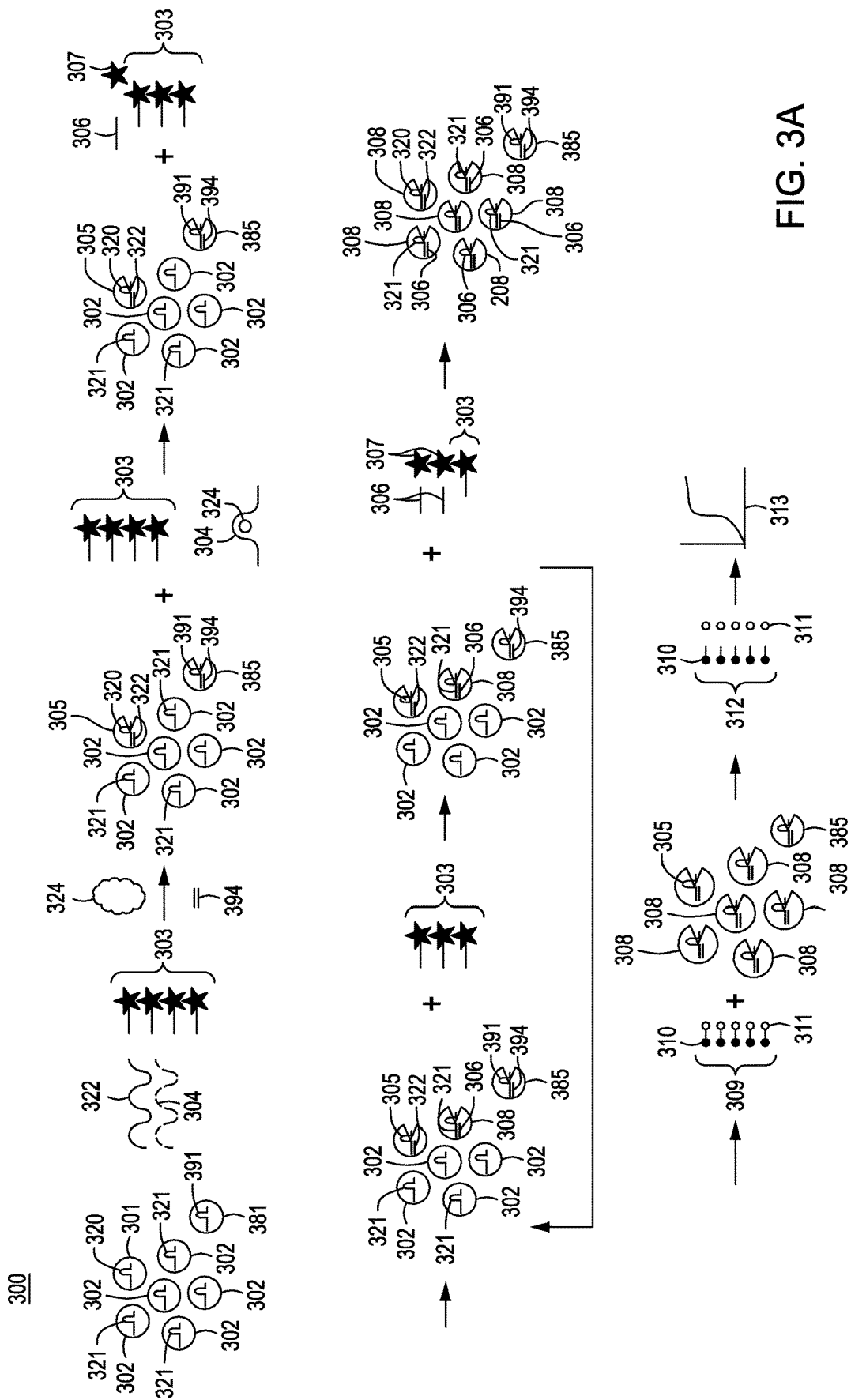
FIG. 3A is a diagram showing an exemplary cascade assay employing blocked nucleic acid molecules comprising three different ribonucleoprotein (RNP) complexes where one RNP complex is configured to detect a nucleic acid target of interest (RNP1-NA), one RNP complex is configured to detect a non-nucleic acid of interest (RNP1-NON), and one RNP complex provides a signal boost (RNP2).

FIG. 1, described above, depicts the cascade assay generally for detecting targets of interest. A specific embodiment 300 of the cascade assay for detecting both nucleic acid targets and non-nucleic acid targets of interest utilizing blocked nucleic acids is depicted in FIG. 3A and described in detail below. In this embodiment, a blocked nucleic acid is used to prevent the activation of RNP2 in the absence of a target of interest (nucleic acid target of interest and/or non-nucleic acid target of interest). Keep in mind that although the embodiment of the signal boost assay depicted in FIG. 3A is configured to detect both nucleic acid and non-nucleic acid targets of interest, that in some embodiments only non-nucleic acid targets of interest may be detected; that is, there may be only RNP1-NONs and no RNP1-NAs present in the reaction mix.

Method 300 in FIG. 3A begins with providing the cascade assay components 1) an RNP1 specific to detecting a non-nucleic acid target (RNP1-NON) 301 via an aptamer-complement 322, where the RNP1-NON 301 comprises a guide nucleic acid (gRNA1-NON) 320 complementary to the aptamer-complement 322 (only one RNP1-NON is shown); 2) an RNP1 specific to detecting a nucleic acid target (RNP1-NA) 381, where the RNP1-NA 381 comprises a guide nucleic acid (gRNA1-NA) 391 complementary to the nucleic acid target 394 (only one RNP1-NA is shown); 3) RNP2s 302 comprising gRNA2 321 (five are shown); 4) blocked nucleic acid molecules 303 (where the star represents a blocking moiety); 5) a double-stranded aptamer/aptamer-complement 304/322 where the aptamer/aptamer-complement 304/322 comprises aptamer 304 and aptamer-complement strand 322. RNP1-NON 301 comprises a gRNA (gRNA1-NON 320) specific for the aptamer-complement 322 and a nucleic acid-guided nuclease (e.g., Cas 12a or Cas 14 for a DNA aptamer-complement or a Cas 13a for an RNA aptamer-complement), RNP1-NA 381 comprises a gRNA (gRNA1-NA) specific for a nucleic acid target of interest 394 and a nucleic acid-guided nuclease (e.g., Cas 12a or Cas 14 for a DNA nucleic acid target of interest or a Cas 13a for an RNA nucleic acid of interest) and RNP2 302 comprises a gRNA2 321 specific for an unblocked nucleic acid molecule 306 and a nucleic acid-guided nuclease (again, Cas 12a or Cas 14 for a DNA unblocked nucleic acid molecule or a Cas 13a for an RNA unblocked nucleic acid molecule). In this embodiment of the cascade assay, the nucleic acid-guided nucleases in RNP1-NON 301, RNP1-NA 381, and RNP2 302 can be the same or different depending on the type of nucleic acid target, aptamer-complement and unblocked nucleic acid molecule; what is key, however, is that the nucleic acid-guided nucleases in RNP1-NON, RNP1-NA, and RNP2 may be activated to have trans-cleavage activity following binding of their respective targets (i.e., a non-nucleic acid of interest, a nucleic acid of interest, or an unblocked nucleic acid molecule, respectively).

In a first step, a sample that may comprise a nucleic acid target of interest and/or a non-nucleic acid target of interest is added to the reaction mixture, which may include (as it does here) a nucleic acid target of interest 394 and a non-nucleic acid target of interest 324. The double-strand aptamer 304/aptamer-complement 322 dehybridizes when the aptamer 304 binds the non-nucleic acid target of interest 324, leaving the aptamer-complement 322 free to combine with and activate RNP1-NON (301→305) as the gRNA1-NON 320 comprises a sequence complementary to the aptamer-complement 322. Aptamer-complement 322, however, does not interact with or activate RNP2 302. In addition to detecting the non-nucleic acid target of interest, the target strand of a nucleic acid target of interest 394 combines with and activates RNP1-NA (381→385) as the gRNA1-NA 391 comprises a sequence complementary to the target strand of the nucleic acid target of interest 394. The nucleic acid target of interest 394, however, does not interact with or activate RNP2 302.

Once RNP1-NON 305 binds aptamer-complement 322, RNP1-NON 305 cuts the aptamer-complement 322 via sequence-specific cis-cleavage and non-specific trans-cleavage by RNP1-NON 305 of other nucleic acids present in the reaction mixture is triggered as well, including blocked nucleic acid molecules 303. The same is true for RNP1-NA. Once RNP1-NA 385 binds nucleic acid target of interest 394, RNP1-NA 385 cuts the nucleic acid target of interest 394 via sequence-specific cis-cleavage and non-specific trans-cleavage by RNP1-NA 385 of other nucleic acids present in the reaction mixture is also triggered, including trans-cleavage of blocked nucleic acid molecules 303. Due to the non-specific trans-cleavage activity of both RNP1-NON 305 and RNP1-NA 384, at least one of the blocked nucleic acid molecules 303 becomes an unblocked nucleic acid molecule 306 when the blocking moiety 307 is removed. As described below, "blocking moiety" may refer to nucleoside modifications, topographical configurations such as secondary structures, and/or structural modifications.

When at least one of the blocked nucleic acid molecules 303 is unblocked, the unblocked nucleic acid molecule 306 can then interact with and activate RNP2 (i.e., 302→308) by binding to gRNA2 321 of RNP2 302. Because the nucleic acid-guided nucleases in RNP1-NON 305, RNP1-NA 385 and RNP2 308 have both cis- and trans-cleavage activity, more blocked nucleic acid molecules 303 become unblocked nucleic acid molecules 306 triggering activation of more RNP2s 308 and more trans-cleavage activity in a cascade. Note that the embodiment for non-nucleic acid detection shown in FIG. 2A is exemplified in FIG. 3A; however, the embodiment shown in and described in relation to FIG. 2D could be used as well. That is, RNP1-NON 301 would comprise a gRNA1-NON 320 complementary to a target strand 283 of the masked molecule region 282 of the aptamer/masked molecule compound molecule 280 from FIG. 2D.

FIG. 3A at bottom depicts the concurrent activation of reporter moieties. Intact reporter moieties 309 comprise a quencher 310 and a fluorophore 311 linked by a nucleic acid sequence. As described above in relation to FIG. 1, the reporter moieties are also subject to trans-cleavage by activated RNP1-NON 305, RNP1-NA 385 and RNP2 308. The intact reporter moieties 309 become unquenched reporter moieties 312 when the quencher 310 is separated from the fluorophore 311, emitting a fluorescent signal 313. Signal strength increases rapidly as more blocked nucleic acid molecules 303 become unblocked nucleic acid molecules 306 triggering cis-cleavage activation of more RNP2s 308 and thus more trans-cleavage activity of the reporter moieties 309. Again, here the reporter moieties are shown as separate molecules from the blocked nucleic acid molecules, but other configurations may be employed and are discussed in relation to FIG. 6. One particularly advantageous feature of the cascade assay is that, with the exception of the aptamer/aptamer-complement and the gRNAs (i.e., gRNA1-NON and gRNA1-NA) in the RNP1s (i.e., RNP1-NON and RNP1-NA), the cascade assay components are modular in the sense that the components may stay the same no matter what target of interest are being detected.

Figure 3B:
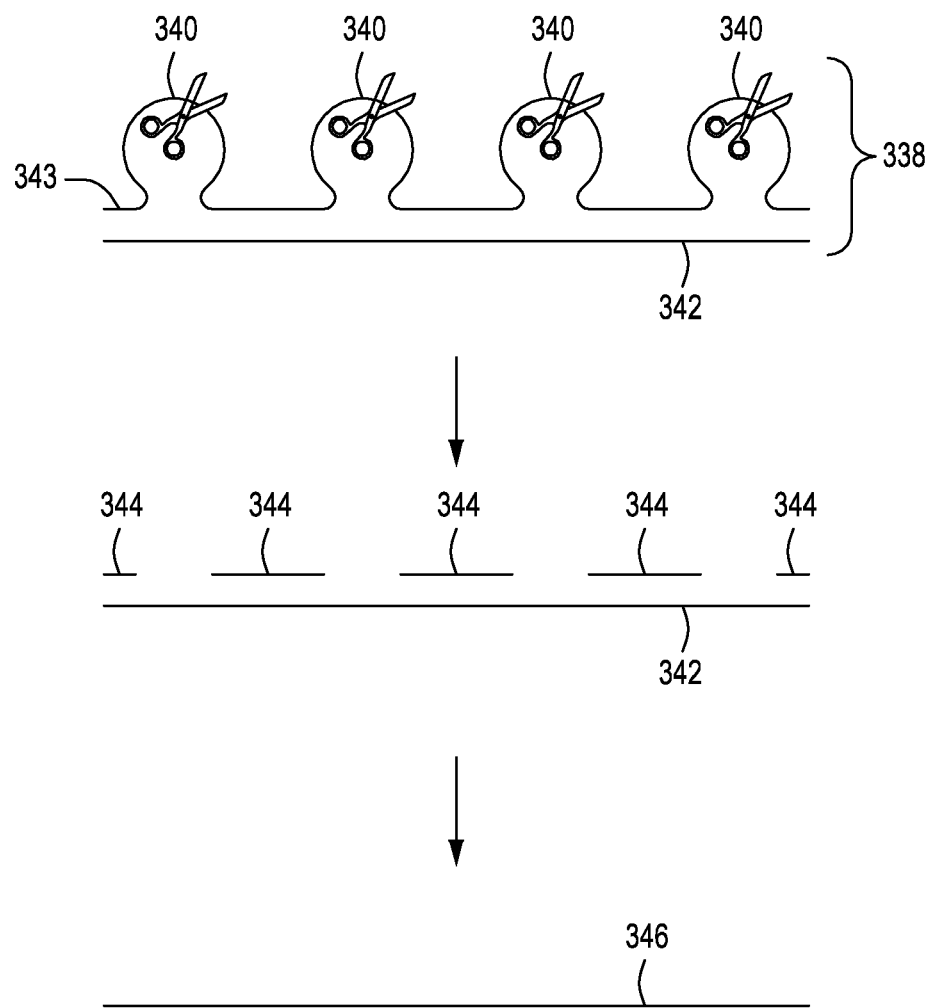
FIG. 3B is a diagram showing an exemplary blocked nucleic acid molecule and the concept behind unblocking some embodiments of the blocked nucleic acid molecules of the disclosure.

FIG. 3B is a diagram showing an exemplary blocked nucleic acid molecule 338 and an exemplary technique for unblocking the blocked nucleic acid molecules described herein. A blocked single-stranded or double-stranded, circular or linear, DNA or RNA molecule 338 comprising a target strand 342 may contain a partial hybridization with a complementary non-target strand nucleic acid molecule 343 containing unhybridized and cleavable secondary loop structures 340 (e.g., hairpin loops, tetraloops, pseudoknots, junctions, kissing hairpins, internal loops, bulges, and multibranch loops). Trans-cleavage of the loops by activated RNP1s or RNP2s generates short strand nucleotide sequences or regions 344 which, because of their short length and low melting temperature can dehybridize from target strand 342 at room temperature (e.g., 15°-25° C.), thereby unblocking the blocked nucleic acid molecule 338 to create an unblocked nucleic acid molecule 346, enabling the internalization of the unblocked nucleic acid molecule 346 (target strand) into an RNP2, leading to RNP2 activation.

Figure 3C:
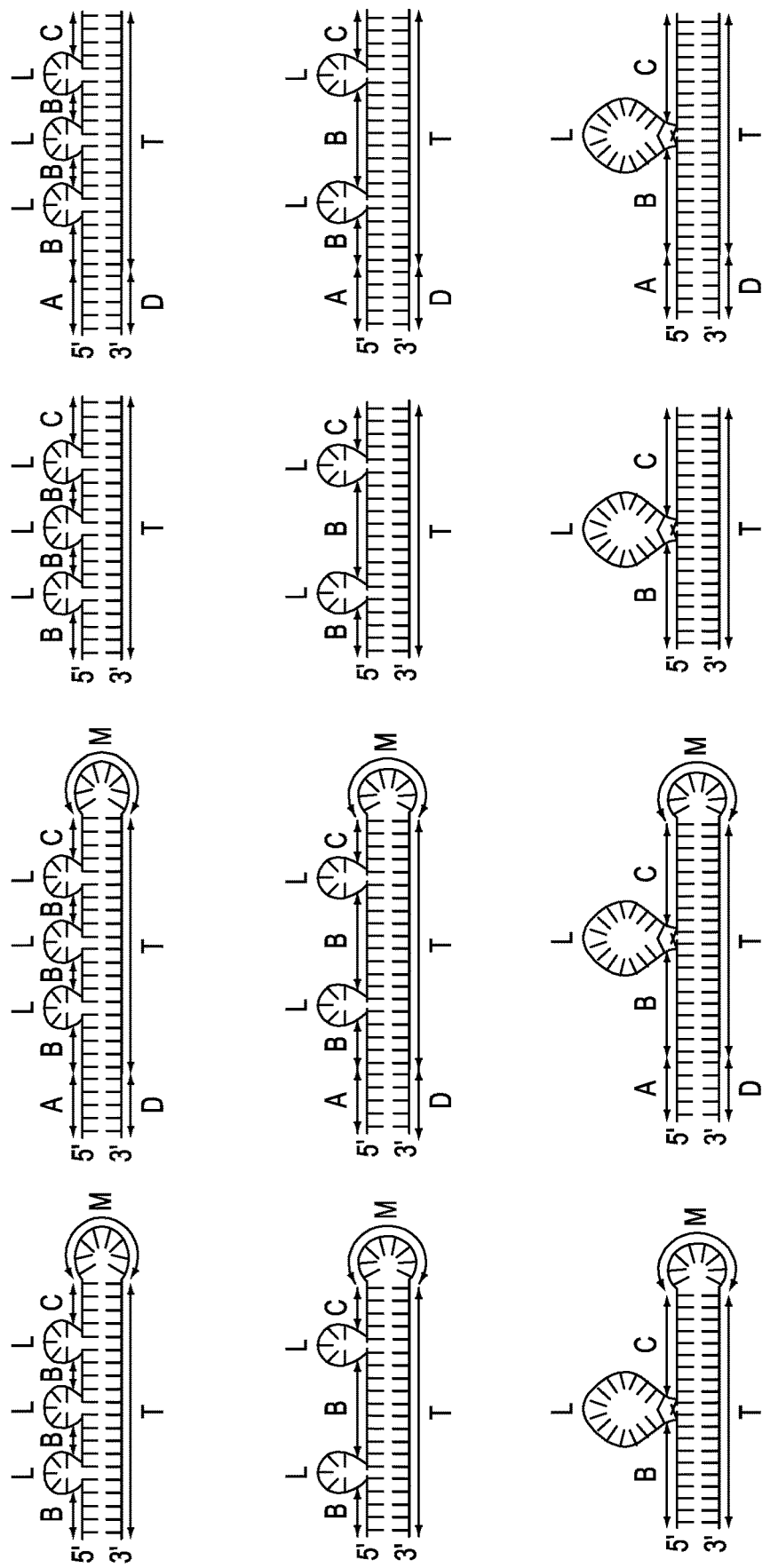
FIG. 3C shows schematics of several exemplary blocked nucleic acid molecules containing the structure of Formula I, as described herein.
Figure 3D:
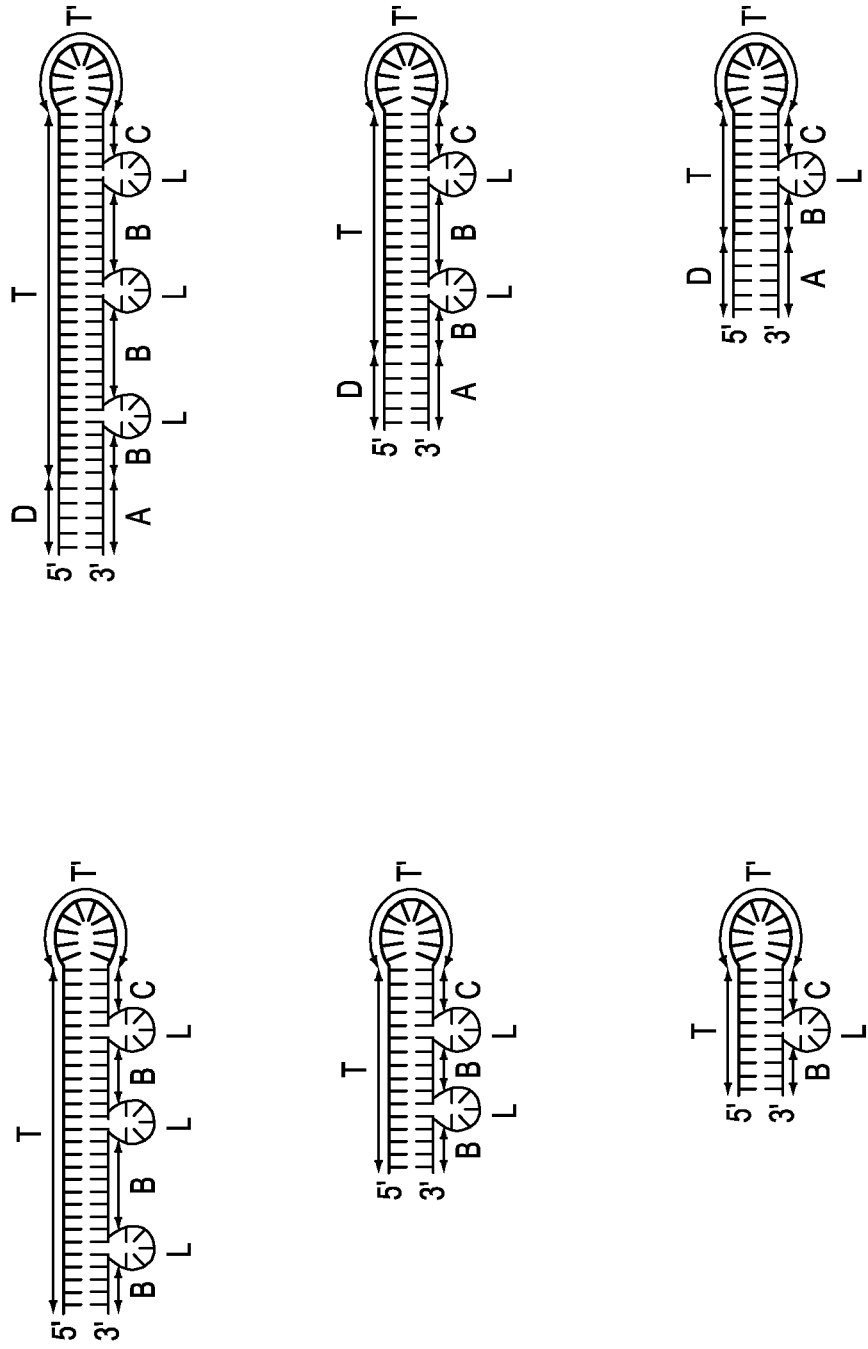
FIG. 3D shows schematics of several exemplary blocked nucleic acid molecules containing the structure of Formula II, as described herein.
Figure 3E:
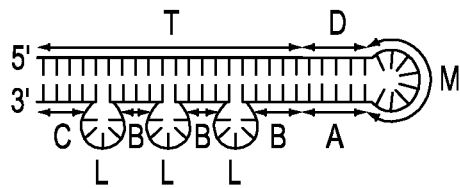
FIG. 3E shows schematics of several exemplary blocked nucleic acid molecules containing the structure of Formula III, as described herein.
Figure 3E:
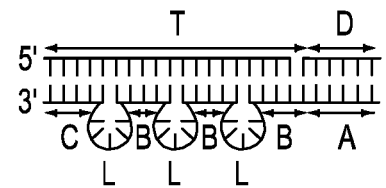
Figure 3E:
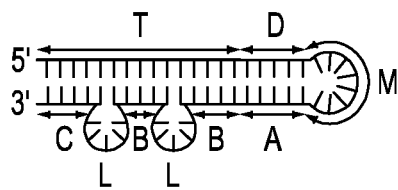
Figure 3E:
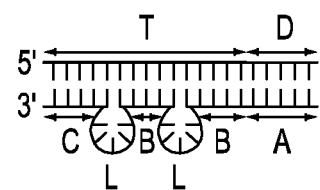
Figure 3E:
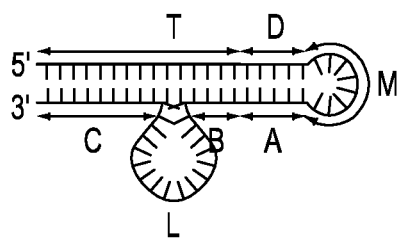
Figure 3E:
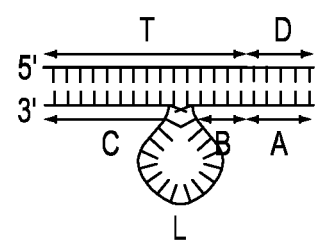
Figure 3F:
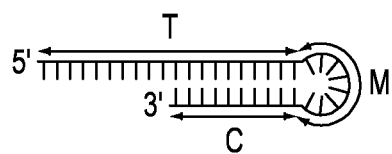
FIG. 3F shows schematics of two exemplary blocked nucleic acid molecules containing the structure of Formula IV, as described herein.
Figure 3F:
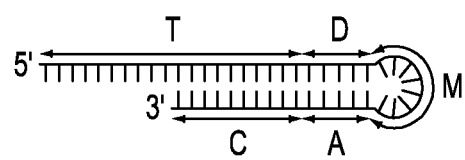

A blocked nucleic acid molecule may be single-stranded or double-stranded, circular or linear, and may further contain a partially hybridized nucleic acid sequence containing cleavable secondary loop structures, as shown in FIG. 3B and exemplified by "L" in FIGS. 3C-3E. Such blocked nucleic acids typically have a low binding affinity or high dissociation constant ($K_d$) in relation to binding to RNP2 and may be referred to herein as a high $K_d$ nucleic acid molecule. In the context of the present disclosure, the binding of blocked or unblocked nucleic acid molecules to RNP2, low $K_d$ values range from about 100 fM to about 1 aM or lower (e.g., 100 zM) and high $K_d$ values are in the range of 100 nM to about 10-100 10 mM and thus are about $10^5$-, $10^6$-, $10^7$-, $10^8$-, $10^9$- to $10^{10}$-fold or higher as compared to low $K_d$ values. Of course, the ideal blocked nucleic acid molecule would have an "infinite $K_d$."

Thus, the blocked nucleic acid molecules (high $K_d$ molecules) described herein can be converted into unblocked nucleic acid molecules (low $K_d$ molecules—also in relation to binding to RNP2) via cleavage of nuclease-cleavable regions (e.g., via active RNP1s (i.e., RNP1-NONs and RNP1-NAs) and RNP2s). The unblocked nucleic acid molecule has a higher binding affinity for the gRNA in RNP2 than does the blocked nucleic acid molecule. Once the unblocked nucleic acid molecule is bound to RNP2, RNP2 activation triggers trans-cleavage activity, which in turn leads to more RNP2 activation by further cleaving blocked nucleic acid molecules, resulting in a positive feedback loop or cascade.

In embodiments where blocked nucleic acid molecules are linear and/or form a secondary structure, the blocked nucleic acid molecules may be single-stranded (ss) or double-stranded (ds) and contain a first nucleotide sequence and a second nucleotide sequence. The first nucleotide sequence has sufficient complementarity to hybridize to a gRNA of RNP2, and the second nucleotide sequence does not. The first and second nucleotide sequences of a blocked nucleic acid molecule may be on the same nucleic acid molecule (e.g., for single-strand embodiments) or on separate nucleic acid molecules (e.g., for double-strand embodiments). Trans-cleavage (e.g., via RNP1 or RNP2) of the second nucleotide sequence in the blocked nucleic acid molecule converts the blocked nucleic acid molecule to a single-strand unblocked nucleic acid molecule. The unblocked nucleic acid molecule contains only the first nucleotide sequence, which has sufficient complementarity to hybridize to the gRNA of RNP2, thereby activating the trans-cleavage activity of RNP2.

In some embodiments, the second nucleotide sequence at least partially hybridizes to the first nucleotide sequence, resulting in a secondary structure containing at least one loop (e.g., hairpin loops, tetraloops, pseudoknots, junctions, kissing hairpins, internal loops, bulges, and multibranch loops) or two loops such as in "dumbbell" configurations. Such loops block the nucleic acid molecule from binding or incorporating into an RNP complex thereby initiating cis- or trans-cleavage (see, e.g., the exemplary structures in FIGS. 3C-3F).

In some embodiments, the blocked nucleic acid molecule may contain a protospacer adjacent motif (PAM) sequence, or partial PAM sequence, positioned between the first and second nucleotide sequences, where the first sequence is 5' to the PAM sequence, or partial PAM sequence. Inclusion of a PAM sequence may increase the reaction kinetics internalizing the unblocked nucleic acid molecule into RNP2 and thus decrease the time to detection. In other embodiments, the blocked nucleic acid molecule does not contain a PAM sequence.

In some embodiments, the blocked nucleic acid molecules (i.e., high $K_d$ nucleic acid molecules in relation to binding to RNP2) of the disclosure may include a structure represented by Formula I (e.g., FIG. 3C), Formula II (e.g., FIG. 3D), Formula III (e.g., FIG. 3E), or Formula IV (e.g., FIG. 3F) wherein Formulas I-IV are in the 5'-to-3' direction:

A-(B-L)$_J$-C-M-T-D (Formula I);
wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)$_J$-C and T-D are separate nucleic acid strands;
T is 17-135 nucleotides in length (e.g., 17-100, 17-50, or 17-25) and comprises a sequence complementary to B and C; and
D is 0-10 nucleotides in length and comprises a sequence complementary to A; and where, in some embodiments, segment A is attached to segment D forming a loop;

D-T-T'-C-(L-B)$_J$-A (Formula II);
wherein D is 0-10 nucleotides in length;
T-T' is 17-135 nucleotides in length (e.g., 17-100, 17-50, or 17-25);
T' is 1-10 nucleotides in length and does not hybridize with T;
C is 4-15 nucleotides in length and comprises a sequence complementary to T;
L is 3-25 nucleotides in length and does not hybridize with T;
B is 4-12 nucleotides in length and comprises a sequence complementary to T;
J is an integer between 1 and 10;
A is 0-15 nucleotides in length and comprises a sequence complementary to D; and where, in some embodiments, segment T is attached to segment B forming a loop;

T-D-M-A-(B-L)$_J$-C (Formula III);
wherein T is 17-135 nucleotides in length (e.g., 17-100, 17-50, or 17-25);
D is 0-10 nucleotides in length;
M is 1-25 nucleotides in length or is absent, wherein if M is absent then T-D and A-(B-L)$_J$-C are separate nucleic acid strands;
A is 0-15 nucleotides in length and comprises a sequence complementary to D;
B is 4-12 nucleotides in length and comprises a sequence complementary to T;
L is 3-25 nucleotides in length;
J is an integer between 1 and 10; and
C is 4-15 nucleotides in length;
and where, in some embodiments, segment T is attached to segment C forming a loop;

T-D-M-A-L$_p$-C (Formula IV);
wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

In alternative embodiments of any of these molecules, T (or T-T') can have a maximum length of 1000 nucleotides, e.g., at most 750, at most 500, at most 400, at most 300, at most 250, at most 200, at most 150, at most 135, at most 100, at most 75, at most 50, or at most 25 nucleotides.

Nucleotide mismatches can be introduced in any of the above structures containing double-strand segments (for example, where M is absent in Formula I or Formula III) to reduce the melting temperature ($T_m$) of the segment such that once the loop (L) is cleaved, the double-strand segment is unstable and dehybridizes rapidly. The percentage of nucleotide mismatches of a given segment may vary between 0% and 50%; however, the maximum number of nucleotide mismatches is limited to a number where the secondary loop structure still forms. "Segments" in the above statement refers to A, B, and C. In other words, the number of hybridized bases can be less than or equal to the length of each double-strand segment and vary based on number of mismatches introduced.

In any blocked nucleic acid molecule having the structure of Formula I, III, or IV, T will have sequence complementarity to a nucleotide sequence (e.g., a spacer sequence) within a gRNA of RNP2. The nucleotide sequence of T is to be designed such that hybridization of T to the gRNA of RNP2 activates the trans-nuclease activity of RNP2. In any blocked nucleic acid molecule having structure of Formula II, T-T' will have sequence complementarity to a sequence (e.g., a spacer sequence) within the gRNA of RNP2. The nucleotide sequence of T-T' is to be designed such that hybridization of T-T' to the gRNA of RNP2 activates the trans-nuclease activity of RNP2. For T or T-T', full complementarity to the gRNA is not necessarily required, provided there is sufficient complementarity to cause hybridization and trans-cleavage activation of RNP2.

In any of the foregoing embodiments, the blocked nucleic acid molecules of the disclosure may and preferably do further contain a reporter moiety attached thereto such that cleavage of the blocked nucleic acid releases a signal from the reporter moiety. (See FIG. 6, mechanisms depicted at center and bottom.)

Also, in any of the foregoing embodiments, the blocked nucleic acid molecule may be a modified or non-naturally occurring nucleic acid molecule. In some embodiments, the blocked nucleic acid molecules of the disclosure may further contain a locked nucleic acid (LNA), a bridged nucleic acid (BNA), and/or a peptide nucleic acid (PNA). The blocked nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, any other nucleic acid molecule modifications described above, and any combination thereof.

In some embodiments, the blocked nucleic acid molecules provided herein are circular DNAs, RNAs or chimeric (DNA-RNA) molecules, and the blocked nucleic acid molecules may include different base compositions depending on the Cas enzyme used for RNP1 and RNP2. For the circular design of blocked nucleic acid molecules, the 5' and 3' ends are covalently linked together. This configuration makes internalization of the blocked nucleic acid molecule into RNP2—and subsequent RNP2 activation—sterically unfavorable, thereby blocking the progression of the cascade assay. Thus, RNP2 activation (e.g., trans-cleavage activity) happens after cleavage of a portion of the blocked nucleic acid molecule followed by linearization and internalization of unblocked nucleic acid molecule into RNP2.

In some embodiments, the blocked nucleic acid molecules are topologically circular molecules with 5' and 3' portions hybridized to each other using DNA, RNA, LNA, BNA, or PNA bases which have a very high melting temperature ($T_m$). The high $T_m$ causes the structure to effectively behave as a circular molecule even though the 5' and 3' ends are not covalently linked. The 5' and 3' ends can also have base non-naturally occurring modifications such as phosphorothioate bonds to provide increased stability.

In embodiments where the blocked nucleic acid molecules are circularized (i.e., circular or topologically circular), each blocked nucleic acid molecule includes a first region, which is a target sequence specific to the gRNA of RNP2, and a second region, which is a sequence that can be cleaved by the nucleic acid-guided nucleases of activated RNP1 and/or RNP2. The first region may include a nuclease-resistant nucleic acid sequence such as, for example, a phosphorothioate group or other non-naturally occurring nuclease-resistant base modifications, for protection from trans-nucleic acid-guided nuclease activity. In some embodiments, when the Cas enzyme in both RNP1 and RNP2 is a Cas RNA-guided DNA nucleic acid-guided nuclease, the first region of the blocked nucleic acid molecule includes a nuclease-resistant DNA sequence, and the second region of the blocked nucleic acid molecule includes a cleavable DNA sequence. In other embodiments, when the Cas enzyme in RNP1 is a Cas RNA-guided DNA nucleic acid-guided nuclease and the Cas enzyme in RNP2 is a Cas RNA-guided RNA nucleic acid-guided nuclease, the first region of the blocked nucleic acid molecule includes a nuclease-resistant RNA sequence, and the second region of the blocked nucleic acid molecule includes a cleavable DNA sequence and a cleavable RNA sequence. In yet other embodiments, when the Cas enzyme in RNP1 is a Cas RNA-guided RNA nucleic acid-guided nuclease and the Cas enzyme in RNP2 is a Cas RNA-guided DNA nucleic acid-guided nuclease, the first region of the blocked nucleic acid molecule includes a nuclease-resistant DNA sequence, and the second region of the blocked nucleic acid molecule includes a cleavable DNA sequence and a cleavable RNA sequence. In some other embodiments, when the Cas enzyme in both RNP1 and RNP2 is a Cas RNA-guided RNA nucleic acid-guided nuclease, the first region of the blocked nucleic acid molecule includes a nuclease-resistant RNA sequence, and the second region of the blocked nucleic acid molecule includes a cleavable RNA sequence.

The Cascade Assay Employing Blocked Primer Molecules

The blocked nucleic acids described above may also, in an alternative embodiment, be blocked primer molecules. Blocked primer molecules include a sequence complementary to a primer binding domain (PBD) on a template molecule (see description below in reference to FIGS. 4A and 4B) and can have the same general structures as the blocked nucleic acid molecules described above. A PBD serves as a nucleotide sequence for primer hybridization followed by primer extension by a polymerase. In any of Formulas I, II, or III described above, the blocked primer nucleic acid molecule may include a sequence complementary to the PBD on the 5' end of T. The unblocked primer nucleic acid molecule can bind to a template molecule at the PBD and copy the template molecule via polymerization by a polymerase.

Figure 4A:
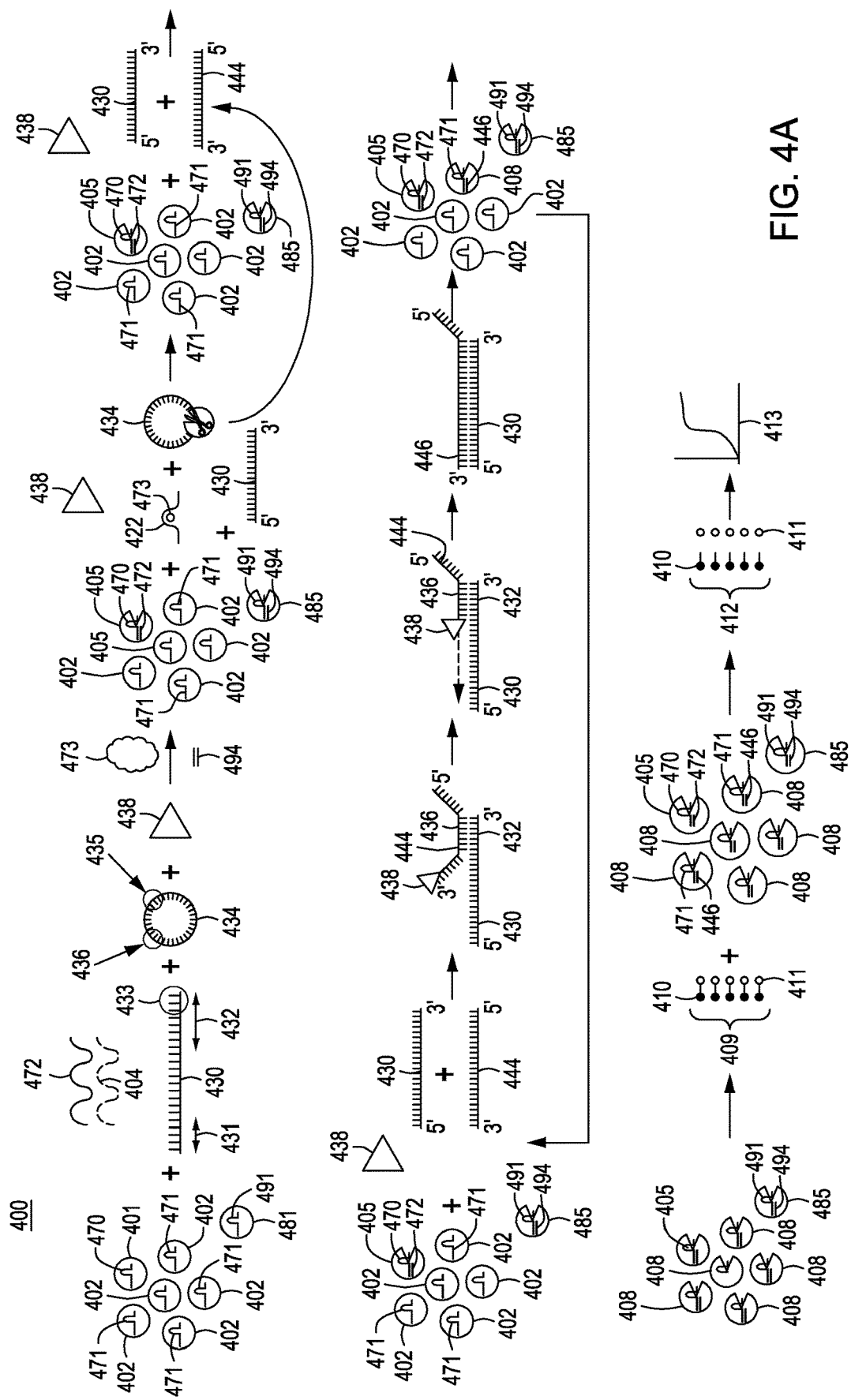
FIG. 4A is a diagram showing an exemplary cascade assay employing blocked primer molecules comprising three different ribonucleoprotein (RNP) complexes where one RNP complex is configured to detect a nucleic acid target of interest (RNP1-NA), one RNP complex is configured to detect a non-nucleic acid of interest (RNP1-NON), and one RNP complex provides a signal boost (RNP2).
Figure 4B:
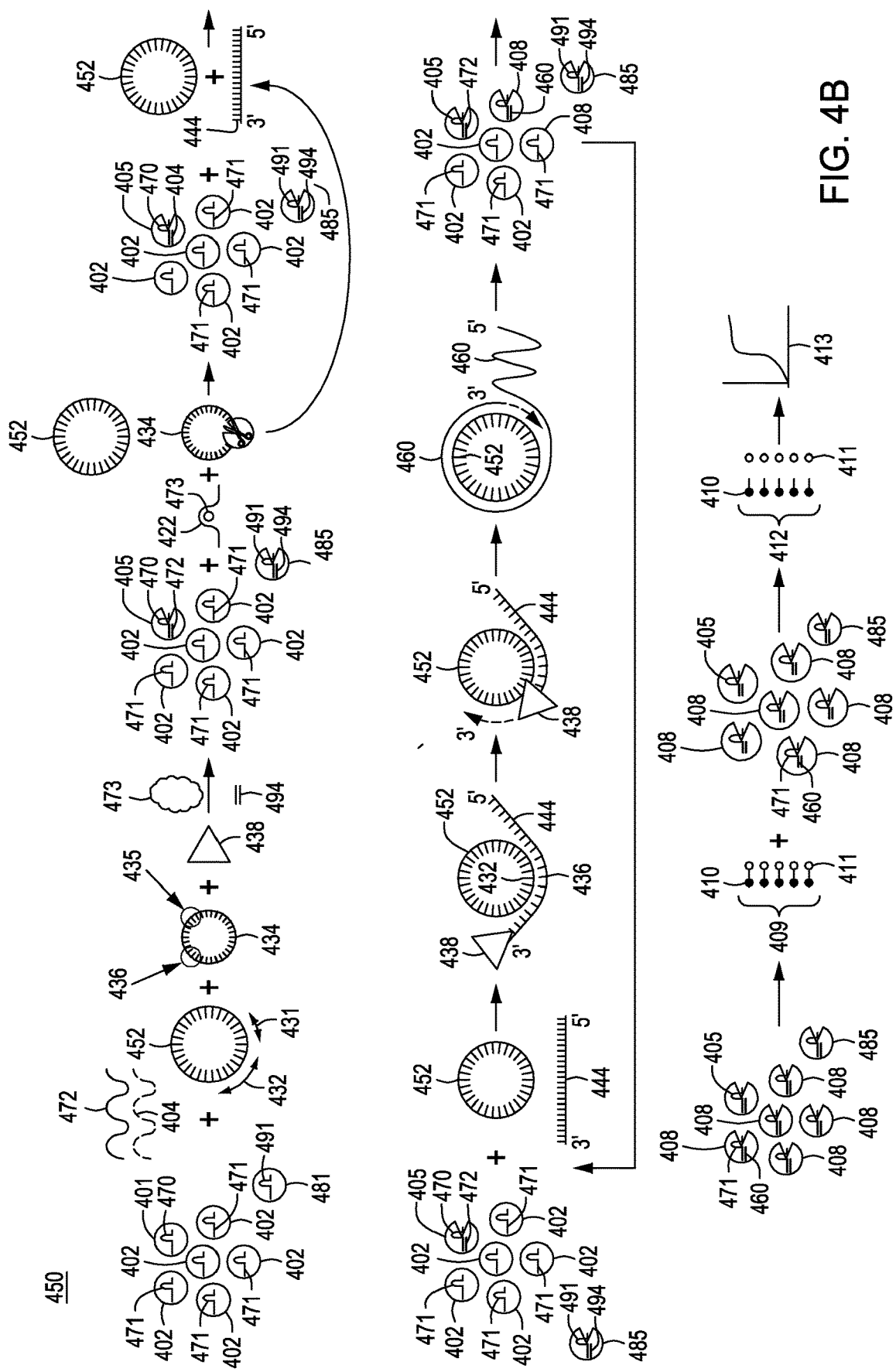
FIG. 4B is a diagram showing an alternative exemplary cascade assay employing blocked primer molecules comprising three different ribonucleoprotein (RNP) complexes where one RNP complex is configured to detect a nucleic acid target of interest (RNP1-NA), one RNP complex is configured to detect a non-nucleic acid of interest (RNP1-NON), and one RNP complex provides a signal boost (RNP2).

Specific embodiments of the signal boost cascade assay that utilize blocked primer molecules and are depicted in FIGS. 4A and 4B. As with the signal boost cascade assay depicted in FIG. 3A above, keep in mind that although the embodiments of the signal boost assay depicted in FIGS. 4A and 4B are configured to detect both nucleic acid and non-nucleic acid targets of interest, in some embodiments only non-nucleic acid targets of interest may be detected; that is, there may be only RNP1-NONs and no RNP1-NAs present in the reaction mixes.

In the embodiments using blocked nucleic acid molecules described above, activation of RNP1-NON and RNP1-NA and trans-cleavage of the blocked nucleic acid molecules were used to activate RNP2—that is, the unblocked nucleic acid molecules are a target sequence for the gRNA in RNP2. In contrast, in the embodiments using blocked primers, activation of RNP1-NON and RNP1-NA and the attendant trans-cleavage unblocks a blocked primer molecule that is then used to prime a template molecule for extension by a polymerase, thereby synthesizing activating nucleic acids that are the target sequence for the gRNA in RNP2.

FIG. 4A is a diagram showing the sequence of steps in an exemplary cascade assay 400 involving circular blocked primer molecules and linear template molecules. At left of FIG. 4A is a cascade assay reaction mixture comprising 1) an RNP1 specific to detecting a non-nucleic acid target (RNP1-NON) 401 via an aptamer-complement 472, where the RNP1-NON 401 comprises a guide nucleic acid (gRNA1-NON) 470 complementary to the aptamer-complement 472 (only one RNP1-NON 401 is shown); 2) an RNP1 specific to detecting a nucleic acid target (RNP1-NA) 481, where the RNP1-NA 481 comprises a guide nucleic acid (gRNA1-NA) 491 complementary to the nucleic acid target 494 (only one RNP1-NA 481 is shown); 3) RNP2s 402 (five are shown, each comprising a gRNA2 471); 4) linear template molecules 430 (which is the non-target strand); 5) a circular blocked primer molecule 434 (i.e., a high $K_d$ molecule); 6) an aptamer 404/aptamer-complement 472 double-stranded molecule; and 7) a polymerase (438), such as a (D29 polymerase. The linear template molecule 430 (non-target strand) comprises an optional PAM sequence 431, a primer binding domain (PBD) 432 and, optionally, a nucleoside modification 433 to protect the linear template molecule 430 from 3'→5' exonuclease activity. Blocked primer molecule 434 comprises a cleavable region 435 and a complement region 436 to the PBD 432 on the linear template molecule 430.

Upon addition of a sample comprising a nucleic acid target of interest 494 and a non-nucleic acid target of interest 473, the nucleic acid target of interest 494 binds gRNA1-NA 491 thereby activating RNP1-NA (481→485); and the non-nucleic acid target of interest 473 binds to aptamer 404, leaving the aptamer-complement 472 free to bind to gRNA1-NON 470 thereby activating RNP1-NON (401→405). Once activated, RNP1-NON 405 and RNP1-NA 485 cut the aptamer-complement 472 and nucleic acid target of interest 494, respectively, via sequence specific cis-cleavage, and non-specific trans-cleavage of other nucleic acids present in the reaction mixture takes place, including trans-cleavage of at least one of the blocked primer molecules 434. The circular blocked primer molecule 434 (i.e., a high $K_d$ molecule, where high $K_d$ relates to binding to the template molecule 430) upon cleavage becomes an unblocked linear primer molecule 444 (a low $K_d$ molecule, where low $K_d$ relates to binding to the template molecule 430), which has a region 436 complementary to the PBD 432 on the linear template molecule 430 and can bind to the linear template molecule 430.

Once the unblocked linear primer molecule 444 and the linear template molecule 430 are hybridized (i.e., hybridized at the PBD 432 of the linear template molecule 430 and the PBD complement region 436 on the unblocked linear primer molecule 444), 3'→5' exonuclease activity of the polymerase 438 removes the unhybridized single-stranded DNA at the end of the unblocked primer molecule 444 and the polymerase 438 can use the linear template molecule 430 to produce a synthesized activating nucleic acid 446 which is a complement of the linear template molecule and serves as a target strand. The synthesized activating nucleic acid 446 activates RNP2 (402→408). As described above, because the nucleic acid-guided nuclease in the RNP2 408 complex exhibits (that is, possesses) both cis- and trans-cleavage activity, more blocked primer molecules 434 become unblocked primer molecules 444 triggering activation of more RNP2s (402→408) and more trans-cleavage activity in a cascade. Note that the embodiment for non-nucleic acid detection shown in FIG. 2A is exemplified in FIG. 4A; however, the embodiment shown in and described in relation to FIG. 2D could be used as well. That is, RNP1-NON 401 would comprise a gRNA1-NON 470 complementary to a target strand 283 of the masked molecule region 282 of the aptamer/masked molecule compound molecule 280 from FIG. 2D.

FIG. 4A at bottom depicts the concurrent activation of reporter moieties. Intact reporter moieties 409 comprise a quencher 410 and a fluorophore 411. As described above in relation to FIG. 1, the reporter moieties are also subject to trans-cleavage by activated RNP1-NON 405, RNP1-NA 485, and RNP2 408. The intact reporter moieties 409 become activated reporter moieties 412 when the quencher 410 is separated from the fluorophore 411, and the fluorophore emits a fluorescent signal 413. Signal strength increases rapidly as more blocked primer molecules 434 become unblocked primer molecules 444 generating synthesized activating nucleic acids 446 and triggering activation of more RNP2s 408 and more trans-cleavage activity of the reporter moieties 409. Again, here the reporter moieties are shown as separate molecules from the blocked nucleic acid molecules, but other configurations may be employed and are discussed in relation to FIG. 6. Also, as with the cascade assay embodiment utilizing blocked nucleic acid molecules that are not blocked primers, with the exception of the gRNAs in RNP1-NA and RNP1-NON and the aptamer/aptamer-complement, the cascade assay components stay the same no matter what non-nucleic acid target(s) of interest are being detected.

FIG. 4B is a diagram showing the sequence of steps in an exemplary cascade assay 450 involving circular blocked primer molecules 434 and circular template molecules 452. The cascade assay of FIG. 4B differs from that depicted in FIG. 4A by the configuration of the template molecule. Where the template molecule in FIG. 4A was linear, in FIG. 4B the template molecule is circular. At left of FIG. 4B is a cascade assay reaction mixture comprising 1) an RNP1 specific to detecting a non-nucleic acid target (RNP1-NON) 401 via an aptamer-complement 472, where the RNP1-NON 401 comprises a guide nucleic acid (gRNA1-NON) 470 complementary to the aptamer-complement 472 (only one RNP1-NON 401 is shown); 2) an RNP1 specific to detecting a nucleic acid target (RNP1-NA) 481, where the RNP1-NA 481 comprises a guide nucleic acid (gRNA1-NA) 491 complementary to the nucleic acid target 494 (only one RNP1-NA 401 is shown); 3) RNP2s 402 (five are shown, each comprising gRNA2 471); 4) circular template molecule 452 (which is the non-target strand); 5) a circular blocked primer molecule 434 (i.e., the high $K_d$ molecule); 6) an aptamer 404/aptamer-complement 472 double-strand molecule; and 7) a polymerase 438, such as a (D29 polymerase. The circular template molecule 452 (non-target strand) comprises a PAM sequence 431 and a primer binding domain (PBD) 432. Circular blocked primer molecule 434 comprises a cleavable region 435 and a complement region 436 to the PBD 432 on the circular template molecule 452.

Upon addition of a sample comprising a nucleic acid target of interest 494 and a non-nucleic acid target of interest 473 capable of complexing with aptamer 404, the nucleic acid target of interest 494 binds gRNA1-NA 491 thereby activating RNP1-NA (481→485); and the aptamer-complement 472 is available to complex with gRNA-NON 470 in RNP1-NON 401. When the nucleic acid target of interest 494 binds to gRNA1-NA 491 thereby activating RNP1-NA (481→485) and aptamer-complement 472 binds to gRNA1-NON 470 thereby activating RNP1 (401→405) the nucleic acid target of interest 494 and the aptamer-complement 472 are cleaved via sequence specific cis-cleavage and non-specific trans-cleavage of other nucleic acids begins as well, including trans-cleavage of at least one of the blocked primer molecules 434. The circular blocked primer molecule 434, upon cleavage, becomes an unblocked linear primer molecule 444, which has a region 436 complementary to the PBD 432 on the circular template molecule 452 and can hybridize with the circular template molecule 452.

Once the unblocked linear primer molecule 444 and the circular template molecule 452 are hybridized (i.e., hybridized at the PBD 432 of the circular template molecule 452 and the PBD complement region 436 on the unblocked linear primer molecule 444), 3'→5' exonuclease activity of the polymerase 438 removes the unhybridized single-stranded DNA at the 3' end of the unblocked primer molecule 444. The polymerase 438 can now use the circular template molecule 452) (non-target strand) to produce concatenated activating nucleic acids 460 (which are concatenated target strands), which will be cleaved by the trans-cleavage activity of activated RNP1 405. The cleaved regions of the concatenated synthesized activating nucleic acids 460 (target strand) are capable of activating the RNP2 (402→408) complex.

As described above, because the nucleic acid-guided nuclease in RNP2 408 comprises both cis- and trans-cleavage activity, more blocked primer molecules 434 become unblocked primer molecules 444 triggering activation of more RNP2s 408 and more trans-cleavage activity in a cascade. Note that the embodiment for non-nucleic acid detection shown in FIG. 2A is exemplified in FIG. 4B; however, the embodiment shown in and described in relation to FIG. 2D could be used as well. That is, RNP1-NON 401 would comprise a gRNA1-NON 470 complementary to a target strand 283 of the masked molecule region 282 of the aptamer/masked molecule compound molecule 280 from FIG. 2D.

FIG. 4B at bottom depicts the concurrent activation of reporter moieties. Intact reporter moieties 409 comprise a quencher 410 and a fluorophore 411. As described above in relation to FIG. 1, the reporter moieties are also subject to trans-cleavage by activated RNP1-NON 405, RNP1-NA 485, and RNP2 408. The intact reporter moieties 409 become activated reporter moieties 412 when the quencher 410 is separated from the fluorophore 411, and the fluorescent signal 413 is unquenched and can be detected. Signal strength increases rapidly as more blocked primer molecules 434 become unblocked primer molecules 444 generating synthesized activating nucleic acids and triggering activation of more RNP2s 408 and more trans-cleavage activity of the reporter moieties 409. Again, here the reporter moieties are shown as separate molecules from the blocked nucleic acid molecules, but other configurations may be employed and are discussed in relation to FIG. 6. Also note that as with the other embodiments of the cascade assay, in this embodiment, with the exception of the aptamer/aptamer-complement and the first gRNA in RNP1, the cascade assay components stay the same no matter what non-nucleic acid target(s) of interest are being detected.

The polymerases used in the "blocked primer molecule" embodiments serve to polymerize a reverse complement strand of the template molecule (non-target strand) to generate a synthesized activating nucleic acid (target strand) as described above. In some embodiments, the polymerase is a DNA polymerase, such as a BST, T4, or Therminator polymerase (New England BioLabs Inc., Ipswich MA., USA). In some embodiments, the polymerase is a Klenow fragment of a DNA polymerase. In some embodiments the polymerase is a DNA polymerase with 5'→3' DNA polymerase activity and 3'→5' exonuclease activity, such as a Type I, Type II, or Type III DNA polymerase. In some embodiments, the DNA polymerase, including the Phi29, T7, Q5®, Q5U®, Phusion®, OneTaq®, LongAmp®, Vent®, or Deep Vent® DNA polymerases (New England BioLabs Inc., Ipswich MA., USA), or any active portion or variant thereof. Also, a 3' to 5' exonuclease can be separately used if the polymerase lacks this activity.

The Cascade Assay Employing Blocked Guide (gRNA2) Nucleic Acids

Figure 5A:
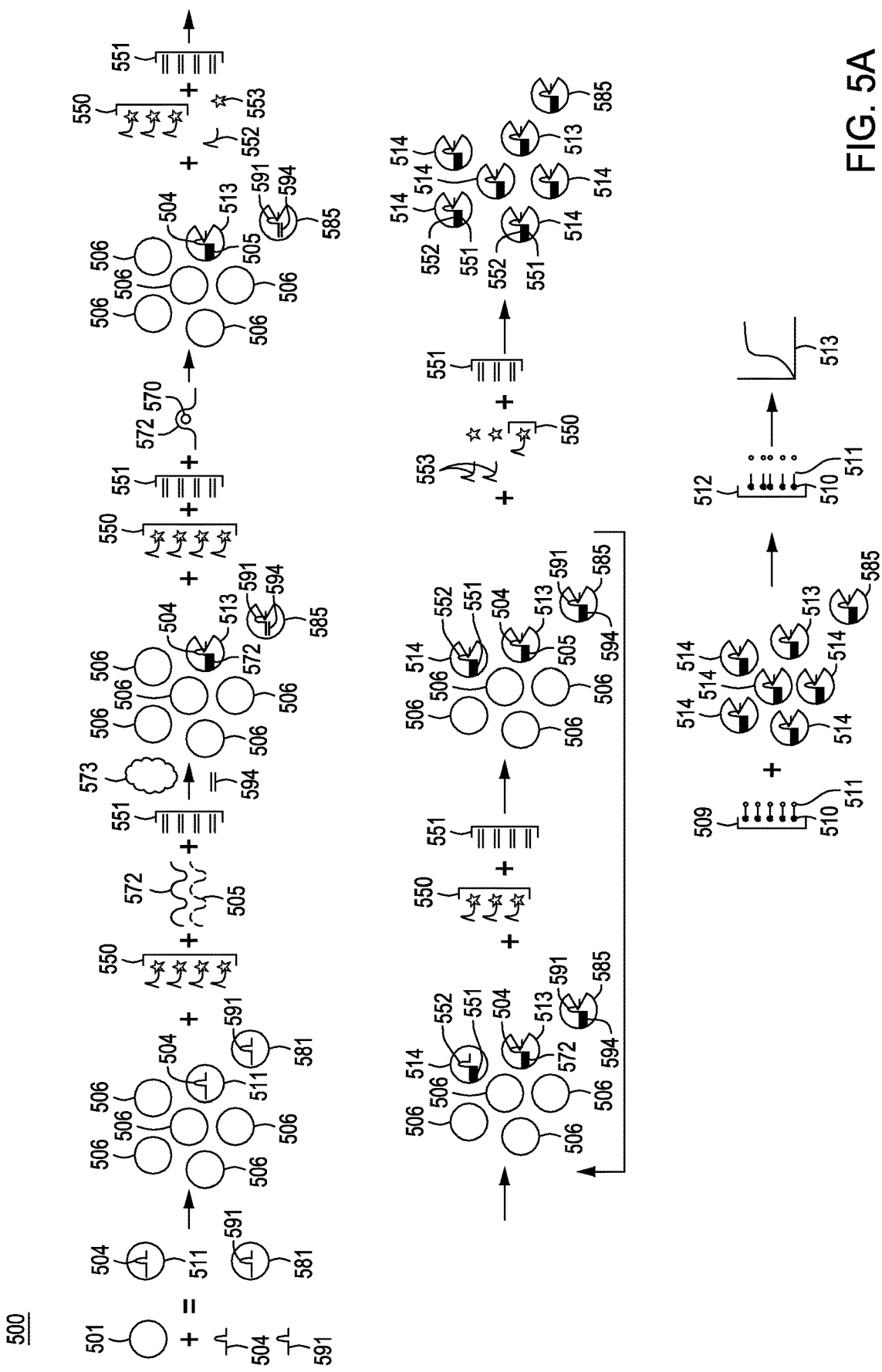
FIG. 5A is a diagram showing yet another alternative exemplary cascade assay employing blocked guide molecules comprising three different ribonucleoprotein (RNP) complexes where one RNP complex is configured to detect a nucleic acid target of interest (RNP1-NA), one RNP complex is configured to detect a non-nucleic acid of interest (RNP1-NON), and one RNP complex provides a signal boost (RNP2).

FIG. 5A is a diagram showing the sequence of steps in an exemplary cascade assay for detecting nucleic acid and non-nucleic acid targets of interest using blocked guide nucleic acids (gRNA). In this embodiment, instead of a blocked nucleic acid molecule or a blocked primer molecule, a blocked guide nucleic acid (i.e., a blocked guide RNA or blocked gRNA) complementary to an RNP2 activating nucleic acid and complexed with a second nucleic acid-guided nuclease is used to form RNP2. The blocked guide nucleic acid functions like the blocked nucleic acid molecules and the blocked primer molecules to "lock" RNP2 unless and until a nucleic acid target of interest and/or a non-nucleic acid target of interest is present. The trans-cleavage activity of an activated RNP1-NA or RNP1-NON then unblocks the blocked guide nucleic acids which can then complex with the second nucleic acid-guided nuclease to form second ribonucleoprotein complexes (i.e., RNP2s) which are then activated. Again, although the embodiment of the signal boost assay depicted in this FIG. 5A is configured to detect both nucleic acid and non-nucleic acid targets of interest, in some embodiments only non-nucleic acid targets of interest may be detected.

FIG. 5A is a diagram showing the sequence of steps in an exemplary cascade assay involving blocked guide nucleic acids. In this embodiment, a blocked guide nucleic acid (i.e., blocked gRNA2) is used to prevent the activation of RNP2 in the absence of detection of a target of interest. The cascade assay 500 in FIG. 5A begins with providing a first nucleic acid-guided nucleases 501 and guide nucleic acids to detect non-nucleic acid targets (gRNA1-NONs) 504, which combine to form RNP1-NONs 511 (only one is shown) and providing first nucleic acid-guided nucleases 501 and guide nucleic acids to detect nucleic acid targets (gRNA1-NAs) 591, which combine to form RNP1-NAs 581. Alternatively, as shown in FIGS. 3A, 4A and 4B, RNP1-NON 511 and RNP1-NA 581 can be pre-formed prior to addition to the reaction mixture. Added to the RNP1-NONs 511 and RNP1-NAs 581 are 1) second nucleic acid-guided nucleases 506; 2) blocked guide nucleic acids (blocked gRNA2s) 550; 3) RNP2 activating nucleic acids 551; 4) aptamer 505/aptamer-complement 572 constructs; and 8) reporter moieties 509 (seen only at bottom of FIG. 5A). The RNP2s that are formed comprise the second nucleic acid-guided nucleases 506 and unblocked gRNA2s 552 (550→552) that are specific for the RNP2 activating nucleic acids 551. The second nucleic acid-guided nuclease 506 may be, e.g., Cas 12a or Cas 14 for DNA RNP2 activating nucleic acids or, e.g., a Cas 13a for RNA RNP2 activating nucleic acids.

In a first step, RNP1-NON 511 is formed from a first nucleic acid-guided nuclease 501 and gRNA1-NON 504, where gRNA1-NON 504 is complementary to aptamer-complement 572. RNP1-NA 581 is formed from a first nucleic acid-guided nuclease 501 and gRNA1-NA 591, where gRNA1-NA 591 is complementary to the target strand of the nucleic acid target of interest 594. RNP1-NON 511 and RNP1-NA 581 are now in the reaction mixture with second nucleic acid-guided nuclease 506; RNP2 activating nucleic acids 551; blocked guide nucleic acids 550; aptamer 505 and aptamer-complement 572. RNP1-NON 511 now can bind to aptamer-complement 572 causing cis-cleavage of the aptamer-complement 572 and creating an activated RNP1-NON 513 (511→513), and RNP1-NA 581 now can bind to nucleic acid target of interest 594 creating an activated RNP1-NA 585 (581→585), which in turn initiates cis-cleavage of the nucleic acid target of interest 594.

At this point, indiscriminate trans-cleavage activity by RNP1-NON 513 and RNP1-NA 585 of other nucleic acids in the reaction mixture is initiated, including at least one of the blocked gRNA2s 550. The blocked gRNA2s 550 (i.e., a high $K_d$ molecules, where high $K_d$ relates to binding to RNP2 activating nucleic acids 551) upon cleavage become unblocked gRNA2s 552 (a low $K_d$ molecule, where low $K_d$ relates to binding to RNP2 activating nucleic acids 551). Thus, at least one of the blocked gRNA2s 550 becomes an unblocked gRNA2 552 when the blocking moiety 553 is removed from the blocked gRNA2 550. As described above, "blocking moiety" may refer to nucleoside modifications, topographical configurations such as secondary structures, and/or structural modifications.

Once at least one of the blocked gRNA2s 550 is unblocked, the unblocked gRNA2 552 can then interact with second nucleic acid-guided nuclease 506 to form RNP2 512 which then complexes with RNP2 activating nucleic acids 551 cis-cleaving the RNP2 activating nucleic acids 551 and triggering trans-cleavage of more nucleic acids in the reaction mixture. Because the nucleic acid-guided nucleases in the activated RNP1-NONs 513, RNP1-NAs 585, and RNP2s 514 have both cis- and trans-cleavage activity, the trans-cleavage activity causes more blocked gRNA2s 550 to become unblocked gRNA2s 551 triggering activation of even more RNP2s 512 (512→514) and more trans-cleavage activity in a reaction cascade. Again note that the embodiment for non-nucleic acid detection shown in FIG. 2A is exemplified in FIG. 5A; however, the embodiment shown in and described in relation to FIG. 2D could be used as well. That is, RNP1-NON 511 would comprise a gRNA1-NON 591 complementary to a target strand 283 of the masked molecule region 282 of the aptamer/masked molecule compound molecule 280 from FIG. 2D.

FIG. 5A at bottom depicts the concurrent activation of reporter moieties. Intact reporter moieties 509 comprise a quencher 510 and a fluorophore 511 linked by a nucleic acid sequence. As described above in relation to FIG. 1, the intact reporter moieties 509 are also subject to trans-cleavage by activated RNP1-NON 513, RNP1-NA 585, and RNP2 512. The intact reporter moieties 509 become unquenched reporter moieties 512 when the quencher 510 is separated from the fluorophore 511, emitting a fluorescent signal 513. Signal strength increases rapidly as more blocked gRNA2s 550 become unblocked gRNA2s 552 triggering cis-cleavage activity of more RNP2s 512 and thus more trans-cleavage activity of the reporter moieties 509. Again, the reporter moieties are shown here as separate molecules from the blocked nucleic acid molecules, but other configurations may be employed and are discussed in relation to FIG. 6.

Figure 5B:
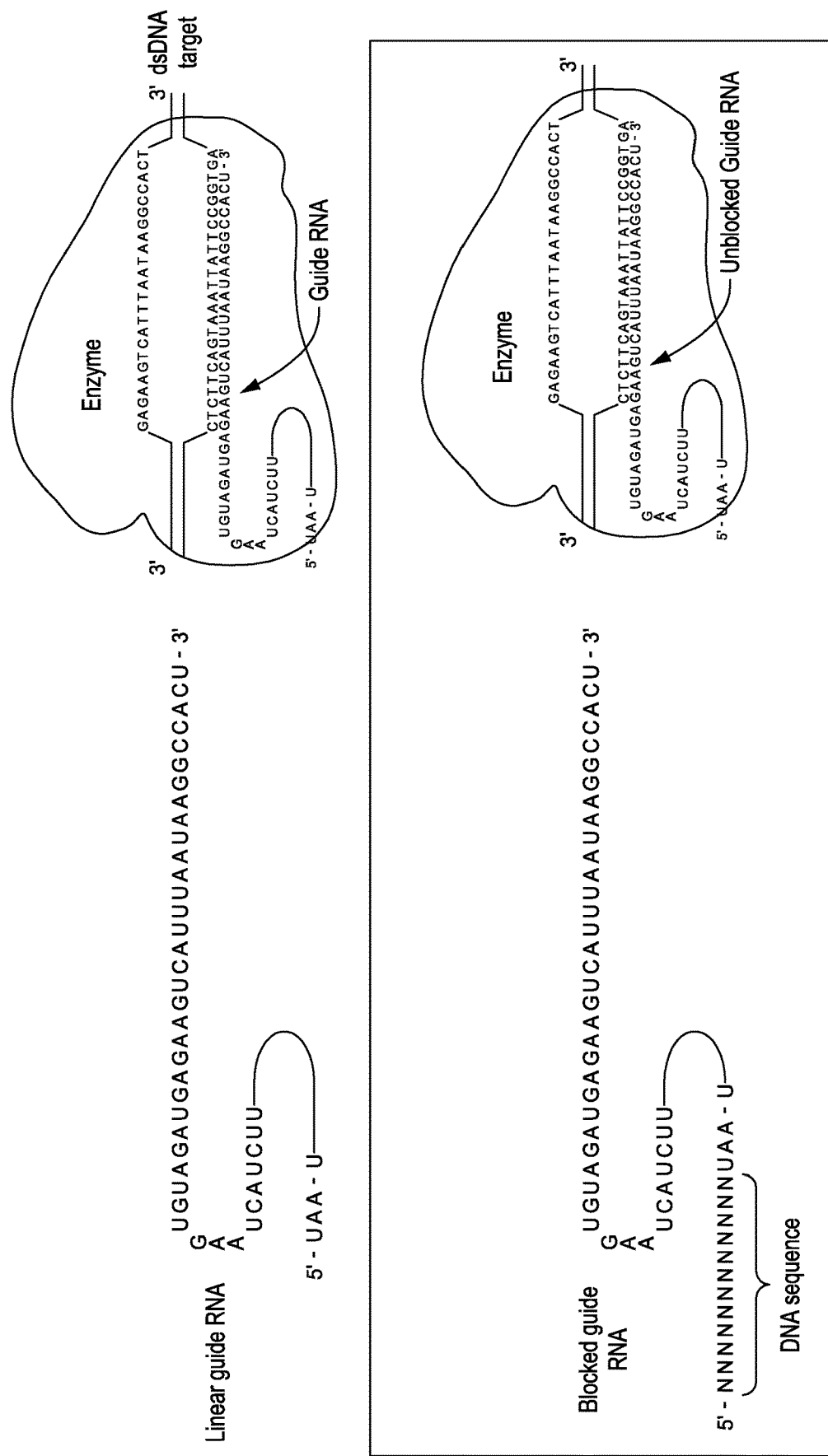
FIG. 5B shows an exemplary guide RNA design and an exemplary blocked guide RNA design.

FIG. 5B shows exemplary guide RNA designs; UAAUUCUACUAAGUGUAGAUGAGAAGU-CAUUUAAUAAGGCCACU is SEQ ID NO: 1; GAGAAGTCATTTAATAAGGCCACT is SEQ ID NO: 2; CTCTTCAGTAAATTATTCCGGTGA is SEQ ID NO: 3; NNNNNNNNNNNUAUUUCUACUAAGUGUA-GAUGAGAGUCAUUUAAUAAGGC CACU is SEQ ID NO: 4; and NNNNNNNNUAAUUUCUACUAAGUGUA-GAUGAGAAGUCAUUUAAUAAGGCC ACU is SEQ ID NO: 5.

Figure 5C:
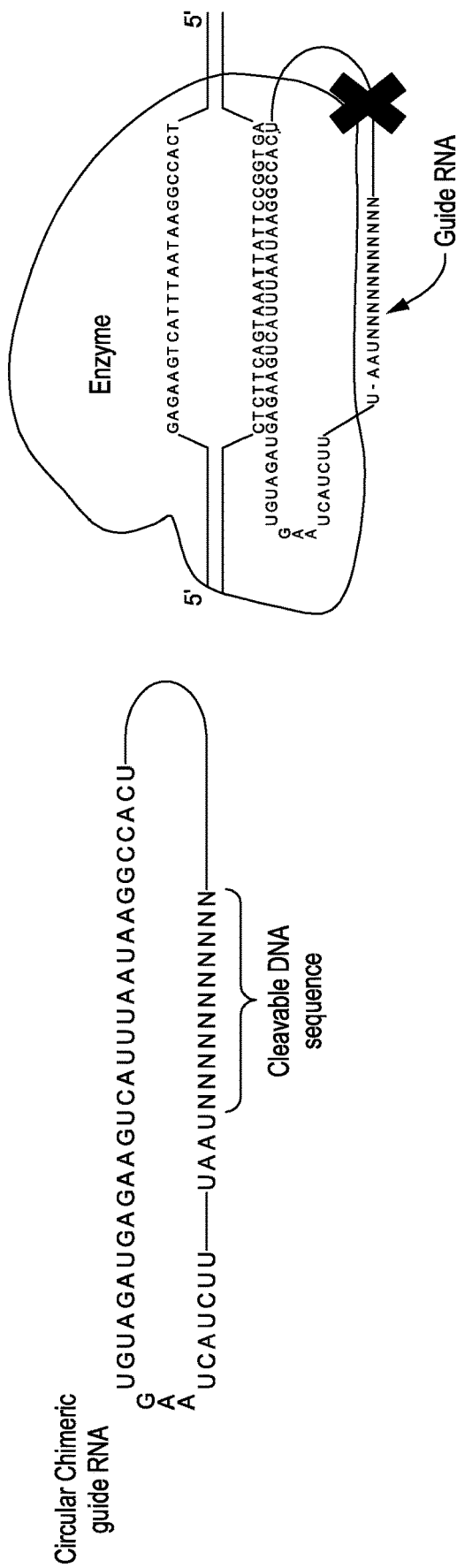
FIG. 5C shows exemplary gRNAs, both linear and circular.

FIG. 5C shows blocked guide RNAs, both linear and circular. The black lines show one phosphate linkage shown only for visualization of circular molecules; GAGAAGT-CATTTAATAAGGCCACT is SEQ ID NO: 6; CTCTTCAGTAAATTATTCCGGTGA is SEQ ID NO: 7; and NNNNNNNNNNNUAAUUUCUACUAAGUGUA-GAUGAGAAGUCAUUUAAUAAG GCCACU is SEQ ID NO: 8.

Reporter Moiety Configurations

FIG. 6 depicts three mechanisms in which a cascade assay reaction can release a signal from a reporter moiety. FIG. 6 at top shows the mechanism discussed in relation to FIGS. 3A, 4A, 4B, and 5A. In this embodiment, a reporter moiety 609 is a separate molecule from the blocked nucleic acid molecules (or blocked primer molecules) present in the reaction mixture. Reporter moiety 609 comprises a quencher 610 and a fluorophore 611. An unquenched reporter moiety 612 emits a signal from the fluorophore 611 once it has been physically separated from the quencher 610.

FIG. 6 at center shows a blocked nucleic acid molecule 603, which is also a reporter moiety. In addition to quencher 610 and fluorophore 611, a blocking moiety 607 can be seen. Blocked nucleic acid molecule/reporter moiety 603 comprises a quencher 610 and a fluorophore 611. In this embodiment of the cascade assay, when the blocked nucleic acid molecule 603 is unblocked due to trans-cleavage initiated by the nucleic acid target of interest binding to RNP1, the unblocked nucleic acid molecule 606 also becomes an unquenched reporter moiety with fluorophore 611 separated from quencher 610. Note both the blocking moiety 607 and the quencher 610 are removed. In this embodiment, the reporter signal is directly generated as the blocked nucleic acid molecules become unblocked. Embodiments of this schema can be used to supply the bulky modifications to the blocked nucleic acid molecules described below.

FIG. 6 at bottom shows that cis-cleavage of an unblocked nucleic acid molecule or a synthesized activating nucleic acid at a PAM distal sequence by RNP2 generates a signal. Shown are activated RNP2 608, unblocked nucleic acid molecule 661, quencher 610, and fluorophore 611 forming an activated RNP2 with the unblocked nucleic acid/reporter moiety intact 660. Cis-cleavage of the unblocked nucleic acid/reporter moiety 661 results in an activated RNP2 with the reporter moiety activated 662, comprising the activated RNP2 608, the unblocked nucleic acid molecule with the reporter moiety activated 663, quencher 610 and fluorophore 611.

Dual RNP1-1/RNP1-2 Target Capture and Array Formation

Any of the embodiments of the cascade assay described above i.e., using blocked nucleic acid molecules, blocked primer molecules or blocked guide nucleic acids may be employed in conjunction with either of the two ribonucleoprotein (RNP) array-based deconvolution and readout embodiments described below. The first embodiment employs pre-formed RNP1s configured as dual ribonucleoprotein complexes (i.e., dual RNP1-1/RNP1-2s) with two domains, which are arrayed on or otherwise distributed in features on a substrate. This embodiment is particularly useful for detecting nucleic acid targets of interest in small samples or detecting nucleic acid targets of interest that may be at very low concentrations in a sample, as the dual RNP1-1/RNP1-2s are in solution as a "one pot" reaction when the sample is added; that is, it is not necessary to split the sample which may risk forming aliquots of sample lacking some nucleic acid targets of interest. The second embodiment employs RNP1s that are pre-formed and attached to or otherwise distributed into partitions or features forming an array. In this embodiment, the sample (in bulk) is introduced to the array.

Figure 7:
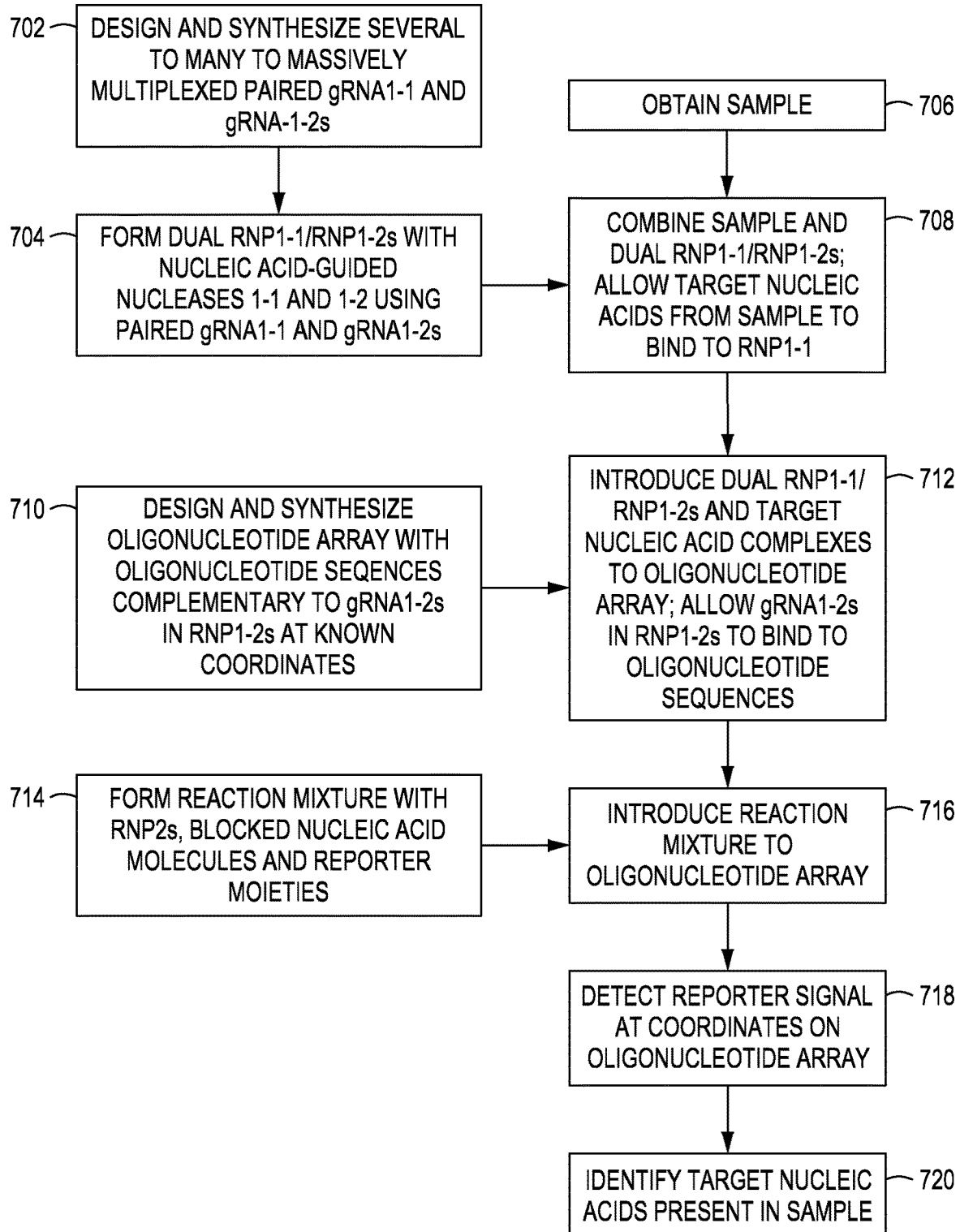
FIG. 7 is a workflow of an exemplary embodiment of the multiplexed cascade assay using an array for deconvolution and readout as described herein.

FIG. 7 is a workflow of one exemplary embodiment of the multiplexed cascade assay employing blocked nucleic acid molecules and using an array-based deconvolution and readout. As explained in further detail below, this embodiment utilizes a first gRNA (gNRA1-1) and a second gRNA (gRNA1-2) that is complexed with a first RNP (RNP1-1) and a second RNP (RNP1-2), respectively, wherein the gRNA1-1 and gRNA1-2 are linked (i.e., paired) together thereby forming a dual RNP1-1/RNP1-2 complex. In this embodiment 700, in a first step, several to many paired gRNA1-1s and gRNA1-2s (i.e., paired gRNA1-1/gRNA1-2s) are designed 702. Paired gRNA1-1/gRNA1-2s are described in detail in relation to FIG. 8A. The paired gRNA1-1/gRNA1-2s are part of the dual RNP1-1/RNP1-2s that comprise two domains where the domains are linked to one another via a non-cleavable linker as described below.

The RNP1-1 domain of the dual RNP1-1/RNP1-2 comprises a gRNA1-1 and a nuclease 1-1, where the gRNA1-1 is complementary to a nucleic acid target of interest or aptamer-complement and nuclease 1-1 is a nucleic acid-guided nuclease comprising trans-cleavage activity. The RNP1-2 domain of the dual RNP1-1/RNP1-2 comprises a gRNA1-2 and a nuclease 1-2, where the gRNA1-2 is complementary to an oligonucleotide at a specific position on an oligonucleotide-based array and nuclease 1-2 is a nucleic acid-guided nuclease that exhibits neither cis- nor trans-cleavage activity but retains the ability to complex with a gRNA, specifically gRNA1-2, in a sequence specific manner. The RNP1-2 domain of the dual RNP1-1/RNP1-2 can hybridize to a complementary nucleic acid sequence; specifically, an oligonucleotide sequence on the oligonucleotide array. In this embodiment and as described below in relation to FIG. 8A, nuclease 1-1 and nuclease 1-2 are not the same nuclease because nuclease 1-1 must retain trans-cleavage activity while nuclease 1-2 must lack both cis- or trans-cleavage activity. However, note that all nuclease 1-1s in a multiplex reaction may be the same nucleic acid-guided nuclease (but do not have to be), and all the nuclease 1-2s in a multiplex reaction may be the same nucleic acid-guided nuclease (but do not have to be).

The paired gRNA1-1/gRNA1-2s are designed such that if the sequence of the gRNA1-1 in a dual RNP1-1/RNP1-2 is known, the sequence of the gRNA1-2 is also known and vice-versa. That is, the RNP-1-1 domain specifies the nucleic acid target of interest to be detected, the RNP1-2 domain specifies the position or coordinate on the oligonucleotide array to which the RNP1-2 will bind, and a signal emanating from a specific position or coordinate on the oligonucleotide array is specific for and thus identifies a nucleic acid target of interest.

Continuing with the embodiment 700 of FIG. 7, once the paired gRNA1-1/gRNA1-2s are designed 702, dual RNP1-1/RNP1-2s are formed 704 with the paired gRNA1-1/gRNA1-2s and nuclease 1-1 and nuclease 1-2. A portion of the sequence of each gRNA is specific to a nuclease; therefore, nuclease 1-1 will form the RNP1-1 domain only with gRNA1-1 and nuclease 1-2 will form the RNP1-2 domain only with gRNA1-2.

In a separate step, a sample is obtained 706. Various types of samples are described above and virtually any sample that comprises or may comprise nucleic acids and/or non-nucleic acids of interest may be used. At step 708, the sample and the dual RNP1-1/RNP1-2s are combined under conditions that favor the targets of interest from the sample binding to the RNP1-1 domains of the dual RNP1-1/RNP1-2s. Also in a separate step, step 710 involves designing and synthesizing an oligonucleotide array comprising oligonucleotide sequences arrayed on or otherwise disposed on or in partitions of the array, where the oligonucleotide sequences on the array are complementary to the gRNA1-2s in the dual RNP1-1/RNP1-2s. Typically, different oligonucleotides of different sequences are positioned in different positions or coordinates on the oligonucleotide array, although there may be redundancies where more than one coordinate may comprise the same oligonucleotide sequence.

At step 712, the dual RNP1-1/RNP1-2s that were combined with the targets in step 708 are combined with the oligonucleotide arrays designed and synthesized in step 710 under conditions that allow for hybridization of the oligonucleotides on the oligonucleotide array to the gRNA1-2s of the RNP1-2 domains of the dual RNP1-1/RNP1-2s.

At step 714, a reaction mixture is formed comprising RNP2s (i.e., the signal boosting ribonucleoprotein complexes), which comprise a gRNA2 and a third nucleic acid-guided nuclease; blocked nucleic acid molecules (or, in alternative embodiments, blocked primer molecules or blocked guide molecules and additional assay components as described in relation to FIGS. 4A, 4B and 5A above); and reporter moieties. At step 716, the reaction mixture is introduced to the oligonucleotide array. The reaction mixture described in FIG. 7 utilizes the cascade assay embodiment that employs blocked nucleic acid molecules as described above in relation to FIG. 3A. As described in detail in the above signal boost cascade assay, a signal produced at a specific coordinate will be generated and thus boosted and detected if and only if a target of interest has bound the gRNA1-1 in the RNP1-1 domain of the dual RNP1-1/RNP1-2s, thereby triggering trans-cleavage activity of nuclease 1-1 in the RNP1-1 domain. Once at least one target of interest is bound to RNP1-1, activated trans-cleavage by the RNP1-1 domain of the dual RNP1-1/RNP1-2 cleaves at least one of the blocked nucleic acid molecules, which in turn binds to (complexes with) gRNA2 activating RNP2. This activation results in additional trans-cleavage activity, which then unblocks more blocked nucleic acid molecules and reporter moieties, resulting in a cascade. The third nucleic acid-guided nucleases can be the same nuclease for all RNP2s (but need not be) and may be the same nuclease as nuclease 1-1s (but need not be) and do possess both cis- and trans-cleavage activity.

At step 718 assuming one or more targets of interest (i.e., nucleic acid targets of interest and/or non-nucleic acid targets of interest) were present in the sample reporter signals are detected at coordinates on the oligonucleotide array, and because the association between gRNA1-1s (nucleic acid targets of interest) and gRNA1-2s (array coordinates or features) are known, the nucleic acid targets of interest present in the sample can be identified 720.

Figure 8A:
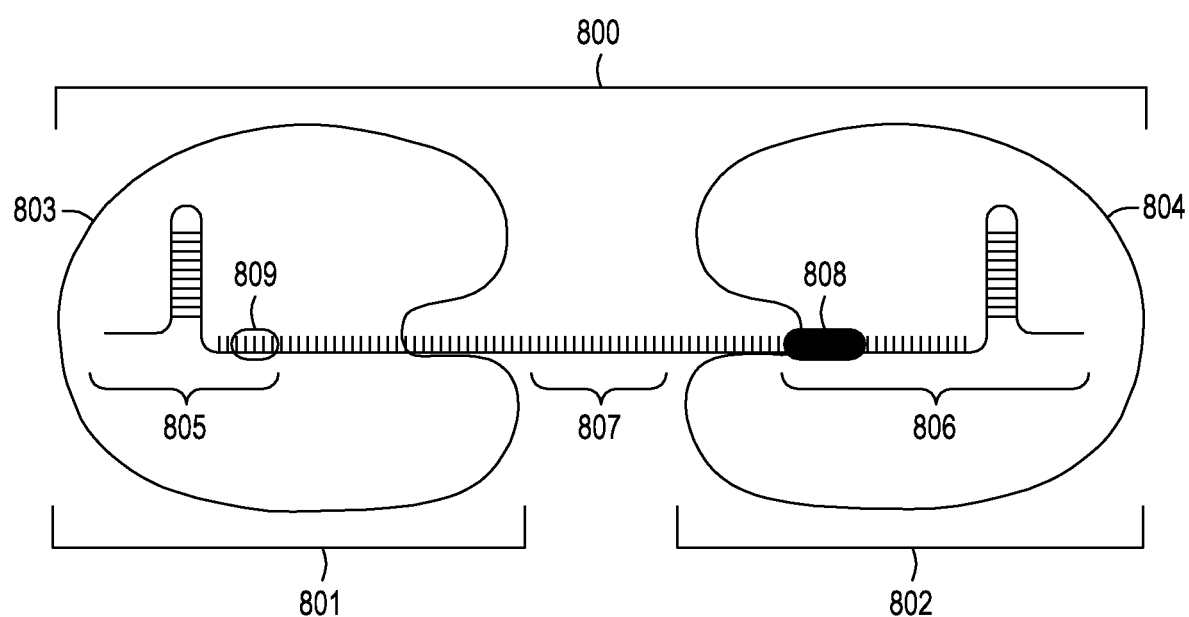
FIG. 8A is a graphic representation of the dual RNP complexes (RNP1-1/RNP1-2s) used in the multiplexed cascade assay workflow embodiment shown in FIG. 7.
Figures 2, 8B:
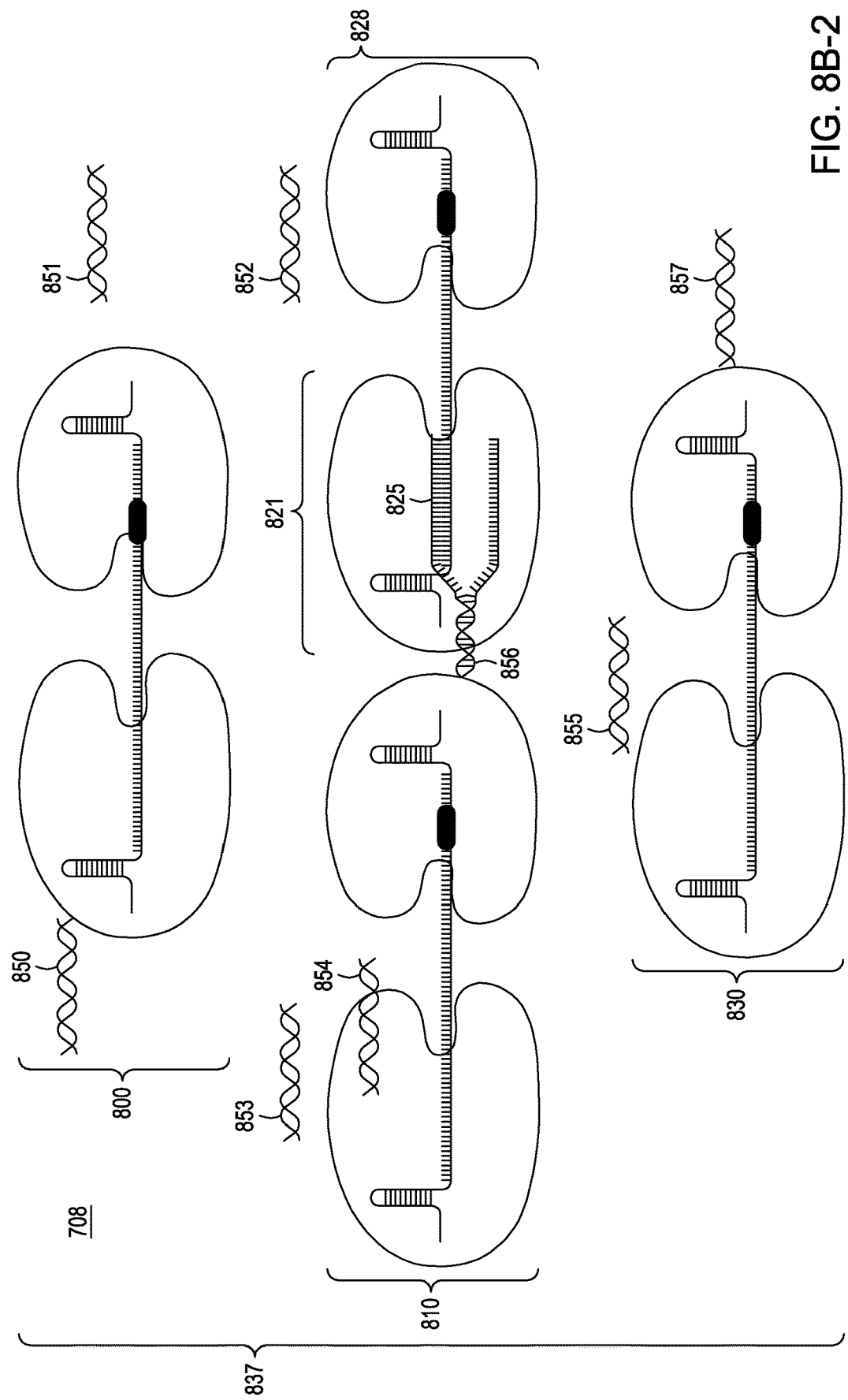

FIG. 8A is a graphic representation of the dual RNP complexes (dual RNP1-1/RNP1-2s) used in the multiplexed cascade assay workflow shown and described in FIGS. 7 and 8B. Dual RNP1-1/RNP1-2 800 comprises a first RNP domain 801 (i.e., RNP1-1, which can be an RNP1-1-NON or RNP1-1-NA to detect non-nucleic acid targets of interest or nucleic acid targets of interest, respectively) and a second RNP domain (i.e., RNP1-2) 802. The RNP1-1 domain comprises nuclease 1-1 803 and gRNA1-1 805; and the RNP1-2 domain comprises nuclease 1-2 804 and gRNA1-2 806. gRNA1-1 and gRNA1-2 are joined together by a non-cleavable linker 807, which connects gRNA1-1 and gRNA1-2 and thus correlates gRNA1-1 and a target of interest (not shown) to gRNA1-2 and an oligonucleotide sequence at a known coordinate on the oligonucleotide array (not shown). gRNA1-1 805 of RNP1-1 801 comprises a sequence in region 809 that is specific to the target of interest (i.e., the target strand of a nucleic acid target of interest or the aptamer-complement (not shown)), and gRNA1-2 806 of RNP1-2 802 comprises a sequence in region 808 that is specific to an x,y position or coordinate on an oligonucleotide array (not shown). As described above, nuclease 1-1 comprises both cis- and trans-cleavage activity, whereas nuclease 1-2 lacks both activities but retains sequence specificity for gRNA1-2s.

Non-cleavable linkers include oligonucleotides with non-cleavable bases such as phosphorothioate modifications, and chemical linkers between gRNA1-1 and gRNA1-2, such as those used in antibody-drug conjugates, which typically fall into two categories: thioethers and maleimidocaproyls.

Figures 3, 8B:
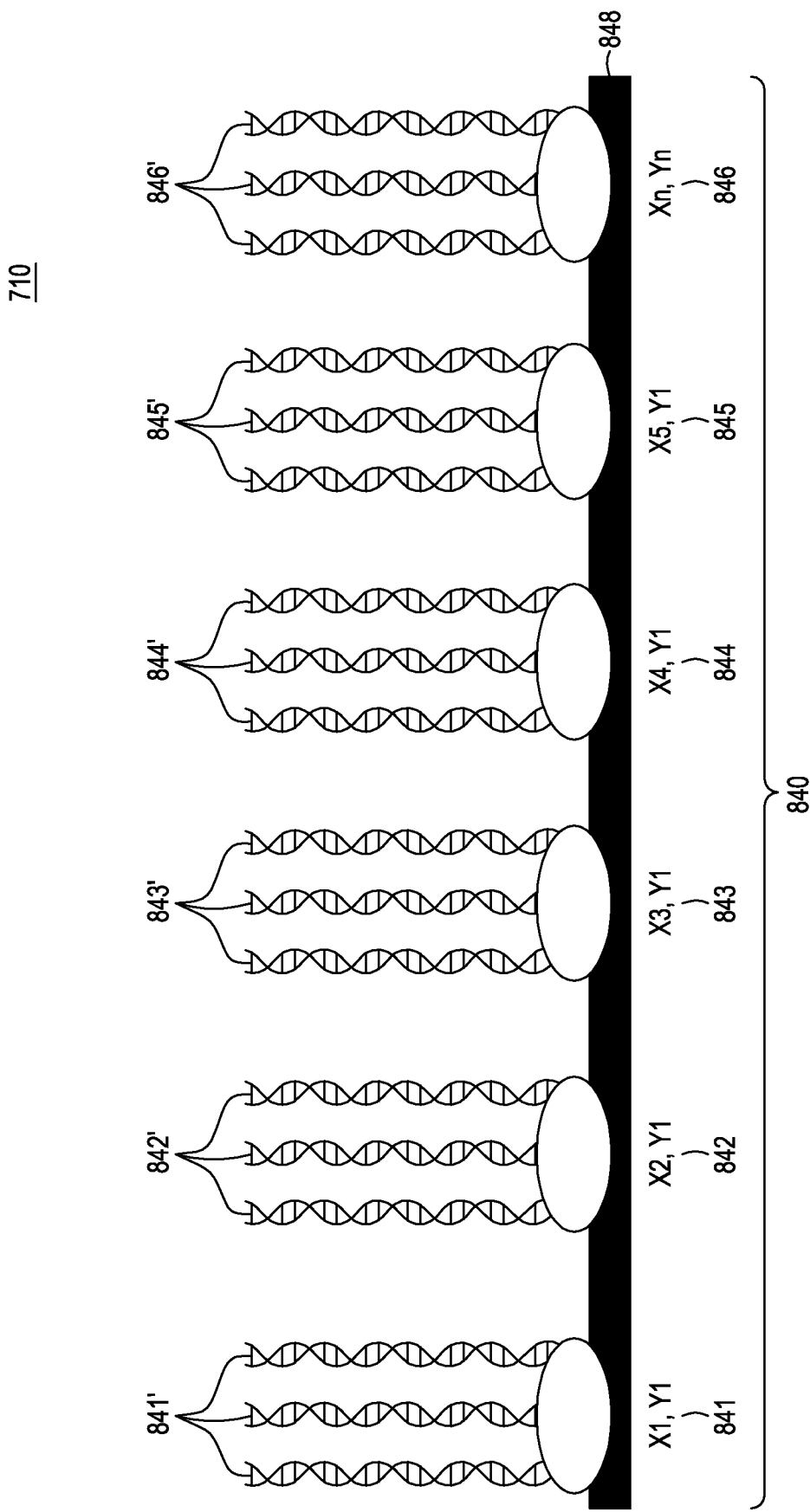
Figures 4, 8B:
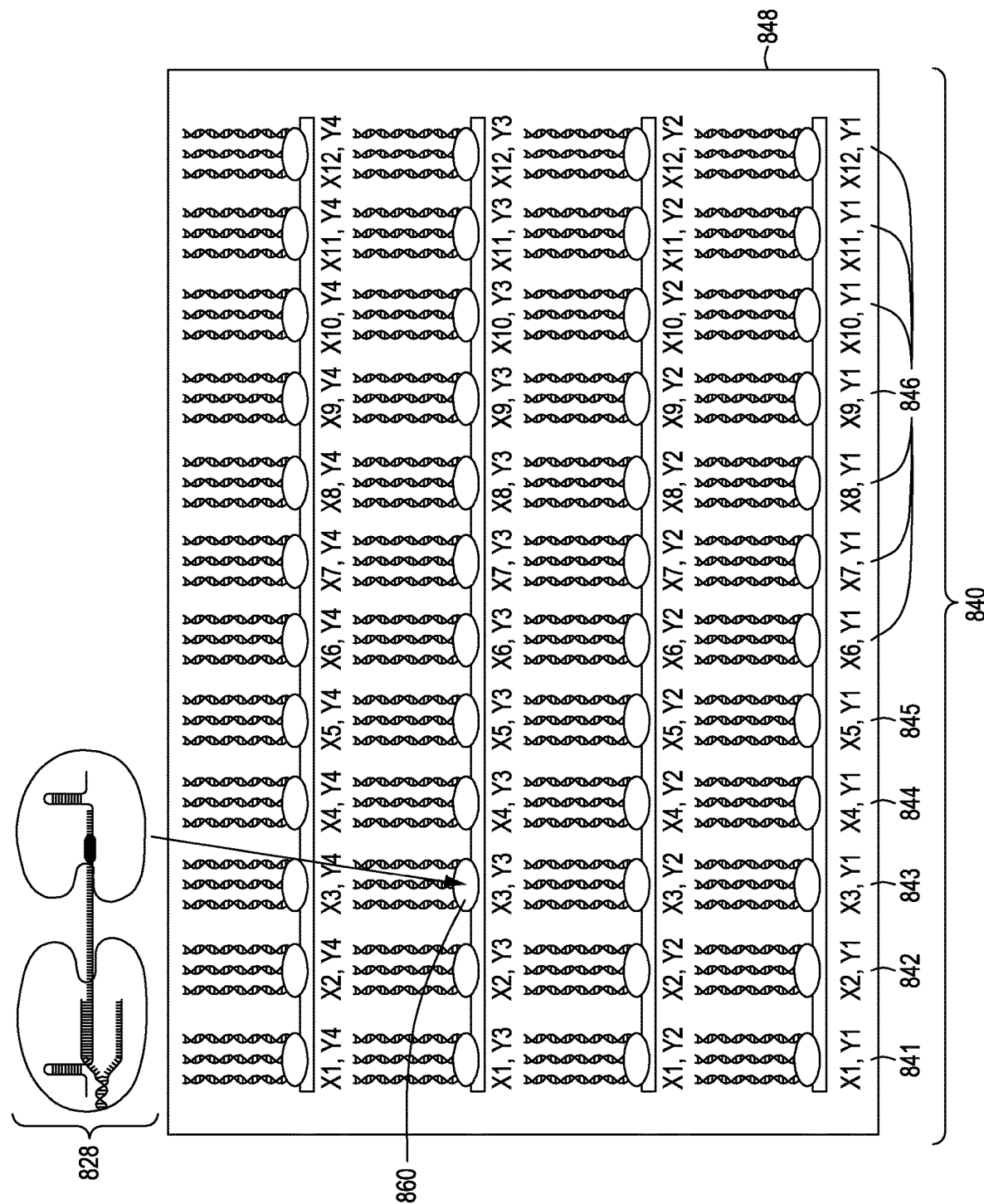

FIGS. 8B-1-8B-4 are graphic representations of the multiplexed cascade assay using an array-based deconvolution and readout as described in relation to FIG. 7. FIG. 8B-1 comprises steps 702+704 from FIG. 7, designing gRNA1-1 and gRNA1-2 pairs and forming RNP1-1/RNP1-2s; FIG. 8B-2 comprises step 708 from FIG. 7, combining the sample and dual RNP1-1/RNP1-2s; FIG. 8B-3 comprises step 710 from FIG. 7, designing and synthesizing an oligonucleotide array with oligonucleotide sequences complementary to the gRNA1-2s at known coordinates; and FIG. 8B-4 comprises step 712 from FIG. 7, introducing the sample and dual RNP1-1/RNP1-2s to the oligonucleotide array.

At step 702+704 from FIG. 7 shown in FIG. 8B-1, a multiplex of four dual RNP1-1/RNP1-2s 800, 810, 820, and 830 are shown. The first dual RNP1-1/RNP1-2 800 comprises an RNP1-1 domain 801 and an RNP1-2 domain 802 (also see FIG. 8A). The RNP1-1 domain comprises nuclease 1-1 803 and gRNA1-1 805; the RNP1-2 domain comprises nuclease 1-2 804 and gRNA1-2 806; and gRNA1-1 805 and gRNA1-2 806 are joined together by a non-cleavable linker 807. The second dual RNP1-1/RNP1-2 810 comprises an RNP1-1 domain 811 and an RNP1-2 domain 812. The RNP1-1 domain 811 comprises nuclease 1-1 813 and gRNA1-1 815; the RNP1-2 812 domain comprises nuclease 1-2 814 and gRNA1-2 816; and gRNA1-1 815 and gRNA1-2 816 are joined together by a non-cleavable linker 807. The third dual RNP1-1/RNP1-2 820 comprises an RNP1-1 domain 821 and an RNP1-2 domain 822. The RNP1-1 domain 821 comprises nuclease 1-1 823 and gRNA1-1 825; the RNP1-2 822 domain comprises nuclease 1-2 824 and gRNA1-2 826; and gRNA1-1 825 and gRNA1-2 826 are joined together by a non-cleavable linker 807. The fourth dual RNP1-1/RNP1-2 830 comprises an RNP1-1 domain 831 and an RNP1-2 domain 832. The RNP1-1 domain 831 comprises nuclease 1-1 833 and gRNA1-1 835; the RNP1-2 832 domain comprises nuclease 1-2 834 and gRNA1-2 836; and gRNA1-1 835 and gRNA1-2 836 are joined together by a non-cleavable linker 807. The first, second, third and fourth RNP1-1 domains can all be RNP1-1-NONs, RNP1-1-NAs or a mixture of RNP1-1-NONs and RNP1-1-NAs.

As described above nuclease 1-1 and nuclease 1-2 of the RNP1-1 and RNP1-2 domains 803 and 804; 813 and 814; 823 and 824; and 833 and 834 cannot be the same nuclease, as the cleavage activity at least the trans-cleavage activity of nuclease 1-1 in the RNP-1-1 domains must be retained whereas the cis- and trans-cleavage activities of the nuclease 1-2 in the RNP2-2 domains must be blocked. Nucleases lacking cleavage activity are often termed "dead" nucleases and are known in the art (see, e.g., Jinek, et al., Science, 337:816-21 (2012)). For example, the Type II cas protein Cas9 comprises two cleavage domains, RuvC and HNH, that cleave target DNA strands (in a cis-cleavage manner) and generate double-stranded breaks in a nucleic acid target. Introducing certain point mutations into each domain blocks the cleavage activity of Cas9 but does not impact the sequence specific binding to the nucleic acid target. Dead variants of Cas12a and Cas13a nucleic acid-guided nucleases can be engineered accordingly by mutating various amino acid residues in the WED, REC1 and/or PAM-interacting (PI) domains of these nucleic acid-guided nucleases.

Also as described above, the paired gRNA1-1 and gRNA1-2s (805 and 806; 815 and 816; 825 and 826; and 835 and 836) are designed such that if the sequence of the gRNA1-1 in a dual RNP1-1/RNP1-2 is known, the sequence of the gRNA1-2 is also known and vice-versa. That is, the RNP-1-1 domain specifies the nucleic acid target of interest to be detected, the RNP1-2 domain specifies the position or coordinate on the oligonucleotide array that the RNP1-2 (and thus the dual RNP1-1/RNP1-2) will bind, and a signal emanating from a specific position or coordinate on the oligonucleotide array thus is specific for a nucleic acid target or non-nucleic acid target of interest.

At step 708 from FIG. 7 shown in FIG. 8B-2, nucleic acids 850, 851, 852, 853, 854, 855, 856, and 857 are combined with dual RNP1-1/RNP1-2s 800, 810, 828, and 830. Note that dual RNP1-1/RNP1-2 820 (not shown here but see steps 702+704 from FIG. 7 in this FIG. 8B) is now dual RNP1-1/RNP1-2 828, as dual RNP1-1/RNP1-2 820 has detected a nucleic acid target of interest 856, which is binding to gRNA1-1 825 of the RNP1-1 821 thereby activating RNP1-1/RNP1-2 828 (820→828).

At step 710 from FIG. 7 shown in FIG. 8B-3, an oligonucleotide array 840 is designed and synthesized. Oligonucleotide array 840 comprises an array substrate 848 upon which oligonucleotides 841', 842', 843', 844', 845', and 846' are disposed on features at coordinates $X_1Y_1$ 841, $X_2Y_1$ 842, $X_3Y_1$ 843, $X_4Y_1$ 844, $X_5Y_1$ 845 up to $X_nY_n$ 846. The oligonucleotides disposed on the array comprise a non-cleavable linker proximal to the array substrate 848 and an oligonucleotide sequence complementary to the sequence of gRNA1-2. The oligonucleotides that are complementary to the RNP1-2s are synthesized.

Oligonucleotide synthesis has been known for over 30 years. The vast majority of oligonucleotides are synthesized on automated synthesizers using phosphoramidite methodology, based on the use of DNA phosphoramidite nucleosides that are modified with a 4,4'-dimethoxytrityl (DMTr) protecting group on the 5'-OH, a β-cyanoethyl-protected 3'-phosphite and appropriate conventional protecting groups on the reactive primary amines in the heterocyclic nucleobase. The phosphoramidite approach is carried out almost exclusively on automated synthesizers using controlled-pore glass or polystyrene solid supports. (For a review, see Caruthers, Biochem. Soc. Trans., 39:575-80 (2011).) The oligo synthesis cycle consists of four steps: deblocking (detritylation); activation/coupling; capping; and oxidation. Synthesis initiates by removal ('deblocking' or 'detritylation') of the 5'-dimethoxytrityl group by treatment with acid (classically 3% trichloroacetic acid in dichloromethane) to make available the reactive 5'-OH group. The phosphoramidite corresponding to the second base in the sequence is activated (using a tetrazole-like product such as 5-(ethylthio)-1-H-tetrazole or 5-(benzylthio)-1-H-tetrazole), then coupled to the first nucleoside via the 5'-OH to form a phosphite linkage. Capping is accomplished using a solution containing acetic anhydride and the catalyst N-methylimidazole. Unless blocked, these truncated oligos can continue to react in subsequent cycles giving near full-length oligos with internal deletions. After oxidation, the cycle is repeated, starting with detritylation of the second molecule and so on.

In the methods herein, instead of column synthesis of relatively large quantities of oligonucleotides, the editing cassette oligos may be synthesized in parallel on a small scale in the wells or partitions of multi-well plates (currently up to 10,000 wells per plate). Solid supports are available in a variety of pore sizes and functionalized nucleoside loadings. Three typical pore sizes are 500 Å, 1000 Å, and 3000 Å. Shorter primer molecules (e.g., approximately 20 bases) can be synthesized on the 500 Å support. Medium-length DNA oligonucleotides (20-80 bases) are best synthesized using the 1000 Å support. Alternatively, 96-well, 384-well and 10,000-well (or more) supports may be used. Currently, each well of a 10,000-well support comprises on the order of several femtomoles ($10^{-15}$ moles) of DNA, resulting in $10^5$-$10^7$ identical sequence-defined molecules per well. It should be apparent to one of ordinary skill in the art given the present disclosure that supports with larger wells or partitions will comprise more identical molecules per well, and that the number of oligonucleotides synthesized per well depends on the particular chemistry and synthesizer.

Finally, at step 712 from FIG. 7 shown in FIG. 8B-4, the combined sample and dual RNP1-1/RNP1-2s (only dual RNP1-1/RNP1-2 828 is shown) are introduced to the oligonucleotide array 840. On the oligonucleotide array 840 is seen substrate 848 and features at coordinates $X_1Y_1$ 841, $X_2Y_1$ 842, $X_3Y_1$ 843, $X_4Y_1$ 844, $X_5Y_1$ 845 up to $X_nY_n$ 846. At coordinate $X_3Y_3$ 860, dual RNP1-1/RNP1-2 828 hybridizes to its complementary oligonucleotide. Other dual RNP1-1/RNP1-2s (800, 810, 830, not shown but see FIG. 8B-1) also hybridize at appropriate coordinates; however, these dual RNP1-1/RNP1-2s 800, 810, 830 will not generate a signal because they did not detect and bind a target of interest (i.e., a target strand of a nucleic acid target of interest or an aptamer-complement). Once the dual RNP1-1/RNP1-

2s with bound targets of interest (if present) are combined with and allowed to hybridize with the oligonucleotide array, a reaction mixture comprising, e.g., RNP2s, blocked nucleic acid molecules (or blocked primer molecules or blocked guide nucleic acids and additional reaction components as described above in relation to FIGS. 4A, 4B and 5A), and reporter moieties are introduced to the oligonucleotide array. A signal is generated at coordinates where a target of interest has bound an RNP1-1 domain thereby triggering trans-cleavage by the RNP1-1 domain of other nucleic acids present in the reaction mixture; here, at coordinate 860 only. That is, only coordinate 860 will have a signal generated that can be detected.

RNP1 Array Formation and Target Capture

Figure 9:
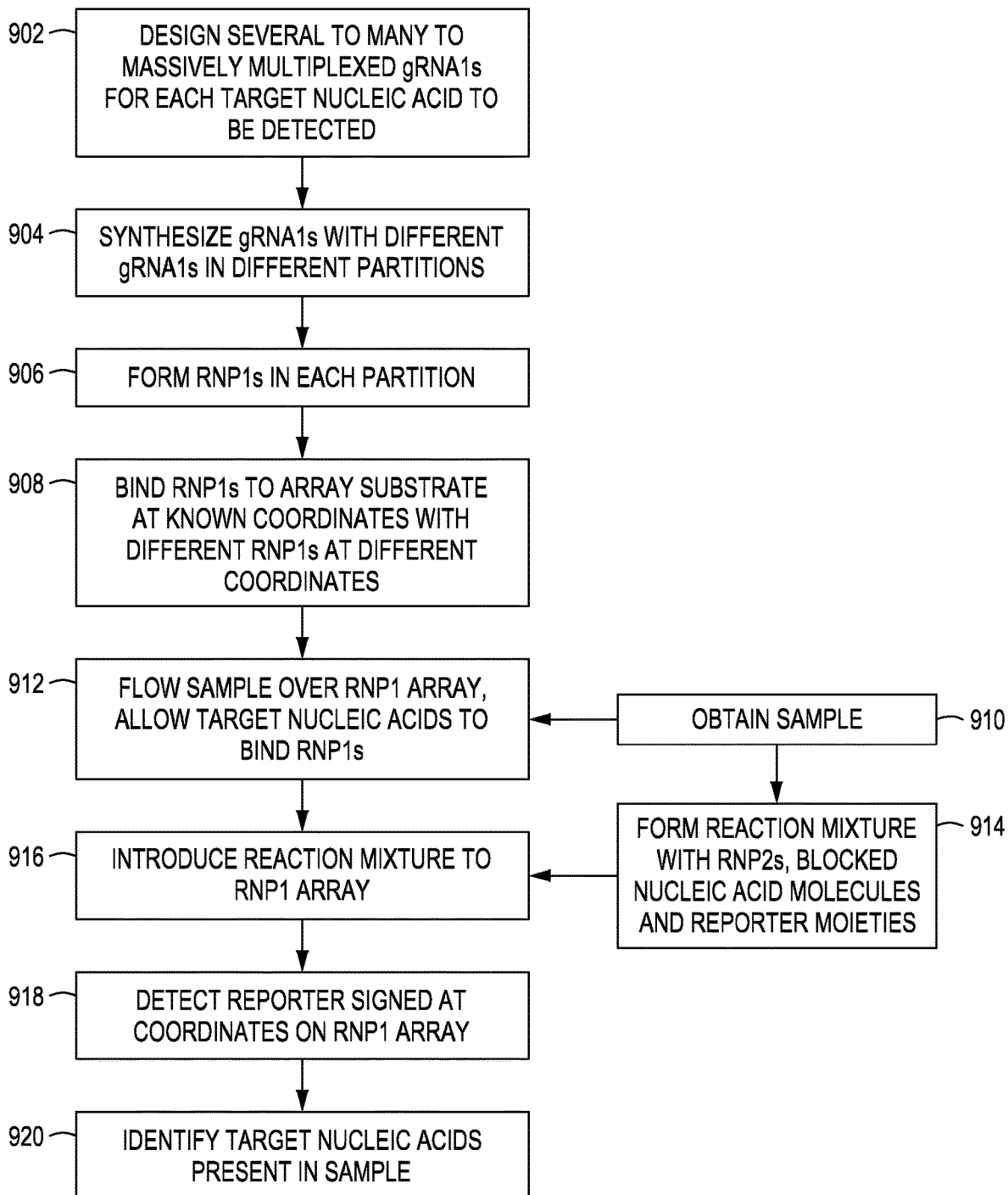
FIG. 9 is a workflow of a second exemplary embodiment of the multiplexed cascade assay using an array for deconvolution and readout as described herein.

FIG. 9 is a workflow of a second exemplary embodiment of the multiplexed signal boost cascade assay using an array-based deconvolution and readout as described herein. In this embodiment 900, in a first step several to many of first gRNAs (i.e., gRNA1s) are designed 902. Like the embodiments of the cascade assays described above and depicted in FIGS. 3A, 4A, 4B and 5A, the gRNA1s are specific for targets of interest (either nucleic acid targets of interest or aptamer-complements of aptamers) and will be combined with a first nucleic acid-guided nuclease to form the first ribonucleoprotein complexes (i.e., RNP1-NONs and RNP1-NAs). Once designed, the gRNA1s (gRNA1-NONs and gRNA1-NAs) are synthesized in separate partitions 904 at known coordinates, and RNP1s (i.e., RNP1-NONs and RNP1-NAs) are then formed in each partition with the first nucleic acid-guided nuclease. The first nucleic acid-guided nuclease in each RNP1 can be the same, or the first nucleic acid-guided nucleases in the RNP1s can be different; however, the first nucleic acid-guided nuclease must possess both cis- and trans-cleavage activity. RNP1s may be formed by, e.g., the protocol described in Example III, infra.

In the next step, the different RNP1s from separate partitions (e.g., well-like partitions) are coupled to a substrate at different, known positions 908 forming an RNP1 array; alternatively, the different RNP1s may be in partitions or features surrounded by interstitial regions and hence the RNP1 array is already formed. There are three general methods used to prepare arrays from presynthesized ribonucleoprotein (RNP) complexes (here, RNP1s, i.e., RNP1-NONs and RNP1-NAs). The simplest way for RNP1s to be coupled to a solid support relies on physical adsorption. RNP1s can be synthesized with an N-terminal or C-terminal peptide of a suitable length with a complementary property to a support to adsorb rapidly to the support. For example, hydrophobic amino acids will adsorb to a hydrophobic material and acidic amino acids will adsorb onto a positively charged surface. This approach is analogous to the immobilization of proteins in ELISA and Western blotting applications that have been used for many years. (See, e.g., Katz, et al., Chem. Soc. Rev., 40:2131-45 (2011).)

Another common strategy available to couple the RNP1s to a substrate is to use selective or nonselective chemical reactions to covalently attach peptides to the support. This approach usually requires chemical modification of the surface of the substrate to introduce the relevant functional groups for attachment, with the benefit being the RNP1s are covalently attached to the substrate and have no risk of dissociating from the surface during an assay. A variety of reactions have been used to immobilize peptides, including those using a nucleophilic α-amino group on the RNP1 to condense with a carboxylate group on the support; using the side chain amino groups on the RNP1 as a functional handle for coupling to polylysine-coated surfaces; using carboxylate groups on RNP1s to react through esterification reactions with the hydroxyl groups presented on cellulose membranes; using amine groups on the RNP1s to react with activated succinimidyl ester or isocyanate groups; or selective reaction of thiols with several electrophilic groups. (See, e.g., Geysen, et al., PNAS USA, 81:3998 (1984); Saxinger, et al., BMC Immunol., 6:1.15647109 (2005); and Schutkowski, et al., Agnew. Chem. Int., 43:2671-74 (2004).)

RNP1s can also be immobilized using biological strategies, either based on ligand-receptor interactions or enzyme-mediated reactions. The specific noncovalent complex between a biotin tag and avidin or streptavidin is a common example for capturing tagged RNP1s onto solid supports. Alternatively, as with the arraying of dual RNP1-1/RNP1-2s, the hybridization of two complementary oligonucleotides can be used to pattern the immobilization of RNP1s, allowing for an array to be "self-assembled." If complementary oligonucleotides are not employed, presynthesized RNP1s comprising oligonucleotide tags are typically patterned onto a functionalized surface using a robotic liquid handling system. The density of peptide spots prepared using this method depends on the minimum dispensing capacity of the robotic liquid handler, the hydrophobicity of the surface, and solvent evaporation (rapid evaporation leads to incomplete immobilization). The RNP1 arrays can also be fabricated using noncontact inkjet printers or laser printing. (See, e.g., Lesaicherre, et al., Med. Chem. Lett, 12:2079-83 (2002).)

Continuing with FIG. 9, in a separate step from synthesizing the RNP1 array, a sample is obtained and prepared 910. A variety of various sample types are described above. The sample is then introduced to the RNP1 array under conditions that allow targets of interest in the sample, if present, to bind to a complementary gRNA1 on the RNP1 array 912 (that is, the target strand of a nucleic acid target of interest or the aptamer-complement of an aptamer). In a separate step, a reaction mixture is formed 914 comprising RNP2s, blocked nucleic acid molecules (or blocked primer molecules or blocked guide molecules and additional reaction mixture components as described above in relation to FIGS. 4A, 4B and 5A) and reporter moieties as described in relation to FIG. 3A (or FIGS. 4A and 4B or FIG. 5A, respectively). At step 916, the reaction mixture is introduced to the RNP1 array comprising the bound nucleic acid targets of interest (if present) under conditions that enable the cascade assay to take place. Once the cascade assay has taken place, reporter signals (if present) are detected at coordinates on the RNP1 array 918 and the nucleic acid targets of interest present in the sample are identified 920 by virtue of the position of the signal on the RNP1 array.

Figure 10:
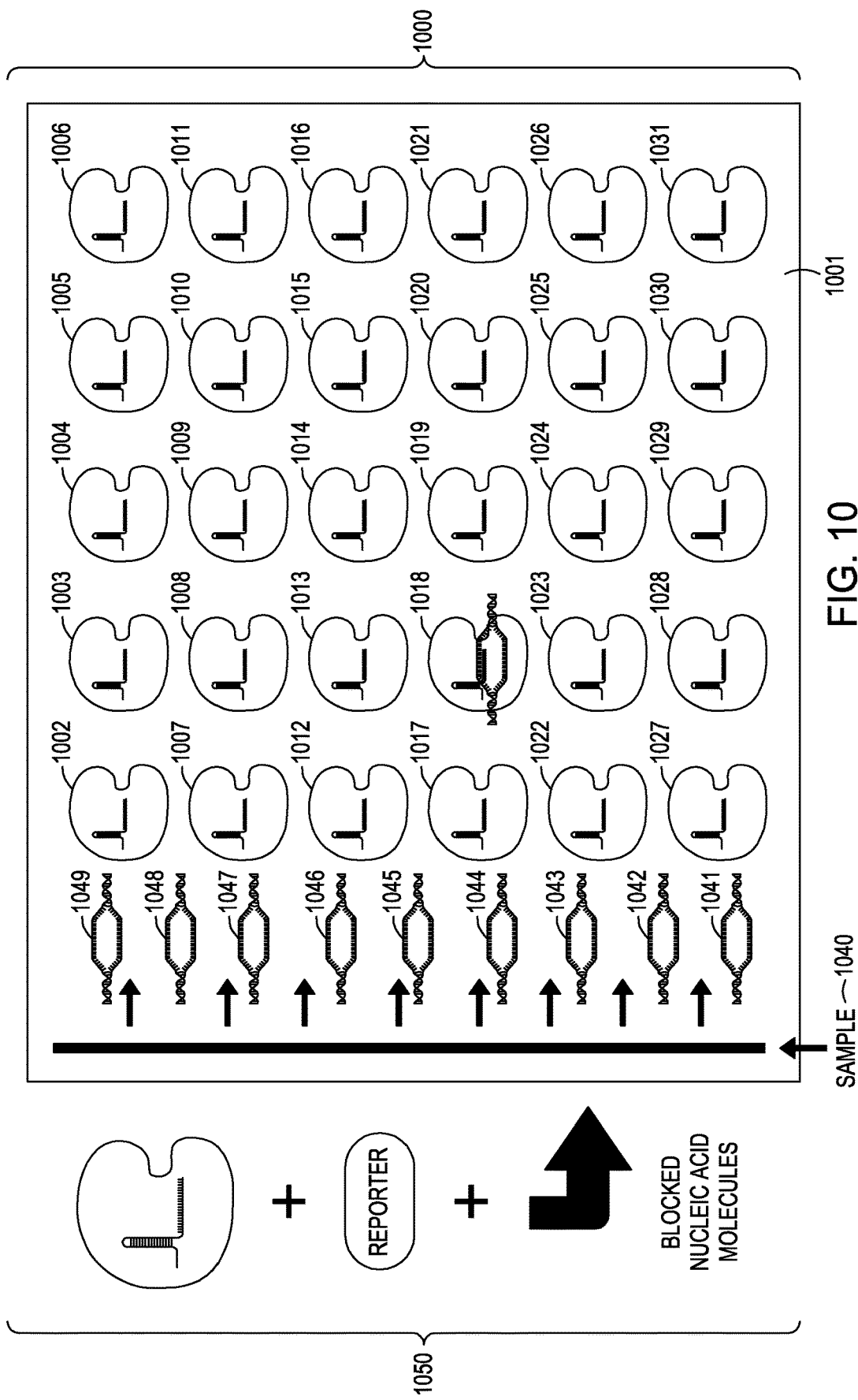
FIG. 10 is a graphic representation of the multiplexed cascade assay using an array for deconvolution and readout as described in FIG. 9.

FIG. 10 is a graphic representation of the multiplexed cascade assay using an RNP-1-array-based deconvolution and readout as described in relation to FIG. 9. Seen in FIG. 10 is an RNP1 array 1000) comprising features 1002-1031 on substrate 1001. Features 1002-1031 may all comprise different RNP1s (typically RNP1s that differ on the basis of the gRNA1 present) or some or all of the RNP1s may be disposed in, e.g., duplicate or triplicate features. That is, features 1002-1031 may all comprise different gRNA1s (i.e., gRNA1-NONs and gRNA1-NAs) or some features (e.g., 1002-1004 and 1022-1024) may comprise the same gRNA1 and other features (e.g., 1005-1021, 1023, and 1025-1031) may comprise different gRNAs from one another and from features 1002-1004 and 1022-1024. There may be several to many to a highly multiplexed number of different gRNA1-NONs and several to many to a multiplexed number of different gRNA1-NAs.

Sample 1040 comprising nucleic acids 1041-1049 is flowed over or otherwise introduced to the RNP1 array under conditions that enable targets of interest, if present, to bind to complementary gRNA1s. Of the nucleic acids 1041-1049 (i.e., nucleic acid targets of interest or aptamer-complements) only one nucleic acid (e.g., 1043) may be a target of interest. Finally, a reaction mixture 1050 comprising RNP2s, blocked nucleic acid molecules (or blocked primer molecules or blocked guide molecules) and reporter molecules is introduced to the RNP1 array under conditions that enable the signal boost cascade assay to take place. Once the cascade assay takes place, reporter signals, if present, are detected and the nucleic acid targets of interest present in the sample are identified, as seen at feature 1018.

Applications of the Cascade Assay

The present disclosure describes cascade assays for detecting one or more nucleic acid targets of interest and/or non-nucleic acid targets of interest in a sample. The cascade assays allow for massive multiplexing and minimum workflow yet provide accurate results at low cost. In embodiments, the cascade assay can detect targets of interest (both nucleic acid targets of interest and non-nucleic acid targets of interest) instantaneously or nearly so, even at ambient temperatures above 20° C. Moreover, the various embodiments of the cascade assay are notable in that, with the exception of the gRNA in RNP1 and the aptamer/aptamer-complement construct, the cascade assay components may stay the same no matter what non-nucleic acid targets of interest are being detected. Also, RNP1 and the aptamer/aptamer-complement construct are easily reprogrammed.

Targets of interest are derived from samples as described in more detail above. Suitable samples for testing include, but are not limited to, any environmental sample, such as air, water, soil, surface, food, clinical sites and products, industrial sites and products, pharmaceuticals, medical devices, nutraceuticals, cosmetics, personal care products, agricultural equipment and sites, and commercial samples, and any biological sample obtained from an organism or a part thereof, such as a plant, animal, or microbe. In some embodiments, the biological sample is obtained from an animal subject, such as a human subject. A biological sample is any solid or fluid sample obtained from, excreted by or secreted by any living organism, including, without limitation, single celled organisms, such as bacteria, yeast, protozoans, and amoebas among others, multicellular organisms including plants or animals, including samples from a healthy or apparently healthy human subject or a human patient affected by a condition or disease to be diagnosed or investigated, such as an infection with a pathogenic microorganism, such as a pathogenic bacteria or virus.

For example, a biological sample can be a biological fluid obtained from a human or non-human (e.g., livestock, pets, wildlife) animal, and may include but is not limited to blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis), or a swab of skin or mucosal membrane surface (e.g., a nasal or buccal swab).

In some embodiments, the sample can be a viral or bacterial sample or a biological sample that has been minimally processed, e.g., only treated with a brief lysis step prior to detection. In other embodiments, minimal processing can include thermal lysis at an elevated temperature. For example, there are many commercial kits available for protein extraction including the BUGBUSTER® line of kits (e.g., for bacteria, yeast, mammalian cells and for nuclear proteins) and the Cellytic Lysis Reagent from Millipore Sigma (St. Louis, MO); the Ready Prep™ protein extraction kit from Biorad (Hercules, CA); protein extraction kits from Abcam (Cambridge UK) and Novus Biologicals (Centennial CO); and total protein extraction kits from Invent Biotech (Plymouth, MA) and emdMillipore (Burlington, MA).

There are many applications of the signal boost cascade assays where one wishes to detect both nucleic acid targets of interest and non-nucleic acids of interest. For example, there are many identified biomarkers for cardiac failure and/or events, including peptides troponin I, troponin T, C-reactive protein, creatine kinase and myglobin; as well as RNAs, including β-myosin heavy chain transcripts and numerous miRNAs (see, e.g., Zhou, et al., Acta Pharmacologica Sinica, 39:1073-84 (2018)). Similarly, there are identified biomarkers for many cancers, including neoepitopes, which arise from post-translational modifications and may be detected by aptamers; as well as hTERT, CA125 (MUC16), VEGF, IL-2, EMP1, human epididymis protein 4, and carcinoembryonic antigen transcripts. In addition—and as mentioned above—the signal boost cascade assays for detecting both nucleic acid targets of interest and non-nucleic acids of interest are useful in biothreat applications, where nucleic acids from, e.g., anthrax, plague, botulism, or hemorrhagic viruses, and metals such as mercury, arsenic and lead can be detected simultaneously in a single assay.

The components of the cascade assay may be provided in various kits for testing at, e.g., point of care facilities, in the field, pandemic testing sites, and the like. In one aspect, the kit for detecting a non-nucleic acid target of interest in a sample includes: first ribonucleoprotein complexes (RNP1s; i.e., RNP1-NONs and RNP1-NAs); aptamer/aptamer-complement double-strand oligonucleotides; second ribonucleoprotein complexes (RNP2s); blocked nucleic acid molecules; and reporter moieties. The first complex (RNP1) comprises a first nucleic acid-guided nuclease and a first gRNA, where the first gRNA includes a sequence complementary to the target strand of a nucleic acid target of interest or to an aptamer-complement. The second complex (RNP2) comprises a second nucleic acid-guided nuclease and a second gRNA that is not complementary to the target strand of a nucleic acid target of interest or to an aptamer-complement. The blocked nucleic acid molecule comprises a sequence complementary to the second gRNA, where trans-cleavage of the blocked nucleic acid molecule results in an unblocked nucleic acid molecule and the unblocked nucleic acid molecule can bind to the second complex (RNP2), thereby activating the trans-cleavage activity of the second nucleic acid-guided nuclease. Activating trans-cleavage activity in RNP2 results in an exponential increase in unblocked nucleic acid molecules and in active reporter moieties, where reporter moieties are nucleic acid molecules and/or are operably linked to the blocked nucleic acid molecules and produce a detectable signal upon cleavage by RNP2.

In a second aspect, the kit for detecting non-nucleic acid targets of interest in sample includes: first ribonucleoprotein complexes (RNP1s; i.e., RNP1-NONs and RNP1-NAs); second ribonucleoprotein complexes (RNP2s); template molecules; blocked primer molecules; aptamer/aptamer-complement double-strand oligonucleotides; a polymerase, nucleotide triphosphates (NTPs), and reporter moieties. The first ribonucleoprotein complex (RNP1) comprises a first nucleic acid-guided nuclease and a first gRNA, where the first gRNA includes a sequence complementary to the target strand of a nucleic acid target of interest or to the aptamer-complement of an aptamer/aptamer-complement double strand oligonucleotides and where binding of RNP1 to the target strand of a nucleic acid target of interest or to the aptamer-complement activates trans-cleavage activity of the first nucleic acid-guided nuclease. The second complex (RNP2) comprises a second nucleic acid-guided nuclease and a second gRNA that is not complementary to the aptamer-complement. The template molecules comprise a primer binding domain (PBD) sequence as well as a sequence corresponding to a spacer sequence of the second gRNA. The blocked primer molecules comprise a sequence that is complementary to the PBD on the template nucleic acid molecule and a blocking moiety.

Upon binding to the target strand of a nucleic acid target of interest or to the aptamer-complement, RNP1 becomes active triggering trans-cleavage activity that cuts at least one of the blocked primer molecules to produce at least one unblocked primer molecule. The unblocked primer molecule hybridizes to the PBD of one of the template nucleic acid molecules, is trimmed of excess nucleotides by the 3'-to-5' exonuclease activity of the polymerase and is then extended by the polymerase and NTPs to form a synthesized activating nucleic acid with a sequence that is complementary to the second gRNA of RNP2. Upon activating RNP2, additional trans-cleavage activity is initiated, cleaving at least one additional blocked primer molecule. Continued cleavage of blocked primer molecules and subsequent activation of more RNP2s proceeds at an exponential rate. A signal is generated upon cleavage of a reporter molecule by active RNP2 complexes; therefore, a change in signal production indicates the presence of the nucleic acid target of interest.

In a third aspect, the kit for detecting a nucleic acid target molecule in sample includes: first ribonucleoprotein complexes (RNP1s; i.e, RNP1-NONs and/or RNP1-NAs) comprising first gRNAs and first nucleic acid-guided nucleases; second nucleic acid-guided nucleases; blocked guide nucleic acids; RNP2 activating nucleic acids; aptamer/aptamer-complement double-strand oligonucleotides; and reporter moieties. The first ribonucleoprotein complex (RNP1) comprises a first nucleic acid-guided nuclease and a first gRNA, where the first gRNA includes a sequence complementary to the target strand of a nucleic acid target of interest or to the aptamer-complement.

The trans-cleavage activity of RNP1 triggered by binding of the target strand of a nucleic acid target of interest or to the aptamer-complement cuts at least one of the blocked guide nucleic acids to produce at least one unblocked guide nucleic acid. The unblocked guide nucleic acid has complementarity with the RNP2 activating nucleic acids in the reaction mixture and combines with the second nucleic acid-guided nuclease to form RNP2. Once RNP2 is formed with the second nucleic acid-guided nuclease and the unblocked guide nucleic acids the RNP2 activating nucleic acids activate cis-cleavage of RNP2, as well as trans-cleavage activity. Upon activating RNP2, additional trans-cleavage activity is initiated, cleaving at least one additional blocked guide nucleic acid. Continued cleavage of blocked guide nucleic acids and subsequent activation of more RNP2s proceeds at an exponential rate. A signal is generated upon cleavage of a reporter molecule by active RNP2 complexes; therefore, a change in signal production indicates the presence of the target molecule of interest.

Any of the kits described herein may further include a sample collection device, e.g., a syringe, lancet, nasal swab, or buccal swab for collecting a biological sample from a subject, and/or a sample preparation reagent, e.g., a lysis reagent. Each component of the kit may be in separate container or two or more components may be in the same container. The kit may further include a lateral flow device used for contacting the biological sample with the reaction mixture, where a signal is generated to indicate the presence or absence of the target molecule of interest. In addition, the kit may further include instructions for use and other information.

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Preparation of Nucleic Acids of Interest

Mechanical lysis: Nucleic acids of interest may be isolated by various methods depending on the cell type and source (e.g., tissue, blood, saliva, environmental sample, etc.). Mechanical lysis is a widely used cell lysis method and may be used to extract nucleic acids from bacterial, yeast, plant and mammalian cells. Cells are disrupted by agitating a cell suspension with "beads" at high speeds (beads for disrupting various types of cells can be sourced from, e.g., OPS Diagnostics (Lebanon NJ, US) and MP Biomedicals (Irvine, CA, USA)). Mechanical lysis via beads begins with harvesting cells in a tissue or liquid, where the cells are first centrifuged and pelleted. The supernatant is removed and replaced with a buffer containing detergents as well as lysozyme and protease. The cell suspension is mixed to promote breakdown of the proteins in the cells and the cell suspension then is combined with small beads (e.g., glass, steel, or ceramic beads) that are mixed (e.g., vortexed) with the cell suspension at high speeds. The beads collide with the cells, breaking open the cell membrane with shear forces. After "bead beating", the cell suspension is centrifuged to pellet the cellular debris and beads, and the supernatant may be purified via a nucleic acid binding column (such as the MagMAX™ Viral/Pathogen Nucleic Acid Isolation Kit from ThermoFisher (Waltham, MA, USA) and others from Qiagen (Hilden, Germany), TakaraBio (San Jose, CA, USA), and Biocomma (Shenzen, China)) to collect the nucleic acids (see the discussion of solid phase extraction below).

Solid phase extraction (SPE): Another method for capturing nucleic acids is through solid phase extraction. SPE involves a liquid and stationary phase, which selectively separates the target analyte (here, nucleic acids) from the liquid in which the cells are suspended based on specific hydrophobic, polar, and/or ionic properties of the target analyte in the liquid and the stationary solid matrix. Silica binding columns and their derivatives are the most commonly used SPE techniques, having a high binding affinity for DNA under alkaline conditions and increased salt concentration; thus, a highly alkaline and concentrated salt buffer is used. The nucleic acid sample is centrifuged through a column with a highly porous and high surface area silica matrix, where binding occurs via the affinity between negatively charged nucleic acids and positively charged silica material. The nucleic acids bind to the silica matrices, while the other cell components and chemicals pass through the matrix without binding. One or more wash steps typically are performed after the initial sample binding (i.e., the nucleic acids to the matrix), to further purify the bound nucleic acids, removing excess chemicals and cellular components non-specifically bound to the silica matrix. Alternative versions of SPE include reverse SPE and ion exchange SPE, and use of glass particles, cellulose matrices, and magnetic beads.

Thermal lysis: Thermal lysis involves heating a sample of mammalian cells, virions, or bacterial cells at high temperatures thereby damaging the cellular membranes by denaturizing the membrane proteins. Denaturizing the membrane proteins results in the release of intracellular DNA. Cells are generally heated above 90° C., however time and temperature may vary depending on sample volume and sample type. Once lysed, typically one or more downstream methods, such as use of nucleic acid binding columns for solid phase extraction as described above, are required to further purify the nucleic acids.

Physical lysis: Common physical lysis methods include sonication and osmotic shock. Sonication involves creating and rupturing of cavities or bubbles to release shockwaves, thereby disintegrating the cellular membranes of the cells. In the sonication process, cells are added into lysis buffer, often containing phenylmethylsulfonyl fluoride, to inhibit proteases. The cell samples are then placed in a water bath and a sonication wand is placed directly into the sample solution. Sonication typically occurs between 20-50 kHz, causing cavities to be formed throughout the solution as a result of the ultrasonic vibrations; subsequent reduction of pressure then causes the collapse of the cavity or bubble resulting in a large amount of mechanical energy being released in the form of a shockwave that propagates through the solution and disintegrates the cellular membrane. The duration of the sonication pulses and number of pulses performed varies depending on cell type and the downstream application. After sonication, the cell suspension typically is centrifuged to pellet the cellular debris and the supernatant containing the nucleic acids may be further purified by solid phase extraction as described above.

Another form of physical lysis is osmotic shock, which is most typically used with mammalian cells. Osmotic shock involves placing cells in DI/distilled water with no salt added. Because the salt concentration is lower in the solution than in the cells, water is forced into the cell causing the cell to burst, thereby rupturing the cellular membrane. The sample is typically purified and extracted by techniques such as e.g., solid phase extraction or other techniques known to those of skill in the art.

Chemical lysis: Chemical lysis involves rupturing cellular and nuclear membranes by disrupting the hydrophobic-hydrophilic interactions in the membrane bilayers via detergents. Salts and buffers (such as, e.g., Tris-HCl pH8) are used to stabilize pH during extraction, and chelating agents (such as ethylenediaminetetraacetic acid (EDTA)) and inhibitors (e.g., Proteinase K) are also added to preserve the integrity of the nucleic acids and protect against degradation. Often, chemical lysis is used with enzymatic disruption methods (see below) for lysing bacterial cell walls. In addition, detergents are used to lyse and break down cellular membranes by solubilizing the lipids and membrane proteins on the surface of cells. The contents of the cells include, in addition to the desired nucleic acids, inner cellular proteins and cellular debris. Enzymes and other inhibitors are added after lysis to inactivate nucleases that may degrade the nucleic acids. Proteinase K is commonly added after lysis, destroying DNase and RNase enzymes capable of degrading the nucleic acids. After treatment with enzymes, the sample is centrifuged, pelleting cellular debris, while the nucleic acids remain in the solution. The nucleic acids may be further purified as described above.

Another form of chemical lysis is the widely used procedure of phenol-chloroform extraction. Phenol-chloroform extraction involves the ability for nucleic acids to remain soluble in an aqueous solution in an acidic environment, while the proteins and cellular debris can be pelleted down via centrifugation. Phenol and chloroform ensure a clear separation of the aqueous and organic (debris) phases. For DNA, a pH of 7-8 is used, and for RNA, a more acidic pH of 4.5 is used.

Enzymatic lysis: Enzymatic disruption methods are commonly combined with other lysis methods such as those described above to disrupt cellular walls (bacteria and plants) and membranes. Enzymes such as lysozyme, lysostaphin, zymolase, and protease are often used in combination with other techniques such as physical and chemical lysis. For example, one can use cellulase to disrupt plant cell walls, lysosomes to disrupt bacterial cell walls and zymolase to disrupt yeast cell walls.

Example II: Preparation of Non-Nucleic Acid Targets of Interest

In this example, the reagents and instruments are pre-chilled to reduce protein degradation. 10 µL sodium orthovanadate solution and 10 µL protease inhibitor cocktail solution are added per 1 mL of RIPA lysis buffer before use to prevent proteolysis and maintain phosphorylation of proteins. Phosphobuffered saline (PBS) is prepared by dissolving 8 g NaCl, 0.2 g KCl, 1.15 g $Na_2HPO_4$ and 0.2 g $KH_2PO_4$ in 800 mL distilled water and adjusting the PH to 7.4 with HCl and bringing the final volume of the solution to 1 liter with additional distilled $H_2O$. RIPA lysis buffer is prepared by combining 50 mM Tris-ICl (pH 7.4), 150 mM NaCl, 1 mM EDTA, 1% NP-40, 1% Na-deoxycholate, 0.1% SDS, sterile-filtered.

Total Protein Extraction from Cell Suspension: Cells are collected by centrifuging the cell suspension at 500×g for 5 minutes and aspirating the culture media carefully. The cells are washed with ice-cold PBS then centrifuged at 500×g for 5 minutes at 4° C. with the supernatant aspirated. The wash step is repeated twice. 1 mL ice-cold RIPA lysis buffer is added for $1\times10^7$ cells and the contents were transferred to a microcentrifuge tube and agitated for 20 min at 4° C. The cells are then centrifuged at 13,000×g for 20 min at 4° C. and the supernatant containing the soluble protein is collected in a new tube kept on ice.

Total Protein Extraction from Adherent Cells: The culture media is aspirated from adherent cells slowly using suction and a pipette. The adherent cells are washed carefully with ice-cold PBS, rocked gently and the PBS is aspirated to remove residual medium. This wash step is repeated twice. 1 nL ice-cold RIPA lysis buffer is added for $1\times10^7$ cells and the plate is scraped using a cold plastic cell scraper to lyse residual cells. The cells are then gently transferred to a 1.5 mL microcentrifuge tube and allowed to stand for 20 min at 4° C. with gentle agitation. The cells are then centrifuged at 13,000×g for 20 min at 4° C. and the supernatant containing the soluble protein is transferred into a new tube and kept on ice.

Total Protein Extraction from Tissue: The tissue is cut into pieces on ice and transferred to a microcentrifuge tube and snap-frozen by immersing the tube in liquid nitrogen. 300 µL ice-cold RIPA lysis buffer is added for 5 mg tissue and the tissue is then homogenized with an electric homogenizer (e.g., sonicator) on ice. The sonication probe is washed twice with an additional 400 µL ice-cold RIPA lysis buffer and the contents agitated for 2 h at 4° C. The sample is then centrifuged at 13,000×g for 20 minutes at 4° C. and the supernatant containing the soluble protein is collected and transferred to a new tube kept on ice.

Example III: RNP Formation

For RNP complex formation, 250 nM of LbCas12a nuclease protein was incubated with 375 nM of a target specific gRNA in 1× Buffer (10 mM Tris-HCl, 100 g/mL BSA) with 2-15 mM $MgCl_2$ at 25° C. for 20 minutes. The total reaction volume was 2 L. Other ratios of LbCas12a nuclease to gRNAs were tested, including 1:1, 1:2 and 1:5. The incubation temperature can range from 20° C.-37° C., and the incubation time can range from 10 minutes to 4 hours.

Example IV: Blocked Nucleic Acid, Blocked Primer and Blocked Guide Formation Ramp cooling: For formation of the secondary structure of blocked nucleic acids, 2.5 M of a blocked nucleic acid molecule (any of Formulas I-IV) was mixed in a T50 buffer (20 mM Tris HCl, 50 mM NaCl) with 10 mM $MgCl_2$ for a total volume of 50 L. The reaction was heated to 95° C. at 1.6° C./second and incubated at 95° C. for 5 minutes to dehybridize any secondary structures. Thereafter, the reaction was cooled to 37° C. at 0.015° C./second to form the desired secondary structure.

Snap cooling: For formation of the secondary structure of blocked nucleic acids, 2.5 M of a blocked nucleic acid molecule (any of Formulas I-IV) was mixed in a T50 buffer (20 mM Tris HCl, 50 mM NaCl) with 10 mM $MgCl_2$ for a total volume of 50 L. The reaction was heated to 95° C. at 1.6° C./second and incubated at 95° C. for 5 minutes to dehybridize any secondary structures. Thereafter, the reaction was cooled to room temperature by removing the heat source to form the desired secondary structure.

Snap cooling on ice: For formation of the secondary structure of blocked nucleic acids, 2.5 M of a blocked nucleic acid molecule (any of Formulas I-IV) was mixed in a T50 buffer (20 mM Tris HCl, 50 mM NaCl) with 10 mM $MgCl_2$ for a total volume of 50 µL. The reaction was heated to 95° C. at 1.6° C./second and incubated at 95° C. for 5 minutes to dehybridize any secondary structures. Thereafter, the reaction was cooled to room temperature by placing the reaction tube on ice to form the desired secondary structure.

Example V: Reporter Moiety Formation

The reporter moieties used in the reactions herein were single-stranded DNA oligonucleotides 5-10 bases in length (e.g., with sequences of TTATT, TTTATTT, ATTAT, ATTTATTTA, AAAAA, or AAAAAAAAA) with a fluorophore and a quencher attached on the 5' and 3' ends, respectively. In one example using a Cas12a cascade, the fluorophore was FAM-6, and the quencher was IOWA BLACK® (Integrated DNA Technologies, Coralville, IA). In another example using a Cas13 cascade, the reporter moieties were single stranded RNA oligonucleotides 5-10 bases in length (e.g., r(U)n, r(UUAUU)n, r(A)n).

Example VI: Cascade Assay

First Format (final reaction mixture components added at the same time): RNP1 is assembled using the LbCas12a nuclease and a gRNA for the aptamer-complement to an aptamer specific for a Methicillin resistant *Staphylococcus aureus* (MRSA) protein according to the RNP complex formation protocol described in Example III. Briefly, 250 nM LbCas12a nuclease is assembled with 375 nM of the aptamer-complement gRNA. Next, RNP2 is formed using the LbCas12a nuclease and a gRNA specific for a selected blocked nucleic acid molecule using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. Thereafter, the final reaction is carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, 15 nM LbCas12a: 22.5 nM gRNA RNP1, 20 nM LbCas12a: 35 nM gRNA RNP2, 50 mM aptamer/aptamer-complement and 50 nM blocked nucleic acid molecule (any one of Formula I-IV) in a total volume of 9 µL, 1 µL of MRSA protein target is added to make a final volume of 10 µL. The final reaction is incubated in a thermocycler at 25° C. with fluorescence measurements taken every 1 minute.

Second Format (RNP1 and MRSA target pre-incubated before addition to final reaction mixture): RNP1 is assembled using the LbCas12a nuclease and a gRNA for the aptamer-complement to an aptamer specific for a Methicillin resistant *Staphylococcus aureus* (MRSA) protein according to the RNP complex formation protocol described in Example III. Briefly, 250 nM LbCas12a nuclease is assembled with 375 nM of the aptamer-complement gRNA. Next, RNP2 is formed using the LbCas12a nuclease and a gRNA specific for a selected blocked nucleic acid molecule (Formula I-IV) using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s are diluted to a concentration of 75 nM LbCas12a: 112.5 nM gRNA. After dilution, the formed RNP1 is mixed with 1 µL of MRSA DNA target and incubated at 20° C.-37° C. for up to 10 minutes to activate RNP1. The final reaction is carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, the pre-incubated and activated RNP1, 20 nM LbCas12a: 35 nM gRNA RNP2, 50 nM aptamer/aptamer-complement and 50 nM blocked nucleic acid molecule (any one of Formula I-IV) in a total volume of 9 L. The final reaction is incubated in a thermocycler at 25° C. with fluorescence measurements taken every 1 minute.

Third Format (RNP1 and MRSA target pre-incubated before addition to final reaction mixture and blocked nucleic acid molecule added to final reaction mixture last): RNP1 is assembled using the LbCas12a nuclease and a gRNA for the aptamer-complement to an aptamer specific for a Methicillin resistant *Staphylococcus aureus* (MRSA) protein according to the RNP complex formation protocol described in Example III. Briefly, 250 nM LbCas12a nuclease is assembled with 375 nM of the aptamer-complement specific gRNA. Next, RNP2 is formed using the LbCas12a nuclease and a gRNA specific for a selected blocked nucleic acid molecule (Formula I-IV) using 500 nM LbCas12a nuclease assembled with 750 nM of the blocked nucleic acid-specific gRNA incubated in 1×NEB 2.1 Buffer (New England Biolabs, Ipswich, MA) with 5 mM MgCl$_2$ at 25° C. for 20-40 minutes. Following incubation, RNP1s are diluted to a concentration of 75 nM LbCas12a: 112.5 nM gRNA. After dilution, the formed RNP1 is mixed with 1 µL of aptamer/aptamer-complement and incubated at 20° C.-37° C. for up to 10 minutes to activate RNP1. The final reaction is carried out in 1× Buffer, with 500 nM of the ssDNA reporter moiety, 1×ROX dye (Thermo Fisher Scientific, Waltham, MA) for passive reference, 2.5 mM MgCl$_2$, 4 mM NaCl, the pre-incubated and activated RNP1, and 20 nM LbCas12a: 35 nM gRNA RNP2 in a total volume of 9 µL. Once the reaction mixture is made, 1 µL (50 nM) blocked nucleic acid molecule (any one of Formula I-IV) is added for a total volume of 10 µL. The final reaction is incubated in a thermocycler at 25° C. with fluorescence measurements taken every 1 minute.

While certain embodiments have been described, these embodiments have been presented by way of example only and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

We claim:

1. A method for detecting one or more non-nucleic acid targets of interest in a sample comprising the steps of:
providing a reaction mix comprising:
aptamer/masked molecule compound molecules, comprising an aptamer region and a masked molecule region, wherein the masked molecule region comprises a target strand and a non-target strand;
first ribonucleoprotein complexes (RNP1-NONs), wherein each of the RNP1-NONs comprises a first nucleic acid-guided nuclease and a first gRNA (gRNA1-NON); wherein the gRNA1-NONs comprise a sequence complementary to the target strand of the masked molecule region of the aptamer/masked molecule compound molecules, and wherein the first nucleic acid-guided nuclease exhibits trans-cleavage activity;
second ribonucleoprotein complexes (RNP2s), wherein each of the RNP2s comprises a second nucleic acid-guided nuclease and a second gRNA that is not complementary to the aptamer complement, and wherein the second nucleic acid-guided nuclease exhibits trans-cleavage activity;
a plurality of blocked nucleic acid molecules each comprising a sequence complementary to the second gRNA; and
a plurality of reporter moieties;
contacting the reaction mix with the sample under conditions that allow non-nucleic acid targets of interest in the sample to bind to the aptamer region of the aptamer/masked molecule compound molecules, wherein:
upon binding of the aptamer region of the aptamer/masked molecule compound molecules to the non-nucleic acid targets of interest, the aptamer/masked molecule compound molecules are reconfigured, unmasking the masked molecule region of the aptamer/masked molecule compound molecules and freeing the target strand to bind with the RNP1-NONs;
upon binding of the target strand to the RNP1-NON, the RNP1-NON becomes active trans-cleaving at least one of the blocked nucleic acid molecules, thereby producing at least one unblocked nucleic acid molecule that can complex with RNP2; and
upon binding of the at least one unblocked nucleic acid molecule to one of the RNP2s, the unblocked nucleic acid molecule-bound RNP2 becomes active trans-cleaves at least one more of the blocked nucleic acid molecules and at least one reporter moiety in a cascade;
allowing the cascade to continue; and
detecting the unblocked nucleic acid molecules, thereby detecting the target nucleic acid of interest in the sample.

2. The method of claim 1, wherein the reporter moieties produce a detectable signal upon trans-cleavage activity by the RNP1-NON and/or RNP2 to identify the presence of one or more non-nucleic acid targets of interest in the sample.

3. The method of claim 2, wherein the detectable signal is a fluorescent signal.

4. The method of claim 2, wherein the detectable signal is a phosphorescent signal.

5. The method of claim 1, wherein the aptamer is a riboswitch and wherein the riboswitch comprises an aptamer domain to an effector molecule of choice and an expression platform domain heterologous to the aptamer domain.

6. The method of claim 5, wherein the expression platform domain is selected from an expression platform from a cobalamin riboswitch, a cyclic AMP-GMP riboswitch, a cyclic di-AMP riboswitch, a cylic di-GMP riboswitch, a fluoride riboswitch, a Flavin mononucleotide (FMN) riboswitch, a glmS (glucose-6-pohosphate) riboswitch, a Glutamine riboswitch, a Glycine riboswitch, a Lysine riboswitch, a manganese riboswitch, a NiCo riboswitch, a PreQ1 (prequeuosine 1) riboswitch, a purine riboswitch, an SAH (S-adenosylhomocysteine) riboswitch, an SAM (S-adenosyl methionine) riboswitch, an SAM-SAH (recognizes both S-adenosylhomocysteine and S-adenosyl methionine) riboswitch, a tetrahdrofolate riboswitch, a TPP (thiamin biosynthesis- and found in eukaryotes) riboswitch, and a SMP.STP riboswitch.

7. The method of claim 1, wherein the one or both of RNP1-NON and RNP2 comprises a nucleic acid-guided nuclease selected from Cas3, Cas12a, Cas12b, Cas12c, Cas12d, Cas12e, Cas14, Cas12h, Cas12i, Cas12j, Cas13a, or Cas13b.

8. The method of claim 1, wherein the one or both of RNP1-NON and RNP2 comprises a nucleic acid-guided nuclease that is a Type V nucleic acid-guided nuclease or a Type VI nucleic acid-guided nuclease.

9. The method of claim 1, wherein the blocked nucleic acid molecule comprises a structure represented by any one of Formulas I-IV, wherein Formulas I-IV are in the 5'-to-3' direction:

(a) $A\text{-}(B\text{-}L)_J\text{-}C\text{-}M\text{-}T\text{-}D$ (Formula I);
wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then $A\text{-}(B\text{-}L)_J\text{-}C$ and T-D are separate nucleic acid strands;
T is 17-135 nucleotides in length and comprises at least 50% sequence complementarity to B and C; and
D is 0-10 nucleotides in length and comprises at least 50% sequence complementarity to A;
and wherein segment A may be attached to segment D forming a loop;

(b) $D\text{-}T\text{-}T'\text{-}C\text{-}(L\text{-}B)_J\text{-}A$ (Formula II);
wherein D is 0-10 nucleotides in length;
T-T' is 17-135 nucleotides in length;
T' is 1-10 nucleotides in length and does not hybridize with T;
C is 4-15 nucleotides in length and comprises at least 50% sequence complementarity to T;
L is 3-25 nucleotides in length and does not hybridize with T;
B is 4-12 nucleotides in length and comprises at least 50% sequence complementarity to T;
J is an integer between 1 and 10;
A is 0-15 nucleotides in length and comprises at least 50% sequence complementarity to D;
and wherein segment T is attached to segment B forming a loop;

(c) $T\text{-}D\text{-}M\text{-}A\text{-}(B\text{-}L)_J\text{-}C$ (Formula III);
wherein T is 17-135 nucleotides in length;
D is 0-10 nucleotides in length;
M is 1-25 nucleotides in length or is absent, wherein if M is absent then T-D and $A\text{-}(B\text{-}L)_J\text{-}C$ are separate nucleic acid strands;
A is 0-15 nucleotides in length and comprises at least 50% sequence complementarity to D;
B is 4-12 nucleotides in length and comprises at least 50% sequence complementarity to T;
L is 3-25 nucleotides in length;
J is an integer between 1 and 10; and
C is 4-15 nucleotides in length;
and wherein segment T is attached to segment C forming a loop; or (d) $T\text{-}D\text{-}M\text{-}A\text{-}L_p\text{-}C$ (Formula IV);
wherein T is 17-31 nucleotides in length;
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

10. The method of claim 9, wherein:
(a) T of Formula I comprises at least 80% sequence complementarity to B and C;
(b) D of Formula I comprises at least 80% sequence complementarity to A;
(c) C of Formula II comprises at least 80% sequence complementarity to T;
(d) B of Formula II comprises at least 80% sequence complementarity to T;
(e) A of Formula II comprises at least 80% sequence complementarity to D;
(f) A of Formula III comprises at least 80% sequence complementarity to D;
(g) B of Formula III comprises at least 80% sequence complementarity to T;
(h) A of Formula IV comprises at least 80% sequence complementarity to D; and/or
(i) C of Formula IV comprises at least 80% sequence complementarity to T.

11. The method of claim 1, wherein each of the plurality of the blocked nucleic acid molecules comprises a modified nucleoside or nucleotide.

12. The method of claim 11, wherein the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

13. The method of claim 1, wherein there are at least ten different RNP1-NONs in the reaction mix.

14. The method of claim 13, wherein there are at least twenty-five different RNP1-NONs in the reaction mix.

15. The method of claim 14, wherein there are at least fifty different RNP1-NONs in the reaction mix.

16. The method of claim 15, wherein there are at least one hundred different RNP1-NONs in the reaction mix.

17. The method of claim 1, further comprising the steps of:
providing third ribonucleoprotein complexes (RNP1-NAs), wherein each of the RNP1-NAs comprises a third nucleic acid-guided nuclease and third gRNAs (gRNA1-NAs); wherein the gRNA1-NAs comprise a sequence complementary to a nucleic acid target of interest, and wherein the third nucleic acid-guided nuclease exhibits trans-cleavage activity;
contacting the reaction mix with the sample under conditions that allow nucleic acid targets of interest in the sample to bind the RNP1-NA, wherein:
upon binding of the nucleic acid target to the RNP1-NA, the nucleic acid target-bound RNP1-NA becomes active trans-cleaving at least one of the blocked nucleic acid molecules, thereby producing at least one unblocked nucleic acid molecule that can complex with RNP2; and
upon binding of the at least one unblocked nucleic acid molecule to the RNP2, the unblocked nucleic acid molecule-bound RNP2 becomes active trans-cleaving at least one more of the blocked nucleic acid molecules and at least one reporter moiety in a cascade;

allowing the cascade to continue; and detecting the reporter moieties, thereby detecting the target nucleic acid of interest in the sample.

18. The method of claim 17, wherein the reporter moieties produce a detectable signal upon trans-cleavage activity by the RNP1-NON, RNP1-NA and/or RNP2 to identify the presence of one or more non-nucleic acid targets of interest in the sample.

19. The method of claim 18, wherein the detectable signal is a fluorescent signal.

20. The method of claim 18, wherein the detectable signal is a phosphorescent signal.

21. The method of claim 17, wherein the aptamer is a riboswitch and wherein the riboswitch comprises an aptamer domain to an effector molecule of choice and an expression platform domain heterologous to the aptamer domain.

22. The method of claim 21, wherein the expression platform domain is selected from an expression platform from a cobalamin riboswitch, a cyclic AMP-GMP riboswitch, a cyclic di-AMP riboswitch, a cylic di-GMP riboswitch, a fluoride riboswitch, a Flavin mononucleotide (FMN) riboswitch, a glmS (glucose-6-pohosphate) riboswitch, a Glutamine riboswitch, a Glycine riboswitch, a Lysine riboswitch, a manganese riboswitch, a NiCo riboswitch, a PreQ1 (pre-queuosine 1) riboswitch, a purine riboswitch, an SAH (S-adenosylhomocysteine) riboswitch, an SAM (S-adenosyl methionine) riboswitch, an SAM-SAH (recognizes both S-adenosylhomocysteine and S-adenosyl methionine) riboswitch, a tetrahdrofolate riboswitch, a TPP (thiamin biosynthesis- and found in eukaryotes) riboswitch, and a SMP.STP riboswitch.

23. The method of claim 17, wherein the blocked nucleic acid molecule comprises a structure represented by any one of Formulas I-IV, wherein Formulas I-IV are in the 5'-to-3' direction:

(a) $A\text{-}(B\text{-}L)_J\text{-}C\text{-}M\text{-}T\text{-}D$ (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then $A\text{-}(B\text{-}L)_J\text{-}C$ and T-D are separate nucleic acid strands;
T is 17-135 nucleotides in length and comprises at least 50% sequence complementarity to B and C; and
D is 0-10 nucleotides in length and comprises at least 50% sequence complementarity to A;
and wherein segment A may be attached to segment D forming a loop;

(b) $D\text{-}T\text{-}T'\text{-}C\text{-}(L\text{-}B)_J\text{-}A$ (Formula II);

wherein D is 0-10 nucleotides in length;
T-T' is 17-135 nucleotides in length;
T' is 1-10 nucleotides in length and does not hybridize with T;
C is 4-15 nucleotides in length and comprises at least 50% sequence complementarity to T;
L is 3-25 nucleotides in length and does not hybridize with T;
B is 4-12 nucleotides in length and comprises at least 50% sequence complementarity to T;
J is an integer between 1 and 10;
A is 0-15 nucleotides in length and comprises at least 50% sequence complementarity to D;
and wherein segment T is attached to segment B forming a loop;

(c) $T\text{-}D\text{-}M\text{-}A\text{-}(B\text{-}L)_J\text{-}C$ (Formula III);

wherein T is 17-135 nucleotides in length;
D is 0-10 nucleotides in length;
M is 1-25 nucleotides in length or is absent, wherein if M is absent then T-D and $A\text{-}(B\text{-}L)_J\text{-}C$ are separate nucleic acid strands;
A is 0-15 nucleotides in length and comprises at least 50% sequence complementarity to D;
B is 4-12 nucleotides in length and comprises at least 50% sequence complementarity to T;
L is 3-25 nucleotides in length;
J is an integer between 1 and 10; and
C is 4-15 nucleotides in length;
and wherein segment T is attached to segment C forming a loop; or (d) $T\text{-}D\text{-}M\text{-}A\text{-}L_p\text{-}C$ (Formula IV);

wherein T is 17-31 nucleotides in length;
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

24. The method of claim 23, wherein:

(e) T of Formula I comprises at least 80% sequence complementarity to B and C;
(f) D of Formula I comprises at least 80% sequence complementarity to A;
(g) C of Formula II comprises at least 80% sequence complementarity to T;
(h) B of Formula II comprises at least 80% sequence complementarity to T;
(i) A of Formula II comprises at least 80% sequence complementarity to D;
(j) A of Formula III comprises at least 80% sequence complementarity to D;
(k) B of Formula III comprises at least 80% sequence complementarity to T;
(l) A of Formula IV comprises at least 80% sequence complementarity to D; and/or
(m) C of Formula IV comprises at least 80% sequence complementarity to T.

25. The method of claim 17, wherein each of the plurality of the blocked nucleic acid molecules comprises a modified nucleoside or nucleotide.

26. The method of claim 25, wherein the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

27. The method of claim 17, wherein there are at least ten different RNP1-NONs and/or RNP1-NAs in the reaction mix.

28. The method of claim 17, wherein there are at least twenty-five different RNP1-NONs and/or RNP1-NAs in the reaction mix.

29. The method of claim 28, wherein there are at least fifty different RNP1-NONs and/or RNP1-NAs in the reaction mix.

30. The method of claim 29, wherein there are at least one hundred different RNP1-NONs and/or RNP1-NAs in the reaction mix.

* * * * *

```
                          SEQUENCE LISTING

Sequence total quantity: 10
SEQ ID NO: 1            moltype = RNA  length = 45
FEATURE                 Location/Qualifiers
source                  1..45
                        mol_type = other RNA
                        organism = synthetic construct
SEQUENCE: 1
taatttctac taagtgtaga tgagaagtca tttaataagg ccact                       45

SEQ ID NO: 2            moltype = DNA  length = 24
FEATURE                 Location/Qualifiers
source                  1..24
                        mol_type = other DNA
                        organism = synthetic construct
SEQUENCE: 2
gagaagtcat ttaataaggc cact                                              24

SEQ ID NO: 3            moltype = DNA  length = 24
FEATURE                 Location/Qualifiers
source                  1..24
                        mol_type = other DNA
                        organism = synthetic construct
SEQUENCE: 3
ctcttcagta aattattccg gtga                                              24

SEQ ID NO: 4            moltype = RNA  length = 54
FEATURE                 Location/Qualifiers
source                  1..54
                        mol_type = other RNA
                        organism = synthetic construct
SEQUENCE: 4
nnnnnnnnnn ntatttctac taagtgtaga tgagagtcat ttaataaggc cact             54

SEQ ID NO: 5            moltype = RNA  length = 53
FEATURE                 Location/Qualifiers
source                  1..53
                        mol_type = other RNA
                        organism = synthetic construct
SEQUENCE: 5
nnnnnnnnta atttctacta agtgtagatg agaagtcatt taataaggcc act              53

SEQ ID NO: 6            moltype = DNA  length = 24
FEATURE                 Location/Qualifiers
source                  1..24
                        mol_type = other DNA
                        organism = synthetic construct
SEQUENCE: 6
gagaagtcat ttaataaggc cact                                              24

SEQ ID NO: 7            moltype = DNA  length = 24
FEATURE                 Location/Qualifiers
source                  1..24
                        mol_type = other DNA
                        organism = synthetic construct
```

```
SEQUENCE: 7
ctcttcagta aattattccg gtga                                              24

SEQ ID NO: 8           moltype = RNA  length = 56
FEATURE                Location/Qualifiers
source                 1..56
                       mol_type = other RNA
                       organism = synthetic construct
SEQUENCE: 8
nnnnnnnnnn ntaatttcta ctaagtgtag atagaggatc agggaataac gccact           56

SEQ ID NO: 9           moltype = RNA  length = 102
FEATURE                Location/Qualifiers
source                 1..102
                       mol_type = other RNA
                       organism = Bacillus subtilis
SEQUENCE: 9
acttgtataa cctaataata tggtttgagg gtgtctacca ttaaccgtaa atcctgatta       60
caaaatttgt ttatgacatt ttttgtaatc aggattttt tt                          102

SEQ ID NO: 10          moltype = RNA  length = 120
FEATURE                Location/Qualifiers
source                 1..120
                       mol_type = other RNA
                       organism = Bacillus subtilis
SEQUENCE: 10
gatcaacgct tcatataatc ctaatgatat ggtttgggag tttctaccaa gagccttaaa      60
ctcttgatta tgaagtctgt cgctttatcc gaaattttat aaagagaaga ctcatgaatt     120
```